United States Patent [19]
Wright et al.

[11] Patent Number: 5,928,624
[45] Date of Patent: Jul. 27, 1999

[54] COMPOSITIONS FOR NEUTRALIZATION OF LIPOPOLYSACCHARIDES

[75] Inventors: Samuel D. Wright, Westfield, N.J.; Mark M. Wurfel; Peter Eric Hailman, both of New York, N.Y.

[73] Assignee: The Rockefeller University, New York, N.Y.

[21] Appl. No.: 08/750,697

[22] PCT Filed: Jun. 7, 1995

[86] PCT No.: PCT/US95/07903

§ 371 Date: Dec. 16, 1996

§ 102(e) Date: Dec. 16, 1996

[87] PCT Pub. No.: WO95/34289

PCT Pub. Date: Dec. 21, 1995

Related U.S. Application Data

[63] Continuation-in-part of application No. 08/337,611, Nov. 10, 1994, which is a continuation-in-part of application No. 08/259,957, Jun. 14, 1994, abandoned.

[51] Int. Cl.⁶ .................................................. A61K 7/48
[52] U.S. Cl. ........................... 424/9.1; 436/71; 436/501; 436/811
[58] Field of Search .......................... 424/9.1; 436/503, 436/501, 519, 548, 71–811; 435/7.92

[56] References Cited

U.S. PATENT DOCUMENTS

| | | | |
|---|---|---|---|
| 5,128,318 | 7/1992 | Levine et al. | 514/2 |
| 5,344,822 | 9/1994 | Levine et al. | 514/13 |
| 5,484,705 | 1/1996 | White | 435/7.32 |
| 5,753,504 | 5/1998 | Kirkland | 425/340 |

FOREIGN PATENT DOCUMENTS

| | | |
|---|---|---|
| 2138925 | 1/1995 | Canada . |
| 0504043 | 9/1992 | European Pat. Off. . |
| 0663407 | 7/1995 | European Pat. Off. . |
| 88/09345 | 12/1988 | WIPO . |
| WO 89/12644 | 12/1989 | WIPO . |
| WO89/12644 | 12/1989 | WIPO . |
| WO 91/11464 | 8/1991 | WIPO . |
| 92-310101/38 | 9/1992 | WIPO . |
| 93/06228 | 4/1993 | WIPO . |
| WO 93/13201 | 7/1993 | WIPO . |
| 93/19772 | 10/1993 | WIPO . |
| 94/04177 | 3/1994 | WIPO . |

OTHER PUBLICATIONS

Fink et al. *Journal of Surgical Research*, vol. 49, pp. 186–196, 1990.

Cross et al, *Infection and Immunity*, vol. 61, No. 7, pp. 2741–2747, Jul. 1993.

Bone, *Annals. of Internal Medicine*, vol. 115, No. 6, pp. 457–469, Sep. 15, 1991.

Glauder et al, *The Lancet*, vol. 338, pp. 732–736, Sep. 21, 1991,

Bone (1991) Ann. Intl. Med. 115:457–69.

(List continued on next page.)

*Primary Examiner*—Gollamudi S. Kishore
*Attorney, Agent, or Firm*—Klauber & Jackson

[57] ABSTRACT

The present invention relates to compositions and methods for neutralizing lipopolysaccharide, and treatment of gram-negative sepsis based thereon. Accordingly, the invention is directed to a composition of homogeneous particles comprising phospholipids and a lipid exchange protein, such as phospholipid transfer protein or LPS binding protein. The lipid exchange protein is characterized by being capable of facilitating an exchange of lipopolysaccharide into the particles. In a specific embodiment, exemplified herein, the lipid particles are high density lipoprotein particles comprising apolipoprotein A-I (apo A-I), a phospholipid, and cholesterol or a lipid bilayer binding derivative thereof. In a specific example, the phospholipid is phosphatidylcholine (PC). In a specific example, the ratio of phosphatidylcholine: cholesterol: apolipoprotein A-I is approximately 80:4:1. The level of LPS exchange protein activity in a sample from a patient provides a diagnostic, monitoring, or prognostic indicator for a subject with endotoxemia, gram-negative sepsis, or septic shock.

12 Claims, 32 Drawing Sheets

OTHER PUBLICATIONS

Cross et al. (1993) Infect. Immun. 61:7741–7.
Glauder et al. (1991) Lancet 338:732–6.
Day et al., 1994, J. Biol. Chem. 269:9388.
Hailman et al., 1994, J. Exp. Med. 179:269.
van Kessel et al., 1994, J. Immunol. Meth., 172:25–31.
Flegel et al., 1993, Infect. Immunol. 61:5140.
Hubsch et al., 1993, Circ. Shock 40:14.
Levine et al., 1993, Proc. Natl. Acad. Sci. USA 90:12040.
Emancipator et al. (1992) Infect, Immunol. 60:596–601.
Frey et al. (1992) J. Exp. Med. 176:1665–71.
Wright et al. (1992) J. Exp. Med. 176:719–27.
Shumann et al., 1990, Science 249:1429–31.
Tobias et al., 1989, J. Biol. Chem. 264:10867–71.
Wright et al., 1989, J. Exp. Med. 170:1231–41.
Hesler et al., 1988, J. Biol. Chem. 263:5020–3.
Tollefson et al., 1988, J. Lipid Res. 29:1593–602.
Tobias et al. (1986) J. Exp. Med. 777–93.
Munford et al., 1981, Infect. Immunol. 34:835–43.
Ulevitch et al., 1979, J. Clin. Invest. 64:1516–24.
Ulevitch et al., 1978, J. Clin. Invest. 62:1313–24.
Skarnes et al., 1968, J. Bacteriology 95:2031.
Skarnes et al. (1958) J. Exp. Med. 108:685–99.
Rall et al. (1957) Am. J. Physiol. 188:559–62.

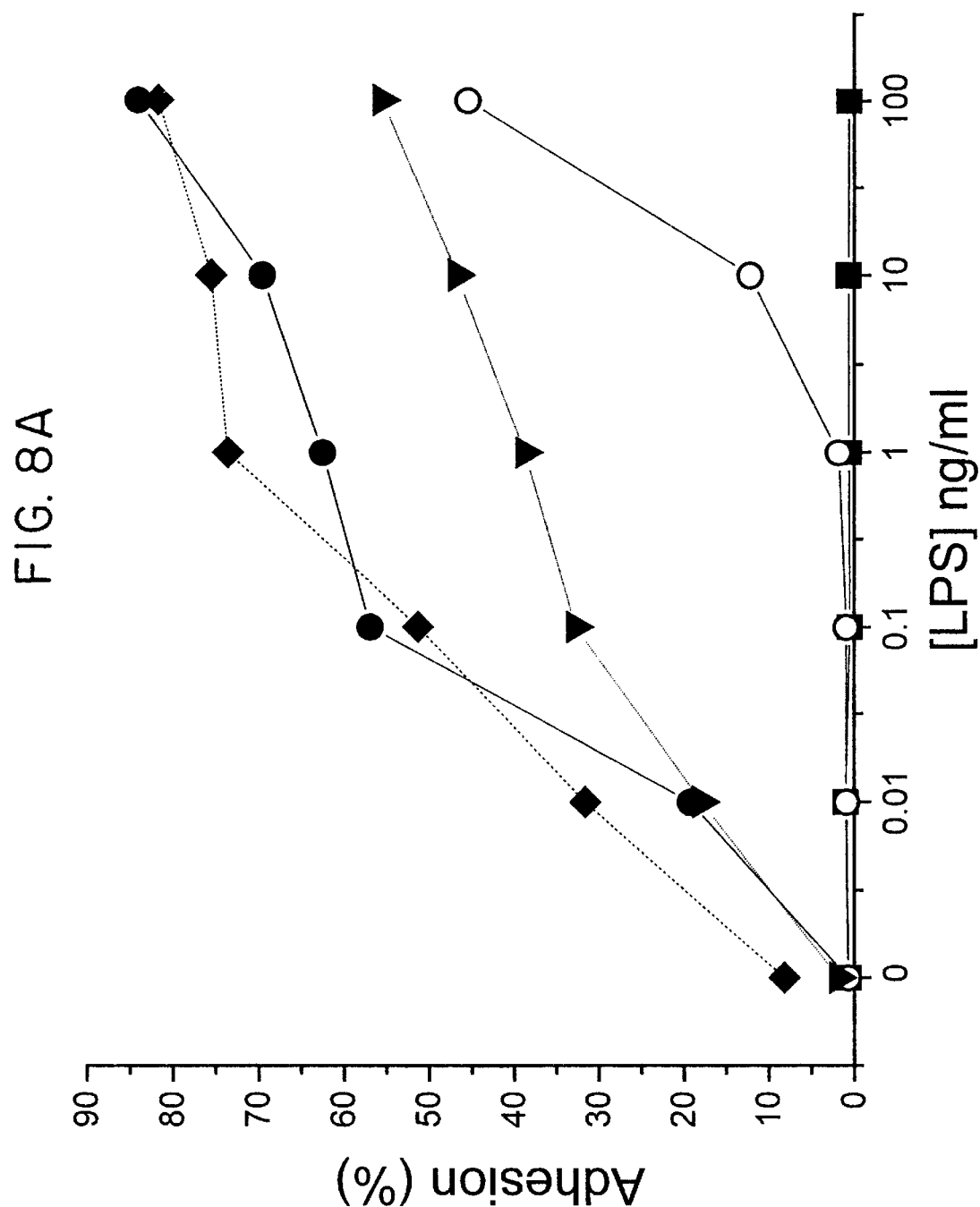

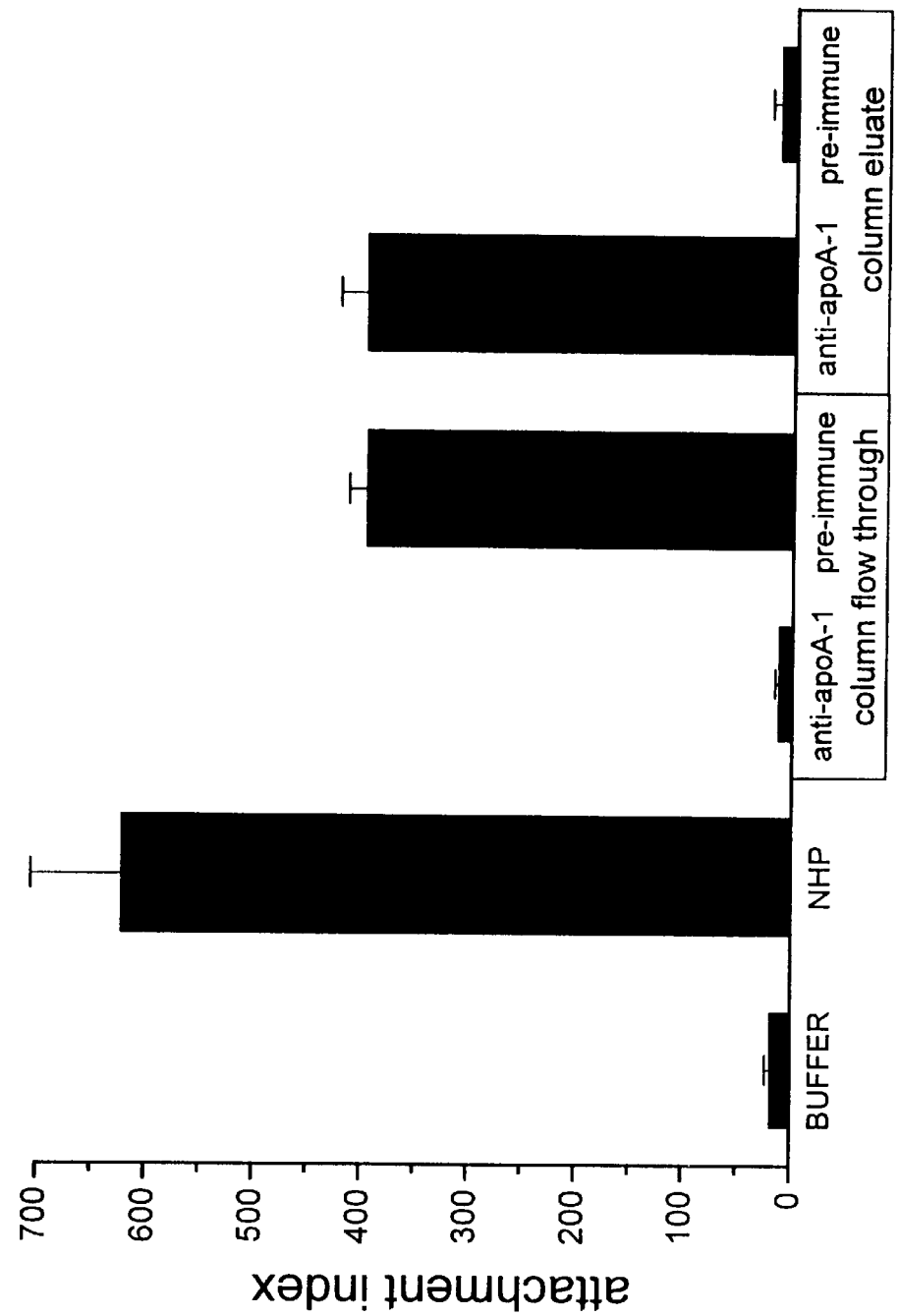

protein added

FIG. 20 a = Buffer
b = CD14
c = R-HDL

COMPOSITIONS FOR NEUTRALIZATION OF LIPOPOLYSACCHARIDES

RELATED APPLICATIONS

This application is a 371 of PCT/US95/07903 filed Jun. 7, 1995. The present application is also a Continuation-In-Part of copending application Ser. No. 08/337,611, filed Nov. 10, 1994, which is in turn a Continuation-In-Part of application Ser. No. 08/259,957, filed Jun. 14, 1994, now abandoned which is incorporated herein by reference in its entirety, and of which the present application claims the benefit of the filing date pursuant to 35 U.S.C. § 120.

The research leading to the present invention was supported in part by U.S. Public Health Service Grant No. AI-30556. The government may have certain rights in the invention.

FIELD OF THE INVENTION

The present invention relates to compositions and methods for neutralizing lipopolysaccharide, and treatment of gram-negative sepsis based thereon.

BACKGROUND OF THE INVENTION

Sepsis is morbid condition frequently induced by a toxin, the introduction or accumulation of which is most commonly caused by infection or trauma. The initial symptoms of sepsis or septic shock typically include chills, profuse sweat, irregularly remittent fever, prostration and the like, followed by persistent fever, hypotension leading to shock, neutropenia, leukopenia, disseminated intravascular coagulation, adult respiratory distress syndrome and multiple organ failure. These final symptoms, generally referred to as acute phase septic shock, almost invariably lead to death.

Sepsis-inducing toxins have been found associated with pathogenic bacteria, viruses, plants and venoms. Among the well described bacterial toxins are the endotoxins or lipopolysaccharides (LPS) of the gram-negative bacteria. These molecules are glycolipids that are ubiquitous in the outer membrane of all gram-negative bacteria. While the chemical structure of most of the LPS molecule is complex and diverse, a common feature is the lipid A region of LPS (Rietschel et al., 1984, In Handbook of Endotoxins, eds. R. A. Proctor and E. Th. Rietschel, Elsevier, Amsterdam 1:187–214). Recognition of lipid A in biologic systems initiates many, if not all, of the pathophysiologic changes of sepsis. Because lipid A structure is highly conserved among all types of gram-negative organisms, common pathophysiologic changes characterize gram-negative sepsis.

Current concepts support the contention that the primary response of the host (including man) to LPS involves the recognition of LPS by cells of the monocyte/macrophage lineage, followed by the rapid elaboration of a variety of cell products including the general group known as cytokines. Other cell types believed to participate in sepsis and in particular in the response to LPS are polymorphonuclear leukocytes and endothelial cells; each of these cell types are also capable of responding to LPS with the elaboration of potent inflammatory substances.

LPS is believed to be a primary cause of death in humans during gram-negative sepsis, particularly when the symptoms include adult respiratory distress syndrome (ARDS) (van Deventer et al., 1988, Lancet, 1:605: Ziegler et al., 1987, J. Infect. Dis. 136:19–28). For instance, one particular cytokine, tumor necrosis factor alpha/cachectin (TNF), has been reported to be a primary mediator of septic shock (Beutler et al., 1987, N. Eng. J. Med. 316:379). Intravenous injection of LPS endotoxin from bacteria into experimental animals and man produces a rapid, transient release of TNF (Beutler et al., 1985, J. Immunol. 135:3972; Mathison et al., 1988, J. Clin. Invest. 81:1925). Evidence that TNF is a critical mediator of septic shock comes primarily from experiments in which pretreatment of animals with anti-TNF antibodies reduces lethality (Beutler et al., 1985, Science 229:869; Mathison et al., supra). These reports suggest that interruption of the secretion of TNF caused by LPS or other factors would ameliorate the often lethal symptoms of sepsis.

Upon introduction of LPS into the blood, it may bind to a protein termed lipopolysaccharide binding protein (LBP). LBP is a 60 kD glycoprotein present at concentrations of less than about 5 $\mu$g/ml in the serum of healthy animals and man. During the acute phase, LBP is synthesized by hepatocytes, and reaches concentrations of 30–50 $\mu$g/ml in serum. LBP can be purified from acute phase human and rabbit serum (Tobias et al., 1986, J. Exp. Med. 164:777–793). LBP recognizes the lipid A region of LPS and forms complexes with both rough and smooth form LPS (Tobias et al., 1989, J. Biol. Chem. 264:10867–10871). LBP bears N-terminal sequence homology with the LPS-binding protein known as bactericidal permeability-increasing factor, (BPI) (Tobias et al., 1988, J. Biol. Chem. 263:13479–13481). BPI is stored in the specific granules of PMN (Weiss et al., 1987, Blood 69:652–659) and kills gram-negative bacteria by binding LPS and disrupting the permeability barrier (Weiss et al., 1984, J. Immunol. 132:3109–3115).

In contrast to BPI, LBP is not directly cytotoxic for gram-negative bacteria (Tobias et al., 1988, J. Biol. Chem. 263:13479–13481). Instead, LBP binding to LPS has been found to dramatically enhance the interaction of LPS with macrophages, indicating its role as an opsonin (Wright et al., 1989, J. Exp. Med. 170:1231–1241). Inhibition of LBP, e.g., with an anti-LBP antibody, has been suggested as therapeutically useful for treating endotoxin-mediated sepsis (International Patent Application No. PCT/US90/04250, filed Jul. 30, 1990).

Studies over the past few years have shown that plasma proteins play an important role in mediating responses of cells to low concentrations of bacterial lipopolysaccharide. Several lipid transfer proteins have been identified in human plasma which have sequence similarity as well as similar functions. Cholesterol ester transfer protein (CETP) facilitates the transfer of cholesterol esters, triglycerides, and phospholipids between lipoprotein particles (Albers et al., 1984, Arteriosclerosis 4:49–58). Phospholipid transfer protein (PLTP) mediates the exchange and transfer of phospholipids between lipoproteins (Tollefson et al., 1988, J. Lipid. Res. 29:1593–1602). LBP (Shumann et al., 1990, Science 249:1429) and Septin (Wright et al., 1992, J. Exp. Med. 176:719) interact with LPS and facilitate the binding of the LPS to CD14 (Hailman et al., 1994, J. Exp. Med. 179:269). CD14, a protein found on the surface of monocytes, macrophages and neutrophils (Goyert & Ferrero, 1987, In Leukocyte Typing III, McMichael et al., eds., Springer Verlag: New York, p. 613) then initiates responses of these cells. CD14 is also found as a soluble protein in the plasma, and complexes of LPS with soluble CD14 participate in responses of endothelial cells (Frey et al., 1992, J. Exp. Med. 176:1665), epithelial cells (Pugin et al., 1993, Proc. Natl. Acad. Sci. USA 90:2744), and probably other cell types that do not express membrane CD14. LBP is also able to mediate the transfer of lipopolysaccharide (LPS) to high-density lipoprotein (HDL) particles or phospholipids, resulting in the functional neutralization of LPS (Wurfel et al., 1994, J. Exp. Med. 180:1025–1035). These studies have emphasized the ability of plasma to potentiate responses to LPS. In short, plasma contains factors that enhance the ability of LPS to initiate cellular activation, and ultimately, septic shock.

In contrast, a number of older studies have focused on the ability of plasma to inactivate endotoxin (Rall et al., 1957, Am. J. Physiol. 188:559; Skarnes et al., 1958, J. Exp. Med. 108:685; Ulevitch et al., 1978, J. Clin. Invest. 62:1313). Incubation of LPS with plasma has been shown to block the ability of the LPS to cause fever and death in experimental animals (Skarnes et al., supra; Ulevitch et al., supra) and to block the ability of LPS to give a positive signal in the Limulus amebocyte lysate (LAL) assay (Johnson et al., 1977, Am. J. Pathology 88:559; Emancipator et al., 1992, Infect. Immunol. 60(2):596). This "detoxification" or neutralization of LPS is thought to occur without covalent modification of the LPS, because the LPS detoxified by plasma can be extracted with organic solvents and shows full activity (Rudbach & Johnson, 1964, Nature 202:811). Work from several laboratories has shown that plasma lipoproteins, particularly high-density lipoproteins (HDL), bind and neutralize LPS (Skarnes et al., 1968, J. Bacteriology 95:2031); Ulevitch et al., 1979, J. Clin. Invest. 64:1516; Munford et al., 1981, Infect. Immunol. 34(3):835; Flegel et al., 1993, Infect. Immunol. 61(12):5140) and that these particles may constitute the LPS-neutralizing activity in plasma.

An LPS neutralizing factor was previously identified a factor that inhibited binding of LPS to monocytes, macrophages, and polymorphonuclear leukocytes; destroyed LPS-coated erythrocyte binding to macrophages, and destroyed septin-dependent stimulation of polymorphonuclear leukocytes and monocytes (see copending U.S. patent application Ser. No. 08/188,644, filed Jan. 27, 1994, which is a continuation of application Ser. No. 07/814,775, filed Dec. 30, 1991, now abandoned, which was a continuation in part of application Ser. No. 07/473,609, filed Feb. 1, 1990, now abandoned, and see International Patent Publication WO 93/13201, published Jul. 8, 1993, by Wright, each of which is incorporated herein by reference in their entireties). The activity of "Septinase," as this factor was termed, could be inhibited by $\alpha_2$-macroglobulin. One mechanism by which this factor was believed to inactivate Septin was by proteolysis; other experimental data suggested that the factor inactivated LPS without destroying Septin. Whatever the underlying mechanism, Septinase permanently inactivated LPS.

A number of approaches for treating sepsis have been attempted. These include use of antibodies to LPS, use of antibodies to tumor necrosis factor, use of a soluble TNF receptor, use of a soluble interleukin-1 (IL-1) receptor, to name a few. While each approach has some efficacy, the overall results have been disappointing.

Thus, there is a need in the art for an effective pharmaceutical agent and method of treatment for neutralizing gram-negative endotoxin (i.e., LPS), in order to prevent or alleviate symptoms of sepsis and septic shock.

The citation of any reference herein should not be considered as an admission that such reference is available as prior art to the invention.

SUMMARY OF THE INVENTION

In its broadest aspect, the present invention is directed to a composition of homogeneous particles comprising phospholipids and a lipid exchange protein. The lipid exchange protein is characterized by being capable of facilitating an exchange of lipopolysaccharide into the particles.

In a preferred aspect, the lipid exchange protein is phospholipid transfer protein (PLTP; see Day et al., 1994, J. Biol. Chem. 269:9388), or a fragment, analog, or derivative thereof. In another embodiment, the lipid exchange protein is lipopolysaccharide binding protein (LBP), or a fragment, analog, or derivative thereof. The fragment, analog, or derivative of the lipid exchange protein according to the invention is functionally active, i.e., capable of facilitating the exchange of lipopolysaccharide into the lipoprotein particles. According to the invention, the lipid exchange protein, in particular PLTP or LBP, can function catalytically to exchange lipopolysaccharide into the lipoprotein particles, e.g., HDL particles.

In a specific embodiment, the phospholipids have acyl chains of about 8 to about 18 carbon atoms; or the phospholipids have acyl chains that contain one or more cis-double bonds. In a more particular embodiment, the phospholipids have acyl chains of greater than 14 to about 18 carbon atoms and one or more cis-double bonds. In an example, infra, the acyl chain of the phospholipid has 14 carbon atoms and contains one cis-double bond.

In specific embodiments, the phospholipids can be selected from the group consisting of phosphatidyl choline, phosphatidyl inositol, phosphatidyl serine, phosphatidyl ethanolamine, diphosphatidyl glycerol, sphingomyelin, cerebroside, a ganglioside, and a mixture thereof. Preferably, the phospholipids are selected from the group consisting of phosphatidyl choline, phosphatidyl inositol, and a mixture thereof.

In one particular embodiment, the composition may substantially lack an amphipathic alpha-helical peptide-containing molecule.

In another particular embodiment, the composition may include an amphipathic alpha-helical peptide-containing molecule. In particular, the amphipathic alpha-helical peptide-containing molecule can be an apolipoprotein or an amphipathic alpha-helical portion thereof. For example, but not by way of limitation, the apolipoprotein or fragment thereof may be selected from the group consisting of apolipoprotein A-I, apo-A-II, apo-A-IV, apo-B, apo-C-II, and apo-E. In a specific embodiment, the alpha-helical peptide-containing molecule is apolipoprotein A-I.

The composition can also comprise cholesterol or a lipid bilayer binding derivative thereof.

Thus, in a particular aspect, the present invention is directed to a composition comprising lipoprotein particles and a lipid exchange protein. In a specific embodiment, the lipoprotein particles are high density lipoprotein (HDL) particles; however, low density (LDL) and very low density lipoprotein (VLDL) particles may be used. Preferably, greater than about 1 in 20 lipoprotein particles contain the lipid exchange protein. In a more preferred aspect, greater than about 1 in 2 lipoprotein particles contain the lipid exchange protein; in yet a more preferred aspect, greater than about 9 in 10 lipoprotein particles contain the lipid exchange protein. Preferably, the lipoprotein particle components and lipid exchange protein are the native molecules found in a subject believed to be in need of treatment.

In a preferred aspect of the invention, the composition further comprises soluble CD14. Soluble CD14 dramatically accelerates the rate of lipid exchange mediated by LBP, e.g., by about 30-fold.

Accordingly, the instant invention provides a great advantage over antibody-based therapies for sepsis and septic shock, in that it can avoid the problems associated with host immunity to the therapeutic antibodies.

Another advantage of the invention is that the introduction of the compositions of the invention, which are an enriched or homogeneous composition of particles normally found in a mammalian subject, is not expected to mediate significant adverse side effects.

Yet a further advantage of the invention is that it is compatible with other modes of therapy for sepsis, e.g., use of antagonists of tumor necrosis factor or interleukin-1, such as antibodies thereto or soluble receptors therefor; aggressive antibiotic therapy; or use of other agents that directly inhibit endotoxin, such as antibodies to endotoxin. Accordingly, the invention provides for concurrent or sequential administration of a composition of the invention with another treatment for endotoxemia, sepsis, or septic shock.

In a specific embodiment, exemplified herein, the lipoprotein particles are high density lipoprotein particles comprising apolipoprotein A-I (apo A-I), a phospholipid, and cholesterol or a lipid bilayer binding derivative thereof. In a specific example, the phospholipid is phosphatidylcholine (PC). In a specific example, the ratio of phosphatidylcholine:cholesterol:apolipoprotein A-I is approximately 80:4:1.

In another specific embodiment, the ratio by weight of lipoprotein (or amphipathic α-helical portion thereof), if present, in particular high density lipoprotein, to lipid exchange protein, in particular LPS binding protein, ranges from about 10 to about 1000 (or the equivalent ratio if a fragment, rather than a whole protein, is used); more preferably, the ratio is about 100. In a further aspect, the concentration of lipoprotein, in particular high density lipoprotein, ranges from about 1 μg/ml to about 1 mg/ml; in a specific embodiment, the concentration of high density lipoprotein is about 100 μg/ml. If the composition lacks an amphipathic alpha-helical peptide-containing molecule, the lipid exchange protein may be present in a comparable ration to the phospholipids as if the amphiphilic polypeptide were present.

In a preferred aspect, the lipoprotein particles, in particular the high density lipoprotein particles, are homogeneous.

It has been discovered that a lipoprotein particle containing a protein that has primary structural similarity to lipid exchange proteins can facilitate transfer of LPS from vesicles or micelles into lipoproteins, in particular HDLs. Thus, the invention has important implications for treatment of diseases or disorders associated with the presence of LPS, i.e., endotoxin.

Accordingly, the invention further provides a pharmaceutical composition for treating endotoxemia comprising phospholipid particles containing a lipid exchange protein, i.e., a composition of the invention, and a pharmaceutically acceptable carrier or excipient. In a more particular embodiment, a pharmaceutical composition of the invention comprises high density lipoprotein particles comprising apolipoprotein A-I (apo A-I), a phospholipid, and cholesterol or a lipid bilayer binding derivative thereof, and phospholipid transfer protein or lipopolysaccharide binding protein. In a further aspect, the pharmaceutical composition comprises soluble CD14.

The invention further provides a method for treating gram-negative sepsis comprising administering an amount of a pharmaceutical composition of the invention effective to neutralize lipopolysaccharide to a subject believed to be in need of such treatment. In preferred aspect, when the lipid exchange protein is LBP, the method further comprises administering soluble CD14.

The invention also provides methods of diagnosis, prognosis, or monitoring of a gram-negative infection, endotoxin-mediated sepsis, or septic shock. The method comprises measuring the level of lipoprotein particles that contain a lipid exchange protein that is characterized by being capable of facilitating an exchange of lipopolysaccharide into the high density lipoprotein particles; and comparing the level to a level in the patient at an earlier time, wherein an increase in the level indicates greater probability of a positive outcome of the sepsis. In one embodiment, this measurement is a functional measurement of the capacity of plasma from the subject to neutralize LPS. In another embodiment, the measurement can be performed by an immunoassay technique, or it equivalent using a specific binding partner.

In a particular embodiment, the lipoprotein is a high density lipoprotein containing lipoprotein A-I, and the lipid exchange protein is lipopolysaccharide binding protein. Thus, the method may involve detecting a proportion of lipoprotein particles containing apolipoprotein A-I that also contain lipopolysaccharide binding protein, e.g., by a sandwich immunoassay.

It is a primary object of the invention is to provide a composition for neutralizing the activity of LPS.

Another object of the invention is to provide a composition comprising lipid-containing particles and a lipid exchange protein, that facilitate sequestration of LPS in the lipid particle, and neutralization of LPS activity.

Yet another object of the invention is to provide a composition for neutralizing LPS or endotoxin in vitro or in vivo.

Still another object of the invention is to provide a pharmaceutical composition for introduction into a subject believed to be suffering from gram-negative sepsis, i.e., a systemic infection with a gram-negative bacteria.

Accordingly, another object of the invention is to provide a pharmaceutical composition for treating endotoxin-mediated septic shock.

A further object of the invention is to provide a diagnostic or prognostic indicator for the outcome of an episode of sepsis or septic shock.

Still other objects of the invention will become clear upon review of the accompanying drawings and detailed description of the invention.

BRIEF DESCRIPTION OF THE DRAWINGS

FIG. 8. LBP/Septin activity copurifies with Lp(A-I) particles. (A) The indicated concentrations of R595 LPS were incubated for 10 minutes at 37° C. in the presence of buffer (AHPBS) alone (■), 10% NHP (●), 10% apoA-I depleted plasma (○), 10% purified Lp(A-I) particles (▼) or 10% pre-immune control (sham) depleted plasma (♦). The ability of these mixtures to stimulate adhesion of PMN to fibrinogen was measured. Each point represents the mean of 3 wells of a representative experiment repeated three times. (B) ELPS were incubated in the presence of a 1:80 dilution of the indicated samples for 10 minutes at 37° C. Treated ELPS were washed, added to a monolayer of macrophages, and binding was evaluated as described in Materials and Methods. Each bar represents the mean of three wells +/− s.d. of a representative experiment repeated three times.

Liposomes were made by drying down PC, resuspending in PBS, and sonicating for 5 minutes in a bath type instrument.

Figure 15:
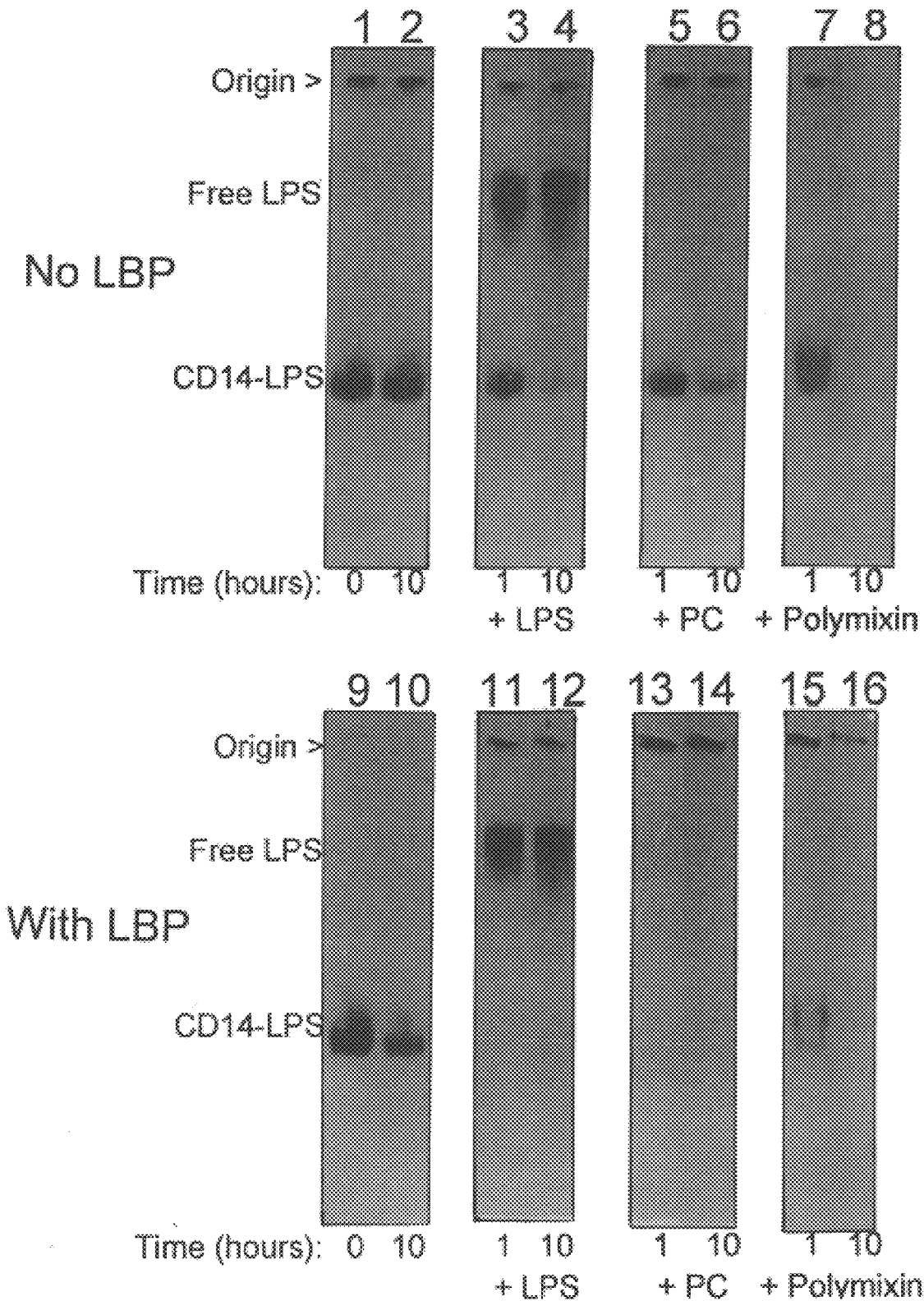

FIG. 15. rLBP accelerates the dissociation of $^3$H-LPS from sCD14. sCD14-$^3$H-LPS complexes were formed by preincubating 250 μg/ml sCD14 with 4 μg/ml $^3$H-LPS for 16 hours at 37° C. sCD14-$^3$H-LPS complexes were then diluted 1:5 and incubated alone or with unlabeled LPS (100 μg/ml; lanes 3, 4, 11, 12), phosphatidylcholine (PC) (100 μg/ml; lanes 5, 6, 13, 14), or polymicin B sulfate (10 μg/ml; lanes 7, 8, 15, 16), in the presence (B, lanes 9–16) or absence (A, lanes 1–8) of rLBP (1 μg/ml) for 1 hour or 10 hours in PBS. These dilutions provide unlabeled LPS and PC at 100-fold weight excess over $^3$H-LPS. The samples were then subjected to native polyacrylamide gel electrophoresis and $^3$H-LPS was detected by fluorography. In the absence of LBP, the $^3$H-sCD14 complexes are stable for 10 hours in the presence of PC liposomes (lane 6). However, addition of LBP enables complete transfer of $^3$H-LPS from sCD14 into the PC within 1 hour (lane 13).

Figure 16:
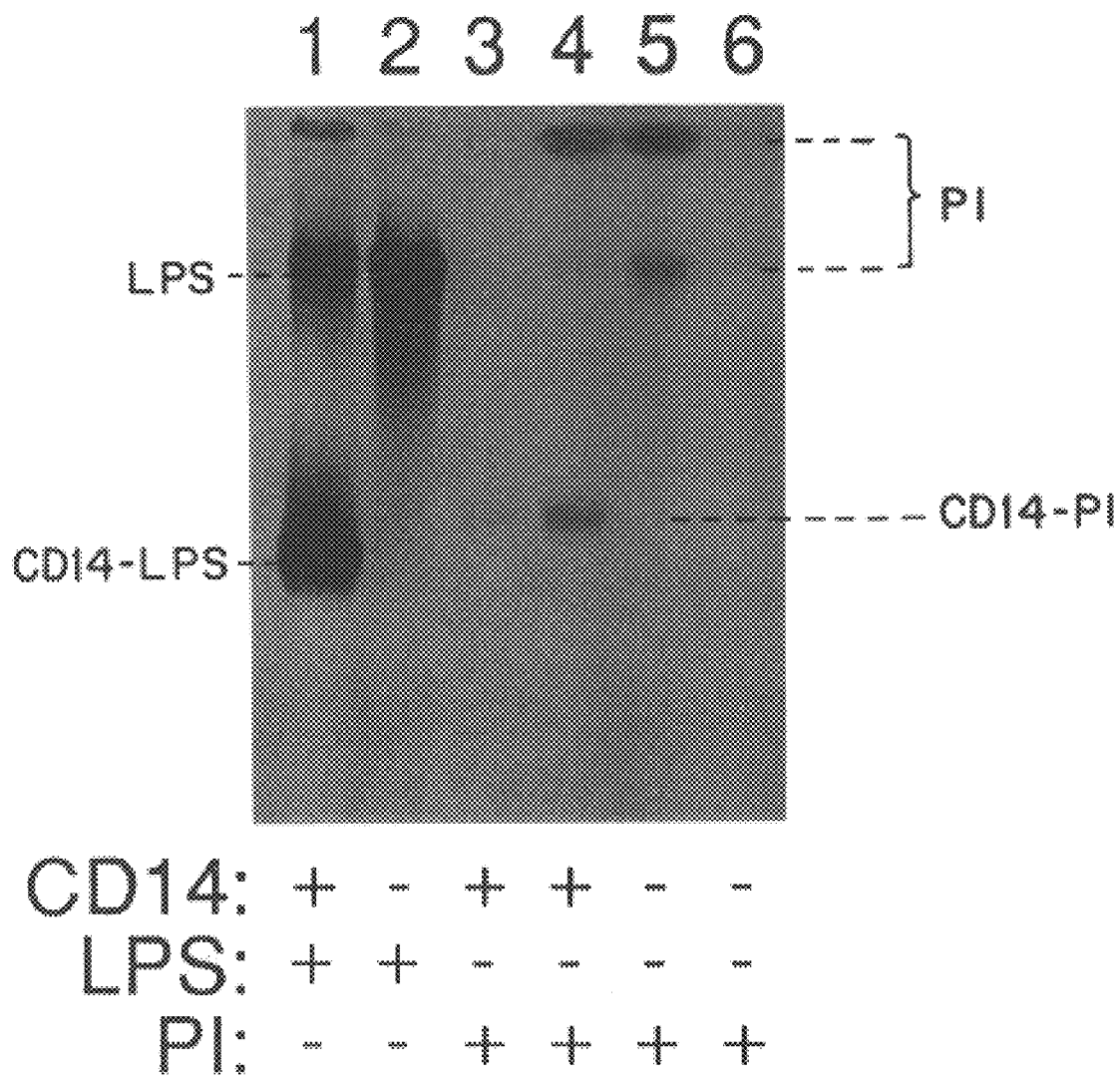

FIG. 16. $^3$H-Phosphatidylinositol (PI) comigrates with sCD14 in native PAGE. $^3$H-LPS (lanes 1–2) or $^3$H-PI (lanes 3–6) was incubated alone or with sCD14 (100 μg/ml, 2 μM) for 2 hours at 37° C. in PBS with 1 mM EDTA, run in a native polyacrylamide gel, and detected by fluorography. Lane 1, rsCD14+$^3$H-LPS (2 μM). Lane 2, $^3$H-LPS (2 μM). Lane 3, rsCD14+$^3$H-PI (2 μ). Lane 4, rsCD14+$^3$H-PI (18 μM). Lane 5, $^3$H-PI (18 μM). Lane 6, $^3$H-PI (2 μM).

Figure 17:
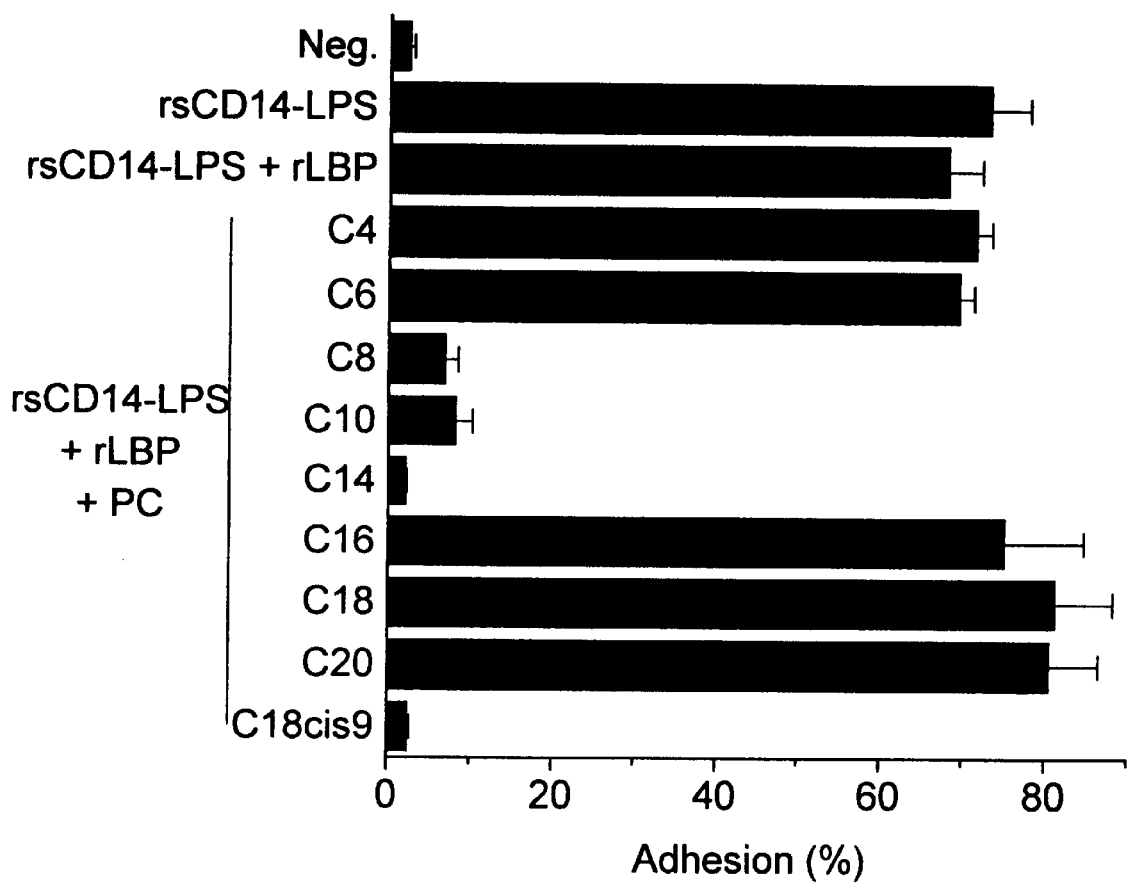

FIG. 17. Chain length and unsaturation of fatty acyl chains of PC affect neutralization of rsCD14-LPS. rsCD14-LPS complexes (as in FIG. 11, final concentrations 500 ng/ml rsCD14 and 10 ng/ml LPS) were preincubated alone, with rLBP (1 μg/ml), or with rLBP and synthetic PC (100 μM) for 2 hours at 37° C., then assayed for their ability to induce adhesion of PMN to fibrinogen-coated surfaces. The PC preparations used have saturated fatty acyl chains with the number of carbons indicated in the figure (C4, C6, etc.) at the 1 and 2 positions. C18cis9 PC has double bonds at the 9 positions of both fatty acyl chains.

Figure 18:
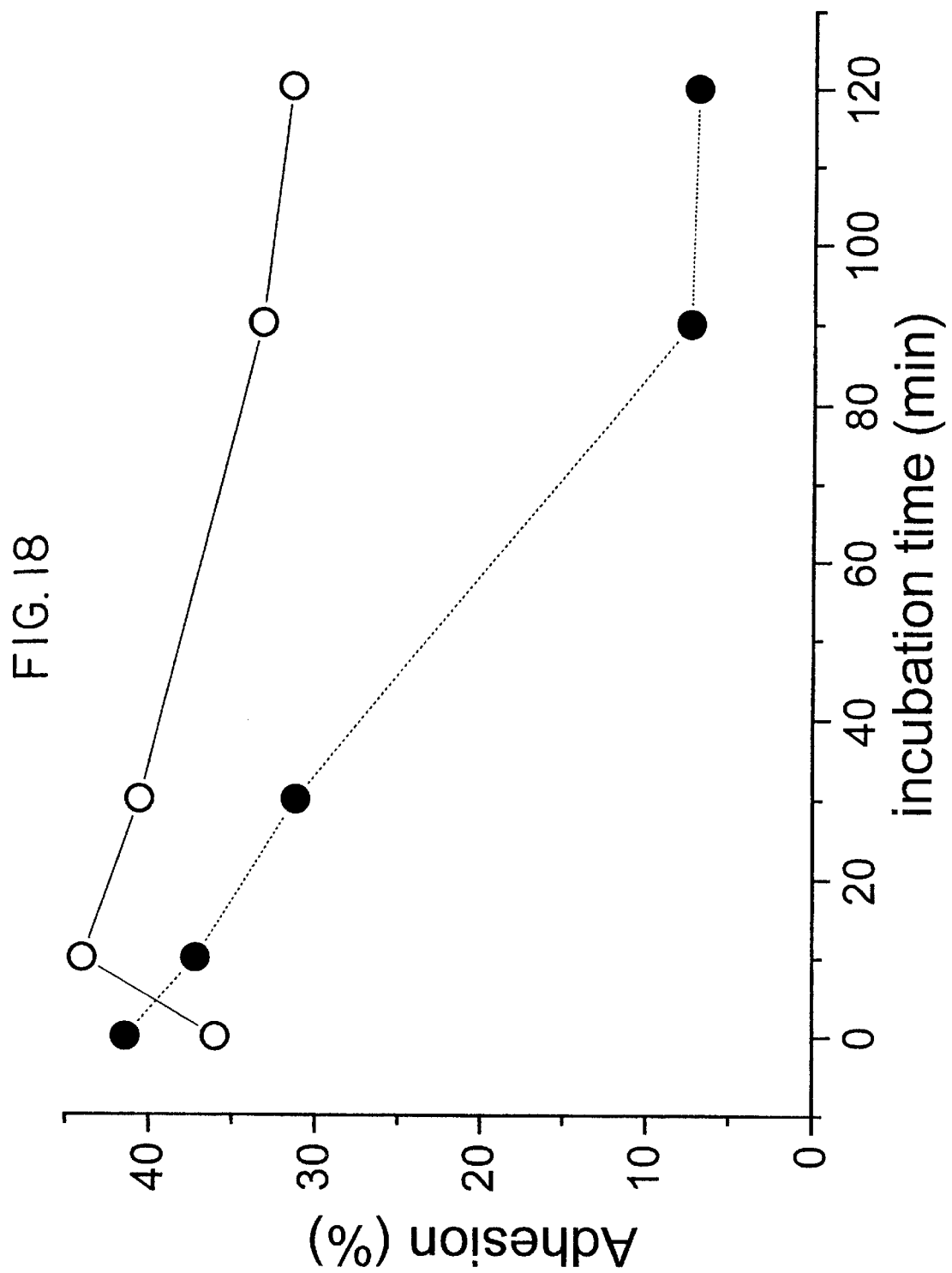

FIG. 18. Acute phase plasma exhibits accelerated neutralization of LPS. LPS (E. coli K12, 1 ng/ml) was incubated for the stated intervals at 37° C. with normal human plasma (NHP, 10%) pooled from healthy donors (○) or acute phase human plasma (APHP, 10%) from a patient in septic shock (●). PMN were then added and adhesion to fibrinogen-coated surfaces evaluated as described. Values represent the mean of 3 wells.

Figure 19:
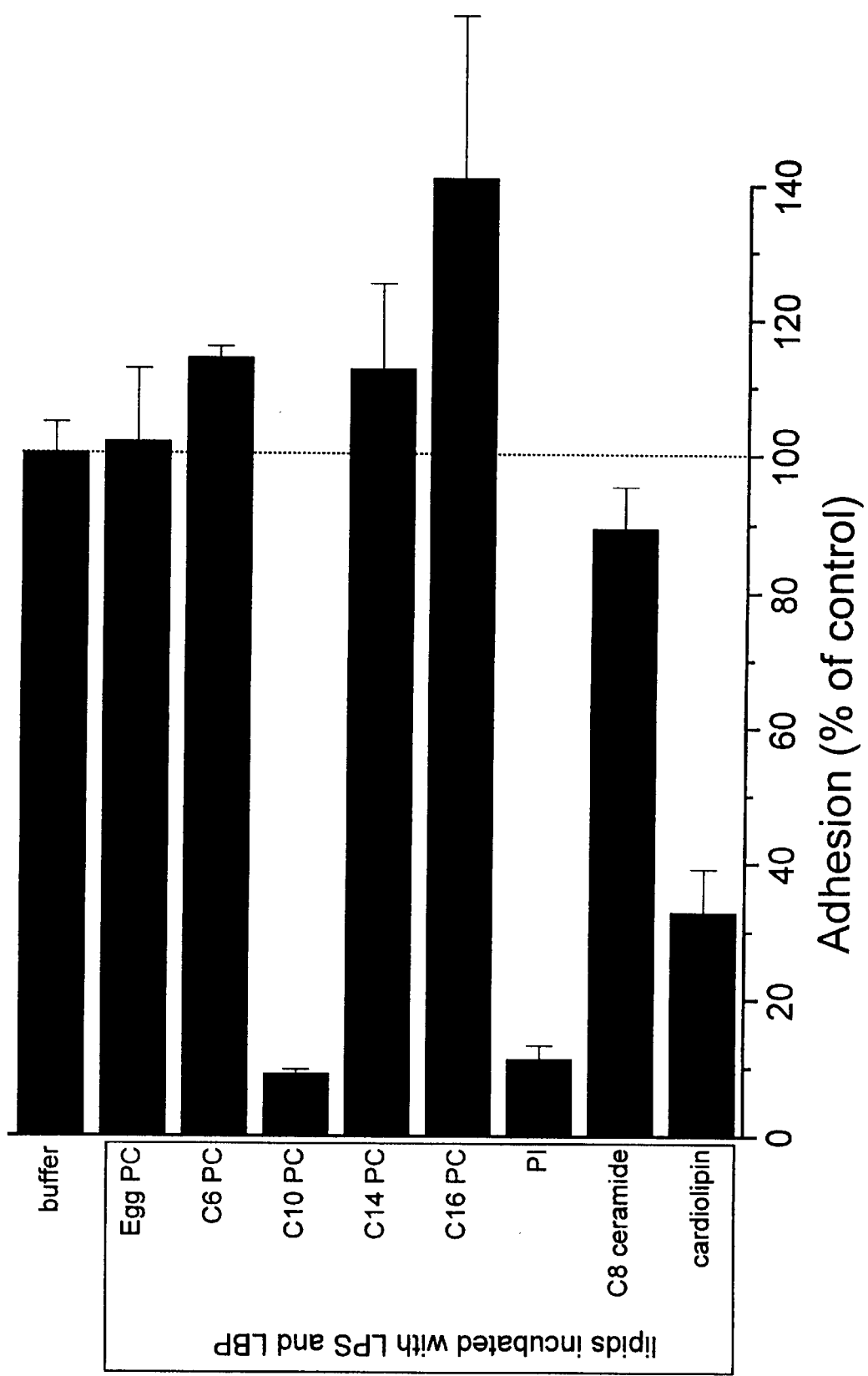

FIG. 19. Neutralization of LPS by different lipids. LPS (S. minnesota Ra, 10 ng/ml) and rLBP (1 μg/ml) were incubated for 2 hours at 37° C. with the lipids stated on the Y axis (10 μM). The biologically active LPS remaining was assessed by adding fluoresceinated neutrophils, incubating 10 minutes at 37° C. and then evaluating the binding of the neutrophils to fibrinogen coated surfaces. Values are expressed as % stimulation of adhesion, which represents the adhesion observed, in each case, as a percent of the adhesion observed in the buffer control. Each column represents the mean of 3 wells +/- s.d. of a representative experiment repeated twice.

Figure 20:
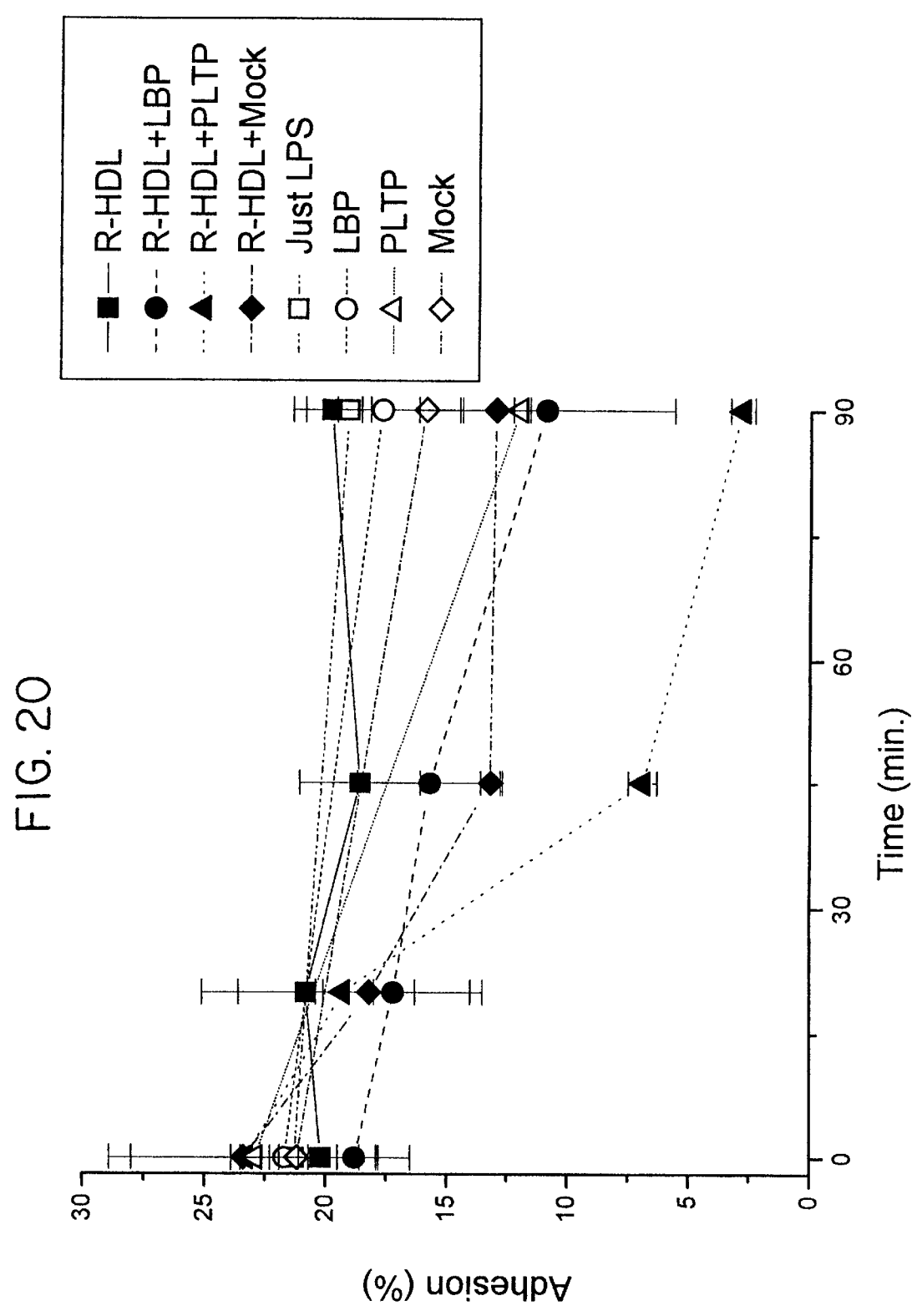

FIG. 20. PLTP enables rapid neutralization of LPS by R-HDL. LPS was incubated alone (□) or with various combinations of R-HDL (■; reconstituted HDL particles, 100 μg/ml), PLTP (▲ without R-HDL, ▲ in with R-HDL; concentrated culture medium from PLTP-transfected cells, diluted to the original concentration), and control medium (◇ without R-HDL, ♦ with R-HDL; concentrated culture medium from mock-transfected cells, diluted to the original concentration, marked "mock" in figure) for the indicated times at 37° C. in PBS with 0.5% human serum albumin. LBP was then added to samples to a final concentration of 1 μg/ml (○ without R-HDL, ● with R-HDL) followed by fluorescently labelled PMN to a final concentration of 3.3× 10$^6$ per ml. Samples were incubated for 10 min. at 37° C. and adhesion of PMN to fibrinogen-coated plates was measured. Error bars represent standard deviations of triplicate determinations.

Figure 21:
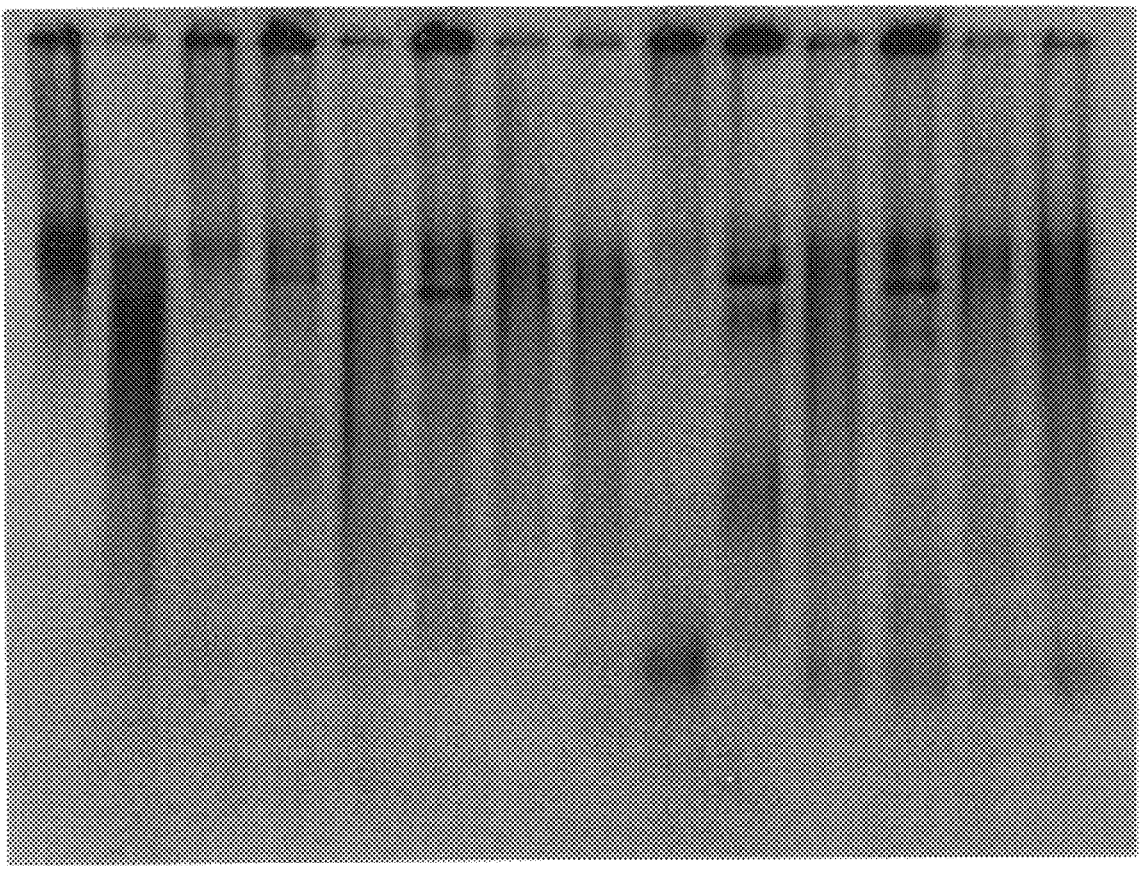

FIG. 21. PLTP accelerates the binding of $^3$H-LPS to R-HDL. $^3$H-LPS (1 μg/ml) was incubated with various combinations of R-HDL (100 μg/ml) LBP (1 μg/ml). CD14 (5 μg/ml), PLTP (5.6× concentrated culture medium from PLTP-transfected cells) or control medium (4× concentrated culture medium from mock-transfected cells) for 2 h at 37° C. in PBS. The mixtures were then electrophoresed in an 8–166% native polyacrylamide gel and $^3$H-LPS was detected by fluorography. Lane 1; $^3$H-LPS alone. Lane 2, $^3$H-LPS+R-HDL. Lane 3, $^3$HLPS+LBP. Lane 4, $^3$H-LPS+LBP+R-HDL. Lane 5, $^3$H-LPS+PLTp. Lane 6, $^3$H-LPS+PLTP+R-HDL. Lane 7, $^3$H-LPS+control medium. Lane 8, $^3$H-LPS+control medium R-HDL. Lane 9, $^3$H-LPS+LBP+CD14. Lane 10, $^3$H-LPS+LBP+CD14+R-HDL. Lane 11, $^3$H-LPS+PLTP+CD14. Lane 12, $^3$H-LPS+PLTP+CD14+R-HDL. Lane 13, $^3$H-LPS+control medium+CD14. Lane 14, $^3$H-LPS+control medium+CD14+R-HDL.

Figure 22:
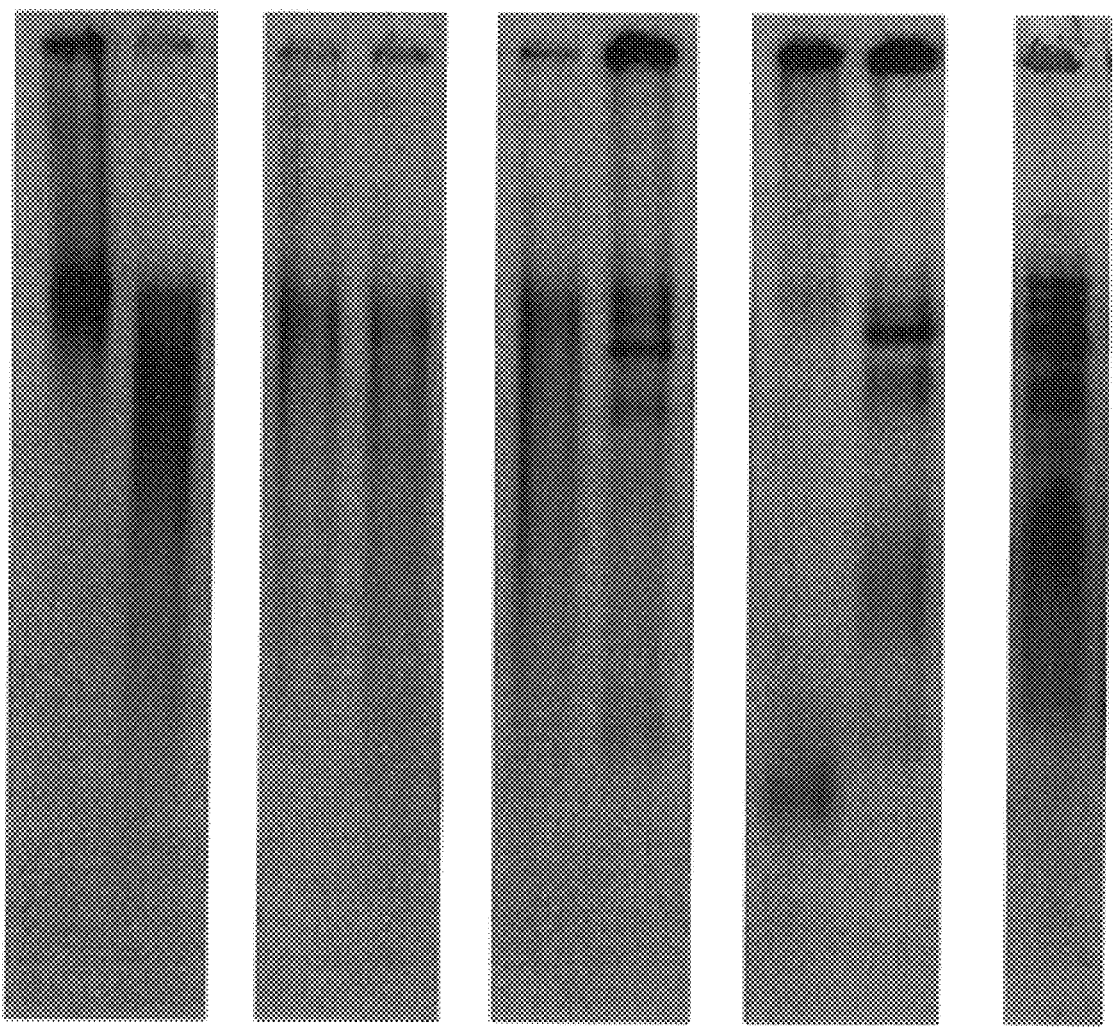

FIG. 22. rPLTP medium mediates the binding of $^3$H-LPS to R-HDL. $^3$H-LPS (1 μg/ml) was incubated in PBS for 2 h at 37° C. alone (lane 1), with R-HDL (100 μg/ml) (lane 2), with control medium (2×) (lane 3), with control medium and R-HDL (lane 4), with rPLTP medium (2×) (lane 5), with rPLTP medium and R-HDL (lane 6), with LBP and sCD14 (lane 7) or with LBP, sCD14 and R-HDL (lane 8). Samples were subjected to native PAGE and $^3$H-LPS was visualized by fluorography. R-HDL was electrophoresed and visualized by silver staining for comparison (lane 9).

Figure 23:
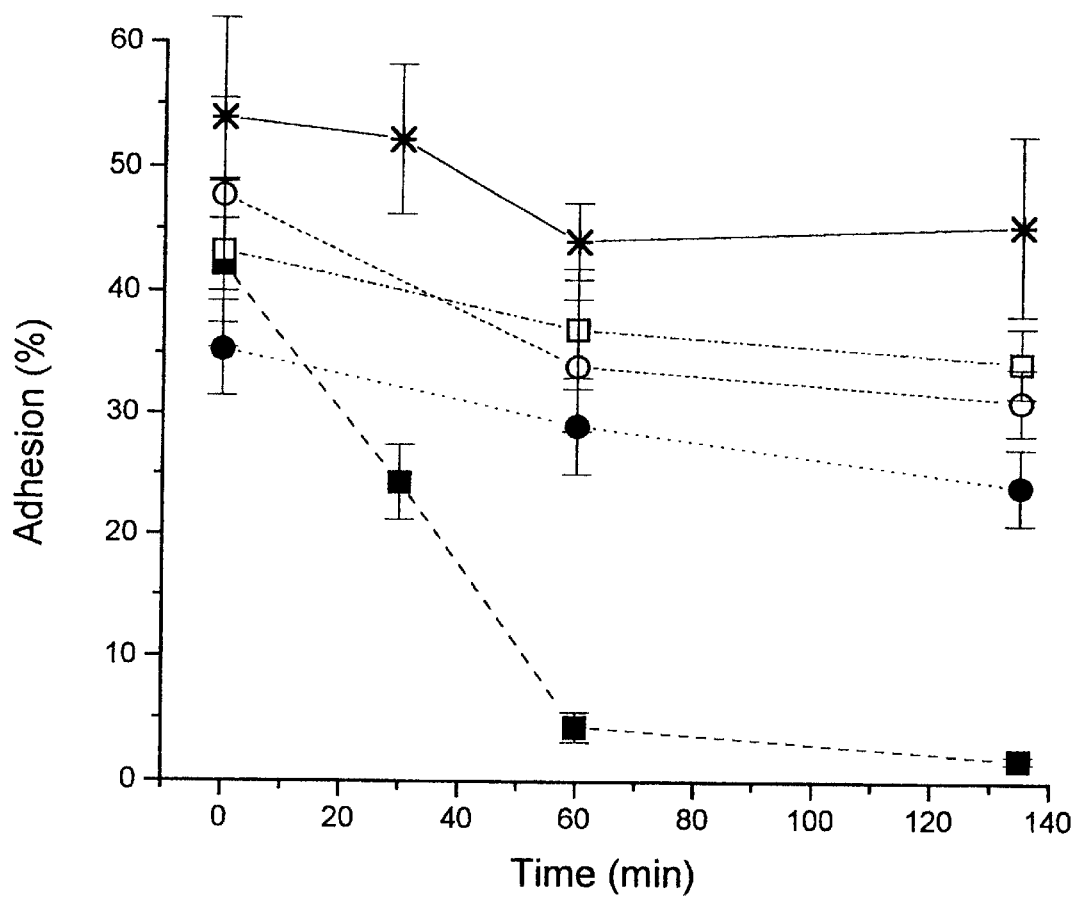

FIG. 23. rPLTP medium mediates the neutralization of LPS by R-HDL. LPS (10 ng/ml) was incubated for the indicated intervals in the presence of R-HDL (100 (g/ml) (γ), R-HDL and rPLTP medium (2×) (■), R-HDL and control medium (2×) (●), rPLTP medium (□), or control medium (○). Biologically active LPS was assessed by adding PMN and measuring their binding to fibrinogen. Each point represents the mean of triplicate determinations, ±S.D.

Figure 24:
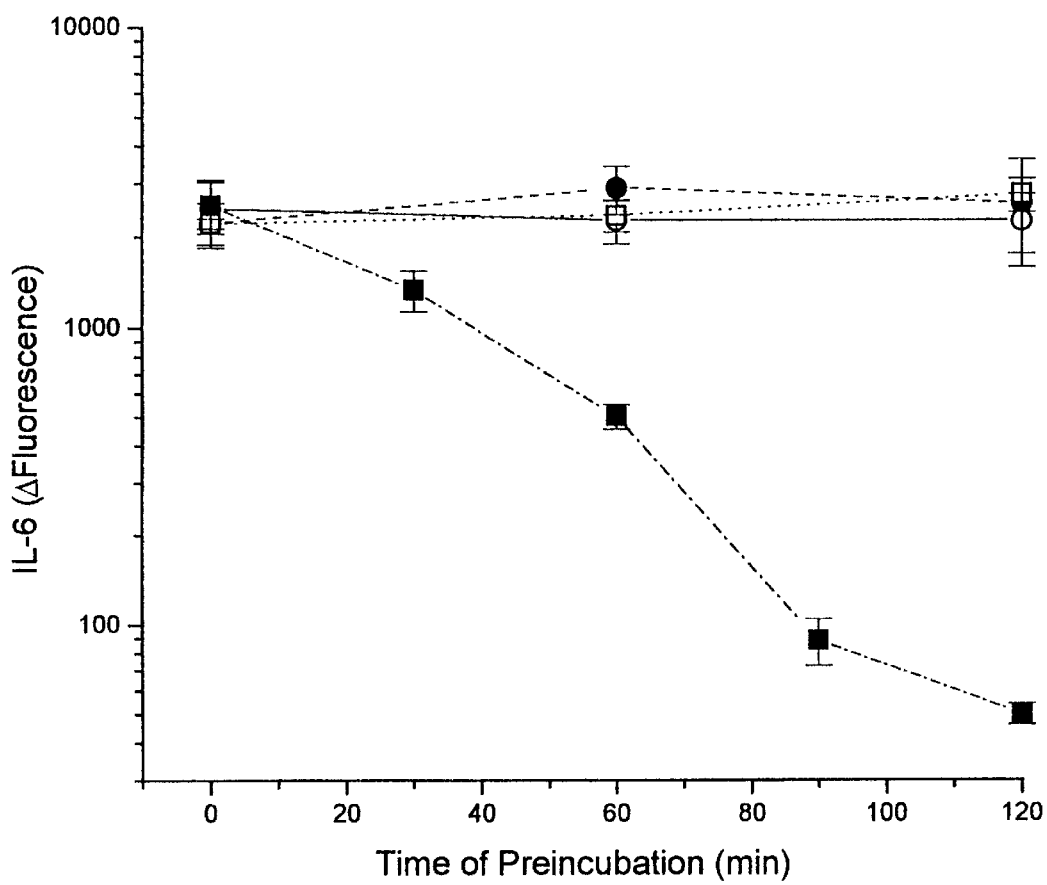

FIG. 24. rPLTP medium mediates the neutralization of LPS by R-HDL. LPS (10 ng/ml) was incubated for the indicated intervals at 37° C. alone (○), with R-HDL (100 μg/ml) (●), with rPLTP medium (2×) (□), or with rPLTP medium and R-HDL (■). Biologically active LPS was measured by adding a portion of each sample to whole blood and measuring production of IL-6. Each point represents the mean ±S.D. of triplicate determinations of IL-6 production, measured by ELISA.

Figure 25:
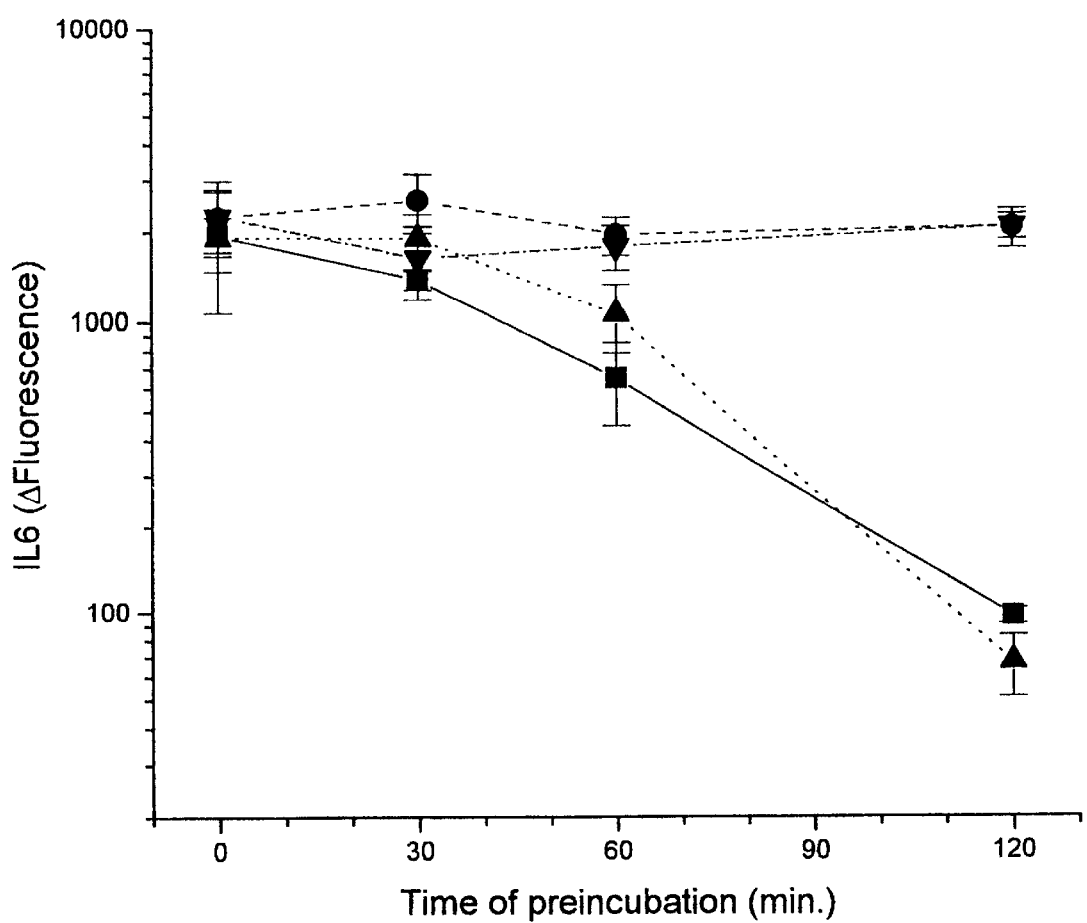

FIG. 25. rPLTP medium does not mediate neutralization of LPS by modifying R-HDL. LPS (10 ng/ml) was incubated with R-HDL (100 μg/ml) at 37° C. for the indicated times in the presence (▲, ■, ●) or absence (▼) of rPLTP medium (2×). In some cases (■, ●), R-HDL was preincubated with rPLTP medium for 1 h at 37° C. before addition of LPS, and in one case (●), anti-PLTP was added at the same time as LPS. Biologically active LPS was assessed by measuring IL-6 production in whole blood as in FIG. 24.

Figure 26:
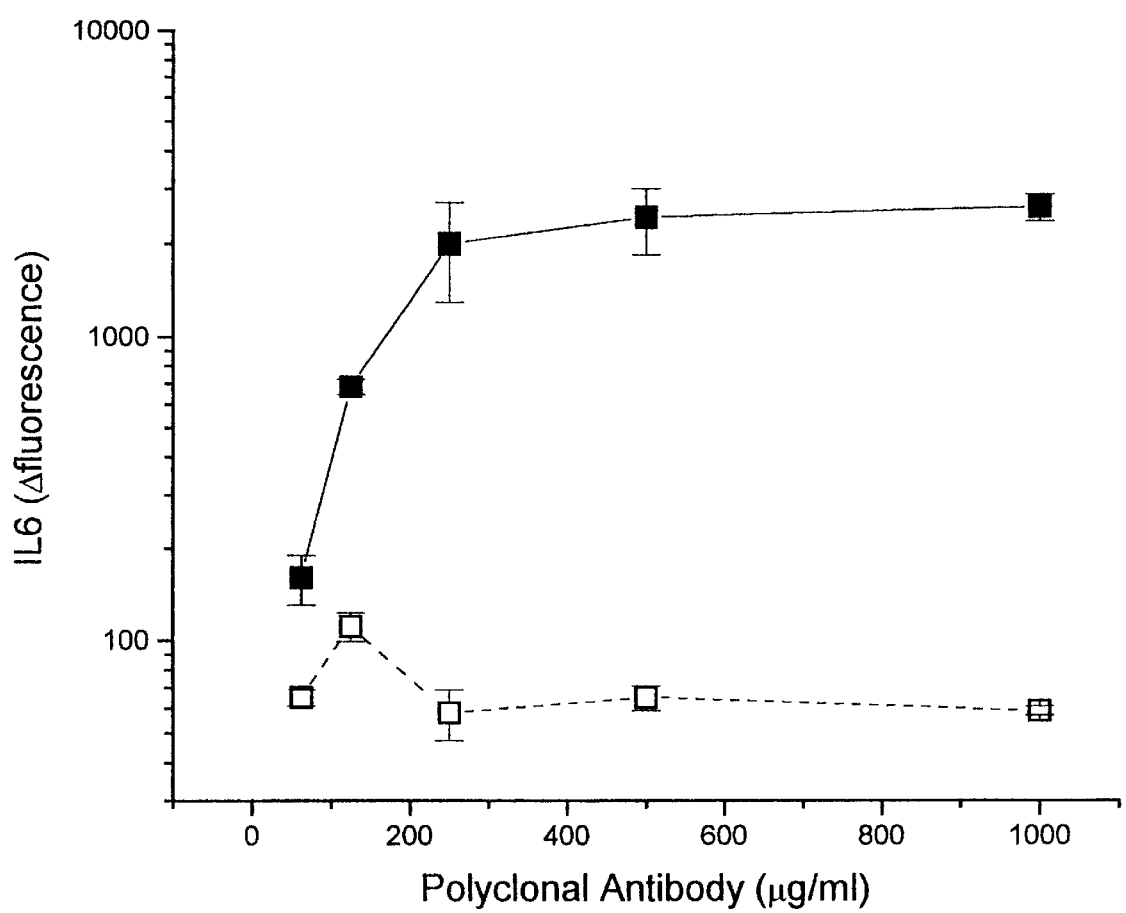

FIG. 26. Anti-PLTP polyclonal antibody inhibits the neutralization of LPS by R-HDL and rPLTP medium. LPS (10 ng/ml) was incubated for 2 h at 37° C. with R-HDL (100 μg/ml) and rPLTP medium (2×) in the presence of increasing concentrations of anti-PLTP (■) or control (□) antibody. Biologically active LPS was assessed by measuring IL-6 production in whole blood as in FIG. 24.

Figure 27A:
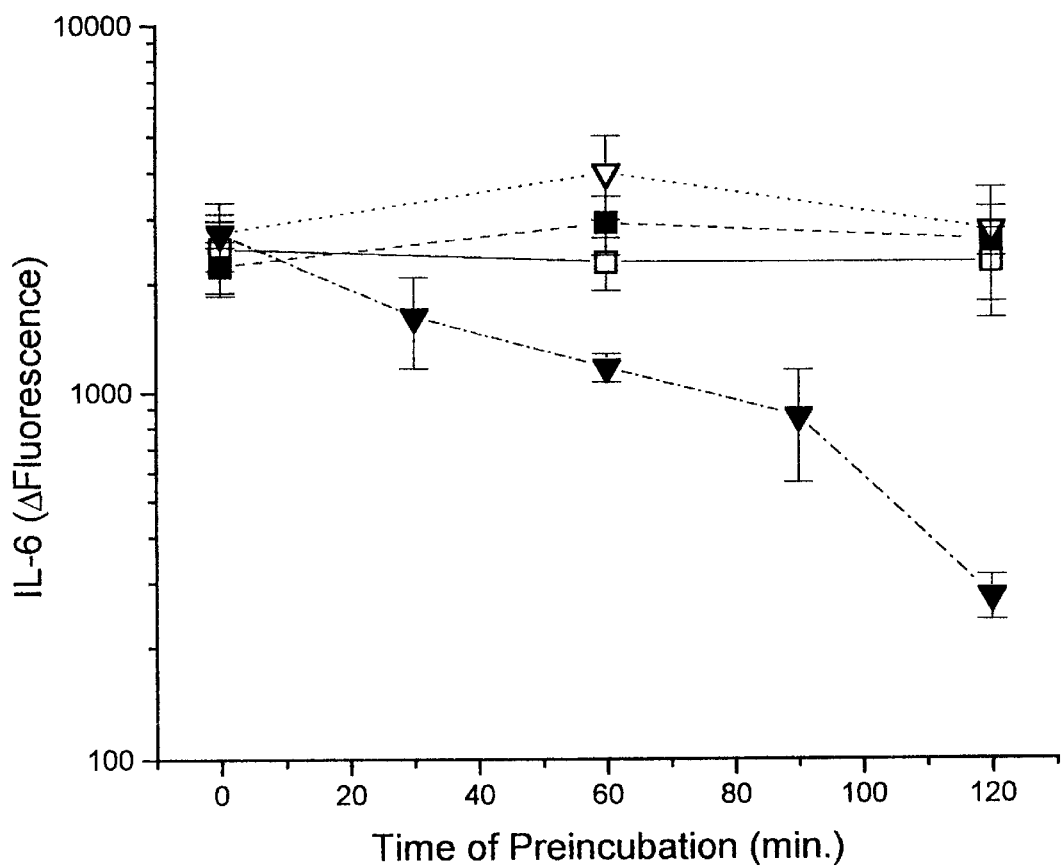

FIG. 27A. Normal human plasma mediates the neutralization of LPS by R-HDL. LPS (10 ng/ml) was incubated at 37° C. for increasing times alone (□), with R-HDL (100 μg/ml) (■), with NHP (3%) (▽), or with NHP and R-HDL (▲). Biologically active LPS was assessed by measuring IL-6 production in whole blood as in FIG. 24.

Figure 27B:
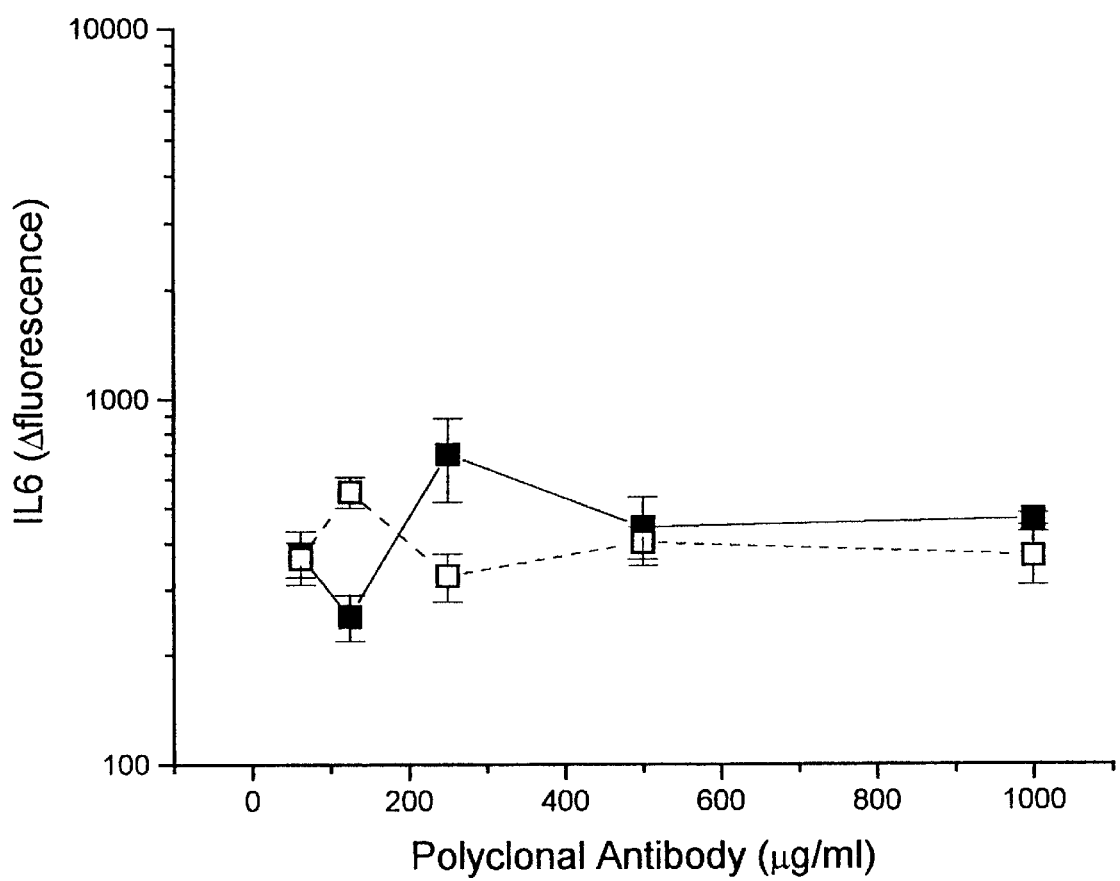

FIG. 27B. Anti-PLTP polyclonal antibody does not inhibit the neutralization of LPS by R-HDL and NHP. LPS (10 ng/ml) was incubated for 2 h at 37° C. with R-HDL (100 μg/ml) and NHP (3%) in the presence of increasing concentrations of anti-PLTP (■) or control (□) antibody. Biologically active LPS was assessed by measuring IL-6 production in whole blood as in FIG. 24.

Figure 28:
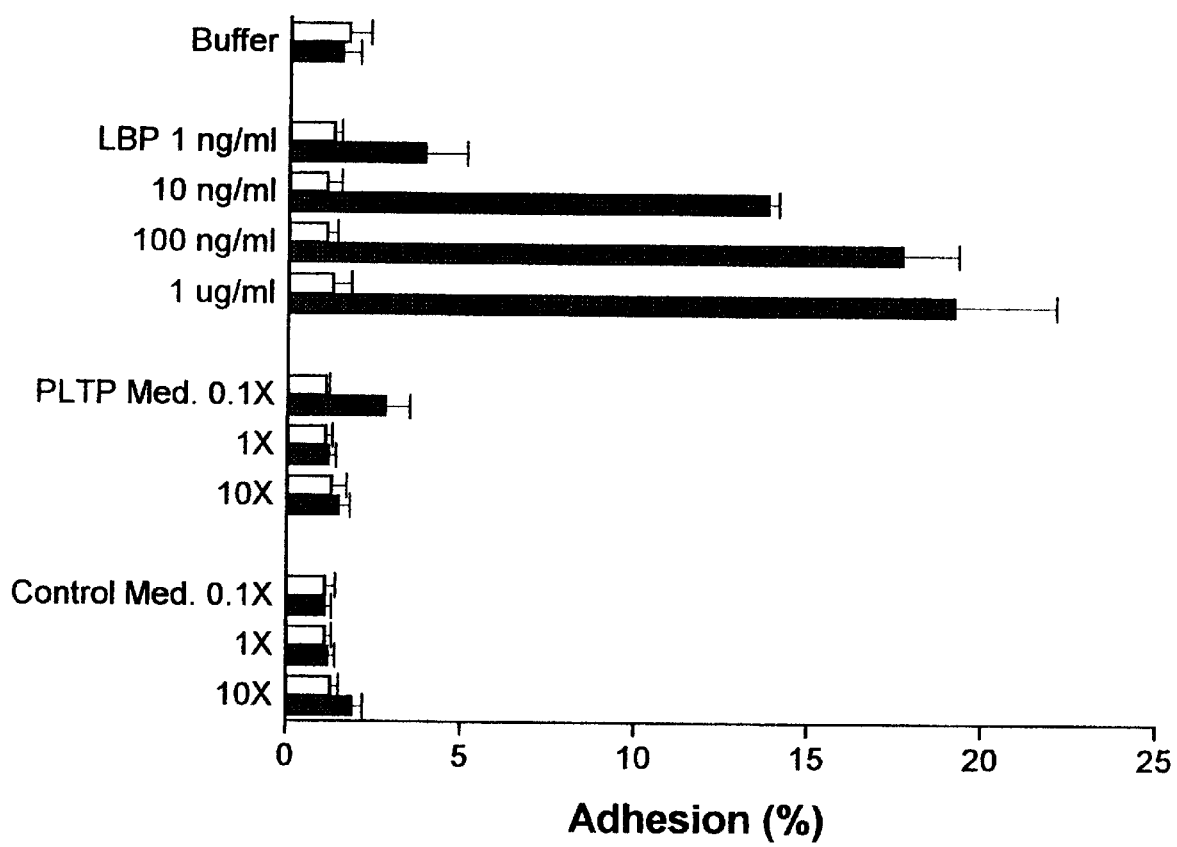

FIG. 28. rPLTP medium does not mediate stimulation of PMN by LPS. PMN were incubated for 10 min. at 37° C. in buffer alone (open bars) or with LPS (10 ng/ml) (filled bars) with the indicated concentrations of LBP, rPLTP medium or control medium. PMN were washed and adhesion to fibrinogen was measured. Each point represents the mean of triplicate determinations, ±S.D.

Figure 29:
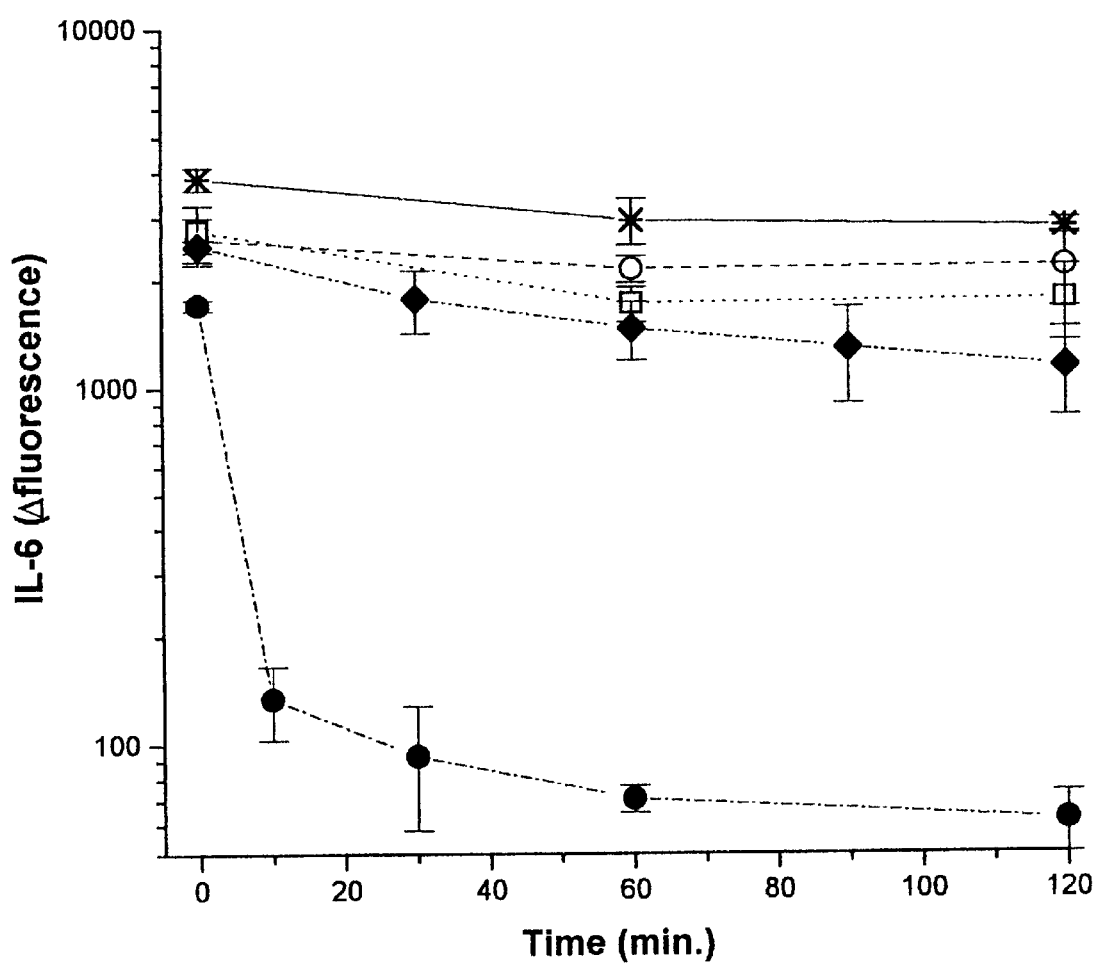

FIG. 29. rPLTP medium does not mediate neutralization of LPS-sCD14 complexes. LPS-sCD14 complexes were prepared as described in Experimental Procedures, and incubated at a final concentration of 10 ng/ml LPS and 1 μg/ml sCD14 for the indicated times alone (γ), with LBP (1 μg/ml) (○), with R-HDL (100 μg/ml) (□), with LBP and R-HDL (●), or with rPLTP medium and R-HDL (♦). Biologically active LPS was assessed by measuring IL-6 production in whole blood as in FIG. 24.

Figure 30:
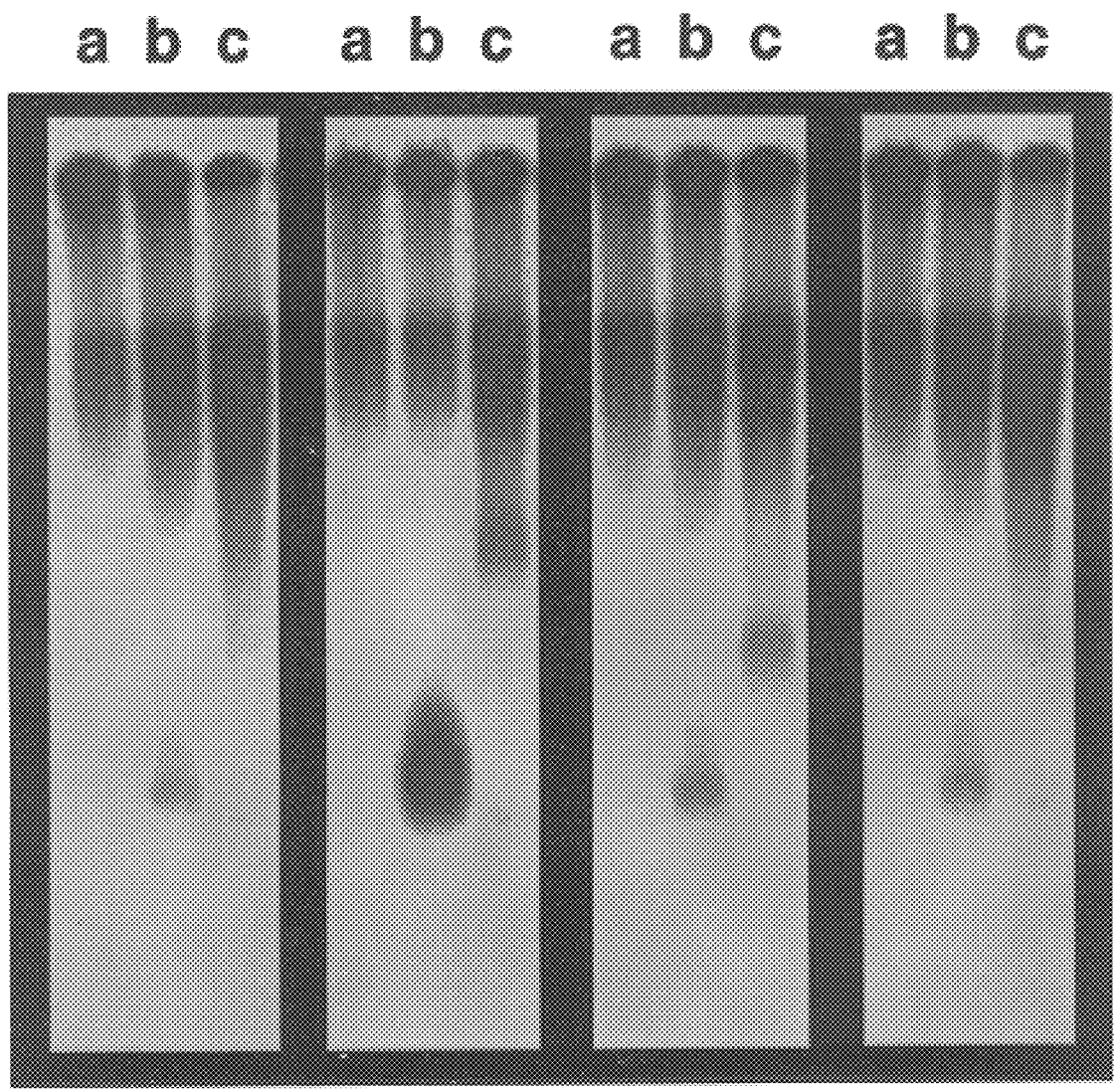

FIG. 30. Purified PLTP mediates transfer of $^3$H-LPS to R-HDL but not to sCD14. $^3$H-LPS (2 μg/ml) was incubated for 2 h at 37° C. with sCD14 (10 μg/ml) (lanes b) or R-HDL (100 μg/ml) (lanes c), in the presence of LBP (1 μg/ml) (lanes 4–6) or purified PLTP (lanes 7–9). Samples were subjected to native PAGE and $^3$H-LPS was visualized by fluorography.

DETAILED DESCRIPTION OF THE INVENTION

As noted above, the present invention is directed to compositions comprising lipoprotein particles that contain a lipid exchange protein for neutralizing lipopolysaccharide activity in vitro or in vivo.

As the invention relates in part to conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984).

Therefore, if appearing herein, the following terms shall have the definitions set out below.

A composition comprising "A" (where "A" is a single molecule, such as a protein, phospholipid, cholesterol, or a defined homogenous composition of such components) is substantially free of "B" (where "B" comprises one or more contaminating proteins, phospholipid molecules, etc.) when at least about 75% by weight of the composition is "A". Preferably, "A" comprises at least about 90% by weight of the A+B species in the composition, most preferably at least about 99% by weight. It is also preferred that a composition, which is substantially free of contamination, contain only a single molecular weight species of each of the defined components having the activity or characteristic of interest.

The term "homogeneous" as used herein refers to a defined composition of particles, in which each particle is made up of approximately the same proportion of individual components. Thus, in a homogenous composition of particles comprising phospholipids and a lipid exchange protein, each particle has approximately the same proportion of phospholipid or phospholipids and lipid exchange protein. Such particles are distinguished from naturally occurring particles, which have varying amounts of components, including, usually, proteins and phospholipids. The term "homogeneous" as used herein also refers to defined mixtures, in which more than one population of particles having substantially identical compositions are present. For example, a "composition of homogeneous particles" of the invention may contain particles of phosphatidylcholine/phophatidylinositol/lipid exchange protein and particles of phosphatidylcholine/cholesterol/lipid exchange protein. Such a composition, while not strictly homogenous, is nevertheless well defined.

The term "particle," when used in reference to the compositions of the invention, refers to a lipid bilayer vesicle or mixed micelle containing phospholipids, a lipid exchange protein, and any other components that might be present. It is well understood in the art that at a critical concentration, phospholipids spontaneously form such particles, which are energetically favored since the polar head group of the phospholipid extends into the aqueous solution, and the non-polar acyl chain locates in the interior of the mixed micelle or vesicle bilayer. The term "mixed micelle" refers to a micelle comprising one or more phospholipids and a lipid exchange protein as defined herein.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Various abbreviations are used herein, including: HAP, Dulbecco's PBS with 0.5 U/ml aprotinin, 0.05% human serum albumin, 3 mM D-glucose; PD, Dulbecco's PBS lacking $Ca^{2+}$ and $Mg^{2+}$; PD EDTA, Dulbecco's PBS lacking $Ca^{2+}$ and $Mg^{2+}$ with 1 mM EDTA; NHP, Normal Human Plasma; ELPS, LPS coated sheep erythrocyte; LBP, human lipopolysaccharide binding protein (a lower case "r" indicates that the protein is produced recombinantly); PLTP, phospholipid transfer protein; HDL, high-density lipoprotein; R-HDL, reconstituted high density lipoprotein; PC, phosphatidylcholine.

The present invention is based in part, on the results of studies of the functional neutralization of LPS by native and reconstituted HDL (R-HDL) using a rapid assay that measures the CD14-dependent activation of leukocyte integrins on human neutrophils. These studies demonstrated that reconstituted HDL particles (R-HDL), prepared from purified apolipoprotein A-I combined with phospholipid and free cholesterol, are not sufficient to neutralize the biologic activity of LPS, but that addition of recombinant LPS binding protein (LBP), a protein known to transfer LPS to CD14 and enhance responses of cells to LPS, enabled prompt binding and neutralization of LPS by R-HDL. Similarly, rPLTP strongly enhanced the rated of LPS neutralization by R-HDL, to an extent greater than that observed with rLBP. Thus, the invention is based in part on the unexpected observation that PLTP and LBP appear capable of transferring LPS to lipoprotein particles. It has also been found that the presence of soluble CD14 greatly accelerates LBP-mediated transfer of LPS to R-HDLs; soluble CD14 has no effect on PLTP-mediated transfer of LPS.

The invention is further based on the observation that, in contrast with R-HDL, apolipoprotein A-I containing lipoproteins (LpA-I) isolated from plasma by selected affinity immunosorption (SAIS) on an anti-apoA-I column neutralized LPS without addition of exogenous LBP. Several lines of evidence disclosed herein demonstrated that LBP is a constituent of LpA-I in plasma. Passage of plasma over an anti-apoA-I column removed more than 99% of the LBP detectable by ELISA, while 31% of the LBP was recovered by elution of the column. Similarly, the ability of plasma to enable activation of neutrophils by LPS (LBP/Septin activity) was depleted and recovered by the same process. Furthermore, an immobilized anti-LBP monoclonal antibody co-precipitated apoA-I. The results described here suggest that in addition to its ability to transfer LPS to CD14, LBP associated with HDL particles may also transfer LPS to lipoproteins. Since LBP appears to be physically associable with lipoproteins, and this association is stable in plasma, such complexes are positioned to play an important role in the neutralization of LPS.

The invention is further based on observations disclosed herein that LBP catalyzes transfer of LPS from soluble CD14 (sCD14) to R-HDL; that sCD14 accelerates neutralization of LPS by LBP and R-HDL; that phospholipids, not apolipoprotein, are required for LBP-dependent binding and neutralization of LPS; that sCD14 binds phospholipids; that neutralization of LPS by LBP associated with phospholipids depends on acyl chain length; that LBP associated with different lipids neutralizes LPS to differing degrees; and that acute phase plasma exhibits enhance neutralization of LPS.

Lipoprotein Compositions

As noted above, the compositions of the invention comprise a lipid exchange protein that is capable of mediating transfer of LPS into a phospholipid or lipoprotein particle.

The terms "lipid (or phospholipid) exchange protein" and "lipid (or phospholipid) transfer protein" as used herein are equivalent, and refer to a protein that mediates transfer of LPS from vesicles or micelles to lipoprotein particles. Accordingly, hereinafter such proteins are specifically referred to as "LPS exchange proteins" to differentiate them from lipid exchange (or transfer) proteins that cannot act on LPS. In a particular aspect, the LPS exchange proteins of the invention act catalytically, in that one protein can mediate the transfer of more than one molecule of LPS into the lipoprotein particles. Such proteins can be obtained from natural sources, or by recombinant technology.

Although not intending to be bound by any particular theory, such a protein may operate by exchanging a phospholipid from the particle with which it is associated for LPS. As shown in the examples, infra, the LPS can be found in an LPS micelle or vesicle, or it can be associated with CD14 (either soluble or membrane associated). In a specific example, infra, it was observed that phosphatidylinositol is favored for exchange of LPS associated with soluble CD14 into phospholipid-LPS exchange protein particles.

It is a great advantage of the present invention that it provides for exchange of LPS associated with CD14. This exchange reaction provides for neutralizing the activity of LPS after it has associated with its receptor, as well as neutralizing "free" LPS found in vesicles or micelles.

In a preferred embodiment, the LPS exchange protein is phospholipid transfer protein (PLTP; Day et al., 1994, J. Biol. Chem. 269:9388), or a fragment, analog, or derivative thereof that is functionally active. In another specific embodiment, the LPS exchange protein is LBP or lipid transfer protein (see, Wirtz, 1991, Annu. Rev. Biochem. 60:73), or a fragment, analog or derivative thereof that is functionally active. An LPS exchange or LPS transfer protein, or fragment, analog or derivative thereof, can be produced recombinantly (e.g., Hailman et al., 1994, J. Exp. Med. 179:269; Day et al., supra). The term "functionally active" refers specifically to the ability to mediate transfer of LPS into lipoprotein particles.

LPS exchange protein derivatives can be made by altering encoding nucleic acid sequences by substitutions, additions or deletions that provide for functionally equivalent molecules. Preferably, derivatives are made that have enhanced or increased functional activity relative to the native LPS exchange protein.

The LPS exchange protein derivatives of the invention include, but are not limited to, those containing, as a primary amino acid sequence, all or part of the amino acid sequence of a LPS exchange protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The genes encoding LPS exchange protein derivatives and analogs of the invention can be produced by various methods known in the art. The manipulations which result in their production can occur at the gene or protein level. For example, the cloned LPS exchange protein gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of an LPS exchange protein, care should be taken to ensure that the modified gene remains within the same translational reading frame as the LPS exchange protein gene, uninterrupted by translational stop signals, in the gene region where the desired activity is encoded.

Additionally, the LPS exchange protein-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations enhance the functional activity of the mutated LPS exchange protein gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification,* H. Erlich, ed., Stockton Press, Chapter 6, pp. 61–70).

Various phospholipids, such as but not limited to, phosphatidyl choline, phosphatidyl inositol, phosphatidyl serine, phosphatidyl ethanolamine, diphosphatidyl glycerol, sphingomyelin, cerebroside, and ganglioside, can be used to prepare the phospholipid particles. Certain characteristics of the phospholipids enhance the ability of an LPS exchange protein, such as PLTP or LBP, to neutralize LPS. It has been found, for example, that phospholipid acyl chain lengths between about 8 and about 18 carbon atoms are preferred for lipid exchange mediated by LBP. It has also been found that for longer length acyl chains, e.g., greater than 14 carbon atoms in length, the presence of one or more unsaturated bonds, i.e., cis-double bonds, enhances the ability of LBP to neutralize LPS. Accordingly, the invention contemplates use of acyl chains greater than 18 carbon atoms in length, preferably having one, and more preferably having more than one, cis-double bond. One or a mixture of more than one phospholipids can be used to prepare a composition of the invention. Preferably, the choice of phospholipid or phospholipids optimizes the exchange reaction, resulting in a composition with high capacity to neutralize LPS.

In this regard, it has been found, as noted above, that phosphatidyl inositol (PI) appears to be a good substrate for LBP-mediated exchange. Thus, in a preferred embodiment, the phospholipid particle contains PI. More preferably, the particle contains PI and PC; the presence of PC stabilizes the particle.

Other agents for stabilizing the lipid-LPS exchange protein particle compositions include, but are not limited to, triglycerides; cholesterol, or derivatives and analogues thereof, such as cholesterol esters, that associate with lipid bilayers; and an amphipathic alpha-helical peptide-containing molecule.

As used herein, the term "amphipathic alpha-helical peptide-containing molecule" refers to a peptide, polypeptide, protein, or conjugates thereof (e.g., coupled to each other, to a short polymer, etc.) that has an amphipathic (i.e., amphiphilic) alpha-helical structure. Examples of such molecules, and their ability to interact with and stabilize lipid particles, are well known in the art (see, e.g., Cantor and Schimmel, *Biophysical Chemistry Part I: The conformation of biological macromolecules,* W. H. Freeman & Company: San Francisco, 1980, pp. 246–248; Darnell et al., *Molecular Cell Biology,* Scientific American Books: New York, 1986, pp. 578–584; each of these references is specifically incorporated herein). It is also known that the α-helical portions or domains of such proteins are sufficient to associate with lipids. Preferably, such amphipathic alpha-helical peptide-containing molecules are apolipoproteins, which are particularly designed to interact with lipids. Accordingly, examples of such molecules include, but are not limited to apo A-I, apo A-II, apo B, apo C-I, apo C-II, apo C-III, and apo E.

The term lipoprotein particle refers to high density lipoprotein (HDL) particles, low density lipoprotein (LDL) particles, and very low density lipoprotein (VLDL) particles. Such particles are characterized by the presence therein of lipoproteins, such as apolipoprotein (apo) A-I and or apo A-II (components of HDLs); phospholipids, such as phosphatidylcholine; and cholesterol (or derivatives or analogs thereof that bind to cell membranes). Apo A-I contains about 245 amino acid protein; Apo A-II is a homodimer of two about 77 amino acid proteins joined by a single disulfide bond.

In Vitro Uses of Compositions of the Invention

In a particular embodiment, the phospholipid-LPS exchange protein compositions of the invention that contain a LPS exchange protein can be used in vitro to reduce or eliminate the level of endotoxin in a solution. Reduction of the levels of endotoxin is extremely important for in vitro cell culture and fermentation. The presence of endotoxin in cell culture medium can spoil an experiment designed to measure activation of leukocytes or lymphocytes in response to a particular antigen, or can ruin an effort to propagate a particular line or clone of such cells. Accordingly, immunologists and cell culture technologists go to great lengths, and expense, to avoid or destroy endotoxin. Frequently, these efforts comprise measuring the level of endotoxin in a sample of culture medium or serum (e.g., fetal calf serum), and discarding lots that show endotoxin contamination. Other strategies include elimination of endotoxin by specific antibody adsorption, which is only partially effective. Thus, the invention advantageously provides for eliminating or reducing the level of endotoxin in cell culture fluid or components thereof.

Accordingly, the invention provides for adding a composition of the invention to cell culture medium at a concentration effective to neutralize LPS activity. Such a concentration can be readily determined used titration techniques, using, for example, an assay for LPS activity as an indicator. One assay for LPS activity, exemplified herein, comprises evaluating adhesion of PMS to fibrinogen-coated surfaces (van Kessel et al., 1994, J. Immunol. Meth.). Other assays for the presence of LPS, such as expression of TNF or other lymphokines, can also be used to titrate an in vitro dosage of a composition.

Similarly, the presence of endotoxin in recombinant proteins produced by gram-positive bacteria, most commonly *E. coli,* render these preparations unsuitable for therapeutic use in humans and other mammals. Accordingly, the invention provides for neutralizing endotoxin contaminants from these sources, thus rendering recombinantly produced proteins safe for use in humans and animals. A further advantage of the invention is that the LPS-laden phospholipid or lipoprotein particles are readily removed from the recombinantly expressed protein by simple size exclusion chromatography, since there is a vast size difference between such particles and a protein.

Furthermore, lipoprotein particles are fairly inactive, and would not be expected to mediate substantial adverse side effects in culture or if used in compositions administered to a subject.

Therapeutic Methods

The present invention contemplates methods of treating and/or preventing one or more of the symptoms of endotoxin-mediated sepsis, particularly those associated with a transient increase in the blood level of TNF, such as fever, hypotension, neutropenia, leukopenia, thrombocytopenia, shock and multiple organ failure. Patients in need of such treatment include those at risk for or believed to be suffering endotoxemia resulting from a gram-negative bacterial infection. Patients particularly able to benefit from the present invention are those suffering infection by *E. coli,* salmonella, and the like. Patients at particularly at risk for sepsis include those suffering burns, gunshot wounds, renal or hepatic failure due to chemical poisoning or abuse, immunocompromised individuals such as AIDS patients, and the like. Preferably, the compositions of the invention are prepared in an admixture with a pharmaceutically acceptable carrier.

As used herein, the term "endotoxemia" refers to a condition in which endotoxins (LPS particles or molecules) are present in a subject at levels capable of inducing specific responses. Generally, endotoxemia is associated with a gram-negative bacterial infection.

The term "gram-negative" bacterial infection refers to a local or systemic infection with gram-negative bacteria, such as, but not limited to, *E. coli* and salmonella.

The term "endotoxin-mediated sepsis" refers to sepsis associated with increased levels of endotoxin, or gram-negative infection. The term "sepsis" is defined in the BACKGROUND OF THE INVENTION.

The compositions of the invention, in particular a pharmaceutical composition of the invention, or the administration of such a composition, can be used to protect or treat an animal subject, in particular a mammalian subject, believed to be suffering from endotoxemia, sepsis, or septic shock. Thus, a composition of the invention can be used in birds, such as chickens, turkeys, and pets; in mammals, preferably a human, although the compositions of the invention are contemplated for use in other mammalian species, including but not limited to domesticated animals (canine and feline); farm animals (bovine, ovine, equine, caprine, porcine, and the like); rodents; and undomesticated animals.

Since it is not always feasible or practical to confirm that sepsis is due to endotoxin or a gram-negative bacterial infection, the administration of a composition of the invention is indicated for the treatment of a subject suspected of suffering from endotoxemia, endotoxin-mediated sepsis, or a gram-negative infection. It is particularly advantageous that the compositions of the invention, i.e., lipoprotein particles, are not highly active on their own. Thus, such compositions are believed to be safe for prophylactic administration even if a gram-negative infection is not confirmed.

Thus, according to the invention, the compositions can advantageously be used prophylactically, to head off endotoxemia in those patients particularly at risk for developing sepsis.

The actual dosage of a composition of the invention for prophylaxis or treatment with depend on many factors, such as the potential for or stage of infection, severity of sepsis, overall health of the subject, age of the subject, size and weight of the subject, etc. It is well within the skill of the ordinary physician to determine a therapeutically effective dose based on evaluation of these parameters.

It is a particular advantage of the invention that the lipoprotein-LPS exchange protein compositions can reflect the natural components of a subject, thus reducing the probability of generating a neutralizing or allergic immune response.

Diagnostic Methods

As noted above, the invention provides a method for diagnosis, monitoring, or prognosis of a subject believed to be suffering from gram-negative or endotoxinmediated sepsis. In general, the methods of diagnosis, monitoring, or prognosis involve detecting or measuring the level of LPS exchange proteins associated with lipoproteins in a biological sample from a subject, and comparing the level so measured with a level measured in the subject at an earlier time, or with the level found in normals, wherein in a specific example, a moderate increase in the level is indicative of endotoxemia, and a large increase is indicative of acute phase.

The detection or measuring can comprise determining the capacity of a biological fluid, e.g., plasma or serum, from a subject to neutralize LPS activity. LPS activity can be evaluated using any method known in the art, including the methods discussed above, e.g., adherence of PMN, induction of expression of TNF or IL-1, etc. In a specific example, infra, greatly increased capacity of plasma to neutralize LPS activity is associated with acute phase of septic shock. Accordingly, the invention specifically provides an assay for diagnosing acute phase of septic shock. In another embodiment, a moderate increase in the capacity of plasma to neutralize LPS was associated with endotoxemia. In particular, normal volunteers were injected with LPS, and plasma drawn from the volunteers six hours after injection with LPS had increase LPS neutralizing activity as compared with plasma drawn before the exposure to LPS.

Alternatively, detection according to the invention can be assayed by immunoassay. For example, antibodies reactive with a component of the lipoprotein or the LPS exchange protein, or both, can be prepared and optionally labeled, such as with an enzyme, a compound that fluoresces and/or a radioactive element, and may then be introduced into a biological sample from a mammal believed to be suffering form endotoxin-mediated sepsis. After the labeled material has had an opportunity to react with antigens that may be present in the sample under conditions that allow binding to occur, the resulting mixture may be examined by known techniques, which may vary with the nature of the label attached, for evidence of binding.

These general procedures and their application are all familiar to those skilled in the art and are presented herein as illustrative and not restrictive of procedures that may be utilized within the scope of the present invention. An immunoassay procedure analogous to a "competitive" procedure is described in U.S. Pat. Nos. 3,654,090 and 3,850,752. An immunoassay analogous to a "sandwich" procedure, is described in U.S. Pat. Nos. RE 31,006 and 4,016,043.

According to the invention, antibodies which recognize the LPS exchange protein and lipoprotein particle can be obtained from commercial or other sources, or can be prepared. Such antibodies include but are not limited to polyclonal, monoclonal, chimeric, single chain, Fab fragments, and an Fab expression library. Accordingly, as used herein, the term "antibody" broadly relates to immunoglobulin or antigen-binding fragments thereof, e.g., as described above.

Various procedures known in the art may be used for the production of polyclonal antibodies. For the production of antibody, various host animals can be immunized by injection with the antigen, including but not limited to rabbits, mice, rats, etc. In one embodiment, a LPS exchange protein or a component of a lipoprotein particle can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies, any technique which provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96).

According to the invention, techniques described for the production of single chain antibodies (U.S. Pat. No. 4,946, 778) can be adapted to produce antibodies. An additional embodiment of the invention utilizes the techniques described for the construction of Fab expression libraries (Huse et al., 1989, Science 246:1275–1281) to allow rapid and easy identification of monoclonal Fab fragments with the desired specificity.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

The foregoing antibodies can be used in methods known in the art relating to the detection and measuring the level of LPS exchange protein or lipoprotein particles, e.g., for Western blotting, imaging PTP, measuring levels thereof in appropriate physiological samples, etc.

Generally, an antibody will be detectably labelled. The labels most commonly employed for these studies are radioactive elements, enzymes, chemicals which fluoresce when exposed to ultraviolet light, and others.

Suitable radioactive elements may be selected from the group consisting of $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re. In the instance where a radioactive label, such as one of the isotopes listed above, is used, known currently available counting procedures may be utilized to detect or quantitate the amount of label, and thus the amount of material bound.

In the instance where the label is an enzyme, detection may be accomplished by any of the presently utilized colorimetric, spectrophotometric, fluorospectrophotometric, thermometric, amperometric or gasometric techniques known in the art. The enzyme may be conjugated to the carbohydrate, by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase, hexokinase plus GDPase, RNAse, glucose oxidase plus alkaline phosphatase, NAD oxidoreductase plus luciferase, phosphofructokinase plus phosphoenol pyruvate carboxylase, aspartate aminotransferase plus phosphoenol pyruvate decarboxylase, and alkaline phosphatase. U.S. Pat. Nos. 3,654,090; 3,850, 752; and 4,016,043 are referred to by way of example for their disclosure of alternative labeling material and methods.

A number of fluorescent materials are known and can be utilized as labels. These include, for example, fluorescein, rhodamine and auramine.

The present invention includes assay systems that may be prepared in the form of test kits for the quantitative analysis of the extent of the presence of LPS exchange proteins associated with lipoproteins. The system or test kit will comprise means for detecting the presence and amount of the LPS exchange protein and the lipoprotein in a sample. Optionally, a test kit may also comprise instructions, enzyme substrates, and other reagents. In a specific embodiment, a kit of the invention may include a known amount of a composition of the invention as a standard.

In accordance with the testing techniques discussed above, one class of such kits will contain at means for detecting binding of antibodies to the LPS exchange protein and to a component of the lipoprotein, and may include directions, depending upon the method selected. The kits may also contain peripheral reagents such as buffers, stabilizers, etc.

Another such class of test kits will contain reagents necessary to measure the capacity of plasma to neutralize LPS. For example, such a test kit may contain an known amount of LPS, and means for measuring the level of LPS in a sample, e.g., reagents for a PMN adherence assay, or antibodies for detecting TNF or IL-1, etc. Preferably, such a test kit will contain a known amount of a composition of the invention to provide a standard.

As used herein, the term "diagnosis" refers to a medical conclusion concerning the cause of a disease or disorder, which is based on a totality of the symptoms and relevant indicators. According to the invention, changes in the level of LBP associated with lipoproteins, e.g., as measured by the capacity of plasma to neutralize LPS, may be associated with endotoxin-mediated sepsis. Thus, as noted above and in an Example, infra, the invention provides for diagnosing endotoxemia, sepsis, and septic shock.

The term "monitoring" refers to evaluating the condition of a subject undergoing treatment, whether the treatment involves administration of a composition of the invention or another treatment for gram-negative sepsis. The present invention contemplates that changes in the level of LBP associated with lipoproteins, in particular HDL particles, may be associated with treatment for endotoxin-mediated sepsis or septic shock.

The term "prognosis" refers to predicting the outcome or course of a disease or disorder. According to the present invention, the prognosis is of the outcome of sepsis or septic shock, e.g., the probability that the subject believed to be suffering from gram-negative infection or endotoxin mediated sepsis will recover. In particular, prognosis may involve measuring the level of lipoprotein particles that contain a LPS exchange protein that is characterized by being capable of facilitating an exchange of lipopolysaccharide into the high density lipoprotein particles; and comparing the level measured in step (a) with a level in the patient at an earlier time, wherein an increase in the level indicates greater probability of a positive outcome of the sepsis.

In a specific embodiment, measuring the level of HDL particles that contain LBP comprises detecting a proportion of lipoprotein particles containing apolipoprotein A-I that also contain lipopolysaccharide binding protein. For example, a sandwich immunoassay, using an anti-apo A-I antibody as a capture reagent and an anti-LBP antibody as a detection reagent, can be performed. Alternatively, an anti-IBP antibody can be used as the capture reagent, and an anti-apo A-I antibody can be used as the detection reagent. In a specific example, infra, the presence of LBP is detected by ELISA of Lp(A-I) particles eluted from an anti-apoA-I column. In another specific example, infra, the association of LBP with HDLs is detected by a sandwich ELISA using a solid phase adsorbed monoclonal anti-LBP antibody 17G4, and the presence of Lp(A-I) is detected with a polyclonal anti-apoA-I.

The present invention will be better understood from a review of the following illustrative description presenting the details of the constructs and procedures that were followed in its development and validation.

EXAMPLE 1

LBP-Lipoprotein Complexes Neutralize LPS

The present Example demonstrates that reconstituted HDL particles that contain LBP, as well as LpA-I particles isolated from plasma, which contain LBP, neutralize LPS.

Materials and Methods

Reagents. LPS from *Salmonella minnesota* strain R595 (Re) and $^3$H-labelled LPS from *E. coli* K12 strain LCD25 (K12) was purchased from List Biological Laboratories (Campbell, Calif.). Human serum albumin was purchased from Armour Pharmaceutical Company (Kankakee, Ill.). Recombinant human lipopolysaccharide binding protein (rLBP) was expressed and purified as described (Hailman et al., 1994, J. Exp. Med. 179:269). Polyclonal anti-rLBP was raised in rabbits and purified by chromatography on Protein G Sepharose. 17G4 is a murine monoclonal antibody (IgG2a) directed against LBP. It was purified from ascites fluid by chromatography on Protein G Sepharose. Purified egg phosphatidylcholine, cholesterol and sodium cholate were purchased from Sigma Chemical Co. (St. Louis, Mo.). Normal human plasma (NHP) was prepared from the blood of healthy donors anti-coagulated with 5 U/ml sodium heparin and stored at 4° C.

Depletion of apolipoprotein A-I from NHP. NHP was depleted of apolipoprotein A-I (apoA-I) using selected affinity immunosorption (SAIS) as previously described (McVicar et al., 1984, Proc. Natl. Acad. Sci. USA 81:1356; Kunitake et al., 1990, Arteriosclerosis 10:25). NHP passed through a column of sepharose coupled to a goat anti-human apoA-I IgG was shown to be greater than 95% depleted of apoA-I by ELISA. Recovery of apoA-I from the column by elution with 0.2M acetic acid, 150 mM NaCl (pH 3.0) was greater than 90%. The resulting preparation of apoA-I containing lipoproteins (Lp(A-I)) has been characterized previously (McVicar et al., supra). As a control, NHP was passed over a pre-immune IgG column and showed no detectable loss of apoA-I from the flow through and no recovery of apoA-I in the acid eluate. The goat anti-human apoA-I antibody used to prepare the immunoaffinity column was shown not to recognize LBP by ELISA (see FIG. 10) or western blot (data not shown).

Preparation of reconstituted HDL particles. R-HDL were prepared by the sodium cholate dialysis method as previously described (Matz et al., 1982, J. Biol. Chem. 257(8) :4535). Briefly, apoA-I, purified by sequential ultracentrifugation and size exclusion chromatography as previously described (Weisweiler, 1987, Clin. Chim. Acta 169:249) was mixed with egg phosphatidylcholine (PC), cholesterol and cholate at a ratio of 80:4:1:80 (PC:cholesterol:apoA-I:cholate) and cholate was removed with extensive dialysis against PD EDTA (Dulbecco's PBS lacking $Ca^{2+}$ and $Mg^{2+}$ with 1 mM EDTA) containing 0.01% sodium azide. Another mixture was prepared in parallel in which PC and cholesterol were omitted (apoA-I alone). Incorporation of apoA-I protein into lipid-containing particles of approximately 200 kd MW was confirmed by gel filtration using a Pharmacia superose 6 column (60 cm×1.8 cm) and by non-denaturing polyacrylamide gel electrophoresis using an 8–25% gel run on the Pharmacia Phast System. Final preparations were stored in PDEDTA with 0.01% azide at 4° C. Immediately prior to use in assays of the bioactivity of LPS, the apoA-I preparations were exchanged into APBS (PBS with 0.5% human serum albumin) by ultrafiltration in a Centricon 10 (Amicon, Beverly, Mass.). ELISA for quantitation of LBP. A 72 well Terasaki plate (Robbins Scientific Corp., Sunnyvale, Calif.) was coated with anti-LBP mAb 17G4 (5 µg/ml) then blocked with PD (Dulbecco's PBS lacking $Ca^{2+}$ or $Mg^{2+}$) containing 10% non-fat milk. The plate was then washed with PD containing Tween 20 (0.05%) and samples, diluted in PD containing 0.1% non-fat milk, were added to the plate for 1 hour at room temperature. The plate was then washed and rabbit anti-human rLBP (5 µg/ml in PD with 0.1% non-fat milk) was added for 1 hour at room temperature. The plate was washed again and alkaline phosphatase-conjugated goat anti-rabbit IgG (Bio-Rad, Richmond Calif.) (1:1500 in PD with 0.1% non-fat milk) was added to the wells. After a further 35-minute incubation at room temperature, the plate was washed and bound alkaline phosphatase was measured using the fluorogenic substrate Attophos (JBL scientific, San Luis Obispo, Calif.) and a Cytofluor 2300 (Millipore Corp.) fluorescence plate reader. Each plate included a standard curve of known concentrations of rLBP diluted in PD with 0.1% milk.

To observe the interaction of LBP with apoA-I, Terasaki wells were coated with 5 µg/ml of mAb 17G4, a mAb directed against human apoA-I, type II (Calbiochem), or control mAb 26 ic directed against CD14 (Todd et al., 1982, Hybridoma 1:329) for 2 hours at 21° C. Plates were blocked with 0.5% gelatin as described (Marcel et al., 1990, J. Clin. Invest. 85:10), and dilutions of rLBP, purified apoA-I, or partially purified lipoproteins were added for 30 min at 21° C. Plates were then washed and incubated with either goat anti-apoA-I (10 µg/ml) or with a rabbit anti-LBP (10 µg/ml). Bound secondary antibody was detected with alkaline phosphatase-conjugated anti-goat (Bio-Rad) or anti-rabbit IgG as described above.

Partially purified lipoproteins were obtained by passing NHP over a column loaded with HiPak™ aldehyde (Chromatochem, Misoula, Mo.). This procedure quantitatively removed LBP/Septin activity from NHP. The column was eluted with 0.5 M ammonium acetate pH 3.0, and the eluate was immediately applied to a G-25 Sephadex column to change the buffer to PDEDTA. This eluate contained 90% of the original LBP/Septin activity of plasma but less than 1% of the protein of plasma.

Stimulation of PMN by LPS. To assess the biologic activity of LPS adhesion of human PMN to fibrinogen-coated surfaces was measured (see, van Kessel et al., 1994, J. Immunol. Methods). In this assay, stimulation of PMN adhesion depends on the binding of LPS to cell surface CD14 and requires LBP or Septin (LBP/Septin activity) to facilitate this binding. Adhesion of the stimulated PMN to fibrinogen is mediated by the leukocyte integrin CD11b/CD18 (CR3, Mac1).

Briefly, mixtures containing LPS and a source of LBP or Septin were diluted in APBS or AHPBS (APBS with 4 U/ml sodium heparin) to the concentrations indicated, yielding a final volume of 50 µl. 10 µl of freshly isolated PMN ($2 \times 10^7$ cells/ml in HAP (Dulbecco's PBS with 0.5 U/ml aprotinin, 0.05% human serum albumin, 3 mM D-glucose)) fluorescently labelled with 5-(and 6-) carboxyfluorescein diacetate, succinimidyl ester as described (Hailman et al., supra) were added and incubated for 10 minutes at 37° C. to stimulate the cells. PMN were then washed into HAP and added to a 72 well Terasaki plate pre-coated with fibrinogen. After 15 minutes at 37° C., adherence of PMN to the plate was quantitated. The fluorescence in each well was measured using a Cytofluor 2300 as a way of quantitating the total number of cells per well. The plate was then washed and the plate was read again. Binding is expressed as the percentage of cells remaining in the well after the washing step (% adhesion). Since stimulation of the PMN requires both LPS and LBP/septin (FIG. 1), assays performed in the presence of excess LBP measure the available concentration of LPS. In a similar fashion, assays performed in the presence of excess LPS measure the available concentration of LBP/Septin. Donor to donor variation in maximal responses (20–75% adhesion) prohibited averaging results of separate experiments, but the pattern of responses was nonetheless reproducible.

Neutralization of LPS. LPS was incubated with lipoprotein or NHP diluted in AHPBS for 0–2 hours at 37° C. The amount of available LPS remaining in the tube was assessed by adjusting the LBP concentration to 0.5–1.0 µg/ml, adding PMN, and measuring adhesion as described above.

Binding of LPS-coated erythrocytes to macrophages. The binding of LPS-coated sheep erythrocytes (ELPS), opsonized with plasma, by CD14 on cultured human macrophages was performed as described (Wright et al., 1989, J. Exp. Med. 170:1231). Briefly, ELPS were prepared by incubating 10 mg of sonicated LPS (R595) with $10^8$ sheep erythrocytes for 1 hour at 37° C. ELPS were washed extensively and resuspended to a concentration of $1 \times 10^8$ cells/ml in EDTA-$GVB^{2-}$ (5 mM veronal buffer, pH 7.5, with 150 mM NaCl, 0.1% gelatin, 1 mM EDTA). To determine the ability of NHP to promote the binding of ELPS to macrophages, equal volumes of ELPS and a 1:50 dilution of NHP in PDEDTA were incubated for the stated time at 37° C. The resulting opsonized ELPS were washed, resuspended in EDTA-$GVB^{2-}$, and $5 \times 10^5$ red cells were added to a monolayer of macrophages in a Terasaki well. After a 15 minute incubation at room temperature unbound ELPS were removed by inverting the plate for 10 minutes at room temperature and gently washing the monolayer. Binding of ELPS was evaluated by phase contrast microscopy and expressed as the attachment index, the number of erythrocytes bound per 100 macrophages.

Binding of $^3$H-labelled LPS to R-HDL. To measure binding of LPS to R-HDL, $^3$H-LPS (100 ng/ml, specific activity 1000 dpm/10 ng), R-HDL (100 µg/ml) and rLBP (0–10 mg/ml) were diluted in 1 ml of APBS and incubated at 37° C. for 1 hour. The solution was then cooled to 0° C., brought to a density of 1.12 g/ml with a saturated potassium bromide solution, placed in a 5 ml QUICK-SEAL™ tube (Beckman Instruments, Palo Alto, Calif.) and spun in a Vti 65.2 rotor (Beckman) at a temperature of 10° C. for 9 hours at 60,000 rpm. The contents of each tube were separated into equal top and bottom fractions and the amount of radioactivity in 1 ml of each fraction was evaluated by scintillation counting in 3 ml of READY SAFE™ (Beckman). Preliminary studies demonstrated that under similar conditions, greater than 90% of $^3$H phosphatidylcholine labelled R-HDL was found in the top half of the tube. ApoA-I protein detected by western blot, also migrated to the top of the tube under these conditions.

Results

Figure 1:
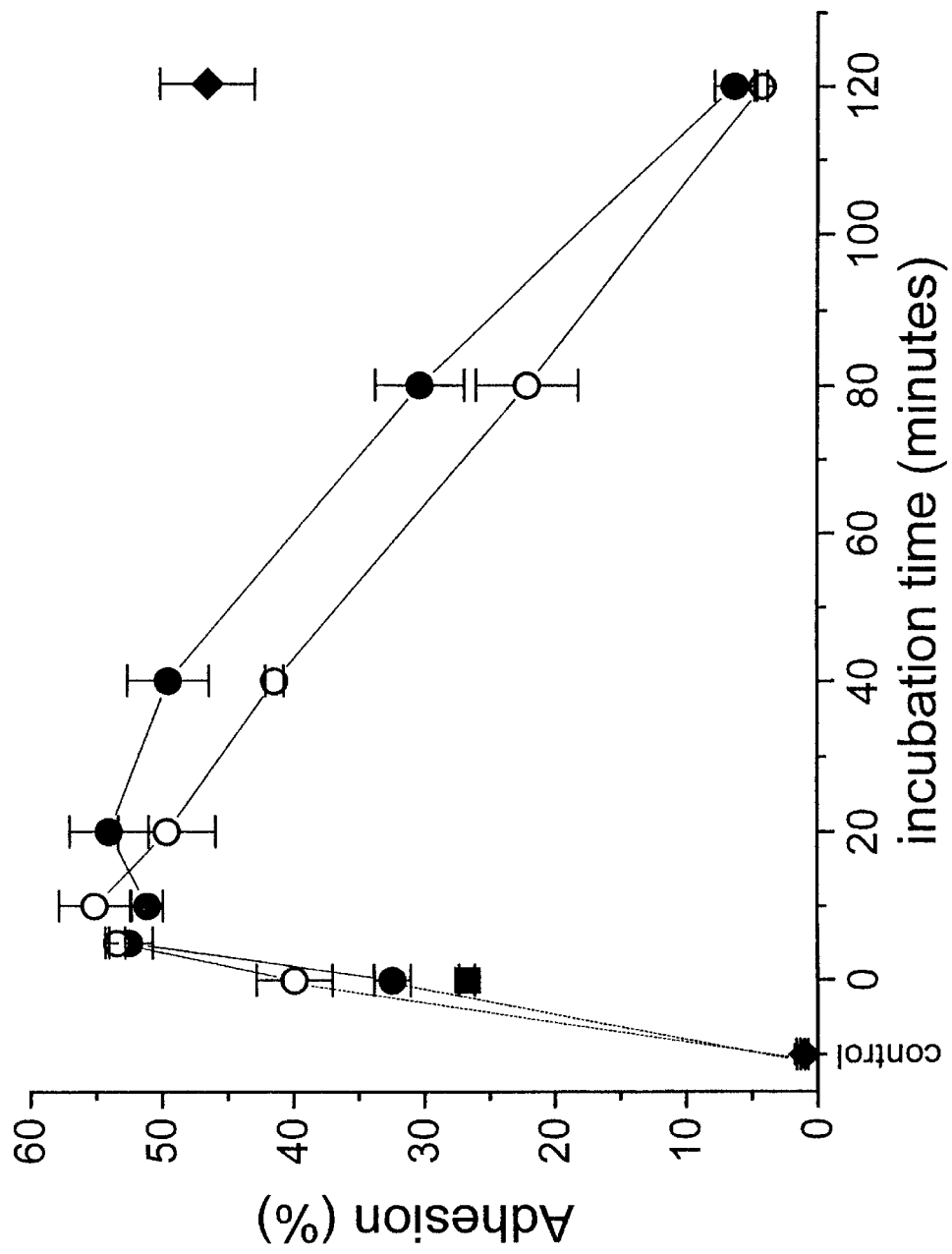
FIG. 1. NHP first potentiates then neutralizes the capacity of LPS to stimulate PMN. *E. coli* K12 LPS (1 ng/ml) was incubated for the stated intervals at 37° C. with NHP (10%) (●, ○). At the end of this period, buffer (●) or rLBP (1 μg/ml) (○) and fluorescently labelled PMN were added. After 10 minutes at 37° C. the binding of PMN to fibrinogen was measured as described in Materials and Methods. Fresh LPS (1 ng/ml) added after the 120 minute incubation with plasma (♦) restored cellular adhesion. rLBP (1 μg/ml) was sufficient to enable a response when mixed with LPS (1 ng/ml) just prior to addition of PMN (■). "Control" represents PMN treated with LPS alone (▽) or NHP alone (♦). Each point represents the mean of 3 wells +/− s.d. of a representative experiment repeated three times.

The ability of LPS to stimulate PMN is rapidly enhanced and then slowly neutralized upon incubation in NHP. LPS (1 ng/ml) was incubated with NHP (10%) at 37° C. for the intervals shown in FIG. 1. The ability of the resulting mixture to stimulate cells was quantitated by adding PMN for 10 minutes and measuring the attachment of the cells to immobilized fibrinogen. LPS alone did not stimulate adhesion of PMN to fibrinogen, but upon incubation of LPS with NHP, the ability of LPS to stimulate adhesion was very rapidly enabled (FIG. 1). Stimulation was evident even when LPS and NHP were combined immediately before the 10 minute incubation with PMN (0 minute incubation) and was maximal with a 10 min incubation. This rapid enabling effect may be attributed to LBP and/or Septin in the plasma and henceforth this activity, seen at the early time of incubation, is referred to as LBP/Septin activity.

Longer periods of incubation with NHP resulted in a gradual loss of the ability of LPS to stimulate PMN. After 120 minutes, more than 80% of the stimulatory capacity of the mixture was lost. The loss in activity over time was due to the loss of available LPS rather than the loss or degradation of LBP/Septin because addition of LPS at the end of the incubation restored responses while addition of rLBP did not (FIG. 1). Thus, the loss of the ability of LPS to stimulate cells after incubation in NHP results from neutralization of the LPS. Accordingly, the factor(s) responsible for this neutralization are termed LPS-neutralizing factor, or LNF. Because incubation of LPS in NHP for times longer than 120 minutes resulted in only minor additional loss of activity, 120 minutes was chosen as the standard time of incubation to demonstrate LNF activity.

Figure 2:
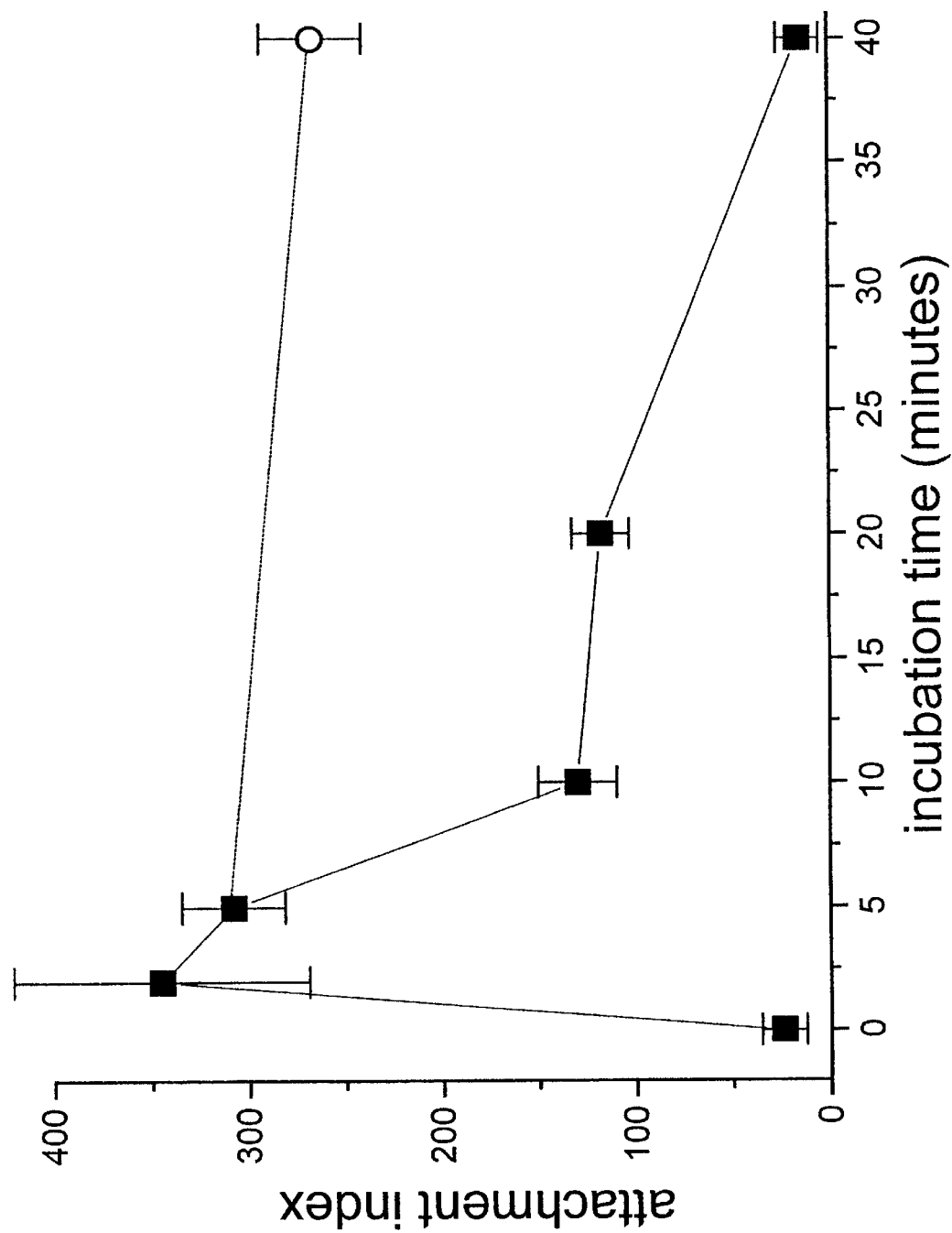
FIG. 2. NHP enables then inhibits the binding of ELPS to macrophages. ELPS were incubated for the stated period with NHP (2%) (■), washed into EDTAGVB$^{2-}$, added to a monolayer of macrophages, and binding of erythrocytes was evaluated as described in Materials and Methods. Data are expressed as attachment index, the number of erythrocytes bound per 100 macrophages, and are the mean values +/− s.d. for three wells of a representative experiment repeated 3 times. ELPS incubated with NHP 5 minutes, washed, and incubated another 35 minutes at 37° C. showed no decrease in binding to macrophages (○). In this experiment, ELPS in the absence of LBP or NHP gave an attachment index of 5.

The ability of plasma to transiently enable recognition of LPS by cells was confirmed in studies that measure the binding of LPS-coated erythrocytes (ELPS) to CD14 on macrophages. ELPS were incubated with 2% NHP for intervals, washed, and binding to macrophages was assessed (FIG. 2). Incubation of ELPS with plasma (5 minutes) enabled strong binding to macrophages, but further incubation caused complete loss of this binding capacity. This loss of binding was not due to the instability of LBP/Septin deposited on the ELPS surface because ELPS incubated with NHP for 5 minutes, washed to remove unbound protein, and incubated another 35 minutes at 37° C. retained the ability to bind macrophages. Furthermore, the reduction in binding observed after long incubation with NHP was not caused by loss of LBP/Septin activity because NHP recovered after the incubation with the ELPS retained the ability to promote binding of fresh ELPS to macrophages, and addition of fresh NHP or LBP to the treated ELPS did not restore binding to macrophages (data not shown). Finally, it is unlikely that the fall in binding was caused by loss of LPS from the erythrocyte since ELPS formed with $^3$H-labelled LPS demonstrated only a slow loss of less than 9% of the LPS between the 5 min and 40 min time points (data not shown). These results confirm that plasma contains activities that first enable recognition of LPS by cells and then cause neutralization of the LPS.

R-HDL does not bind or neutralize LPS. Several laboratories have demonstrated that LPS added to blood or plasma binds to lipoproteins such as HDL resulting in a complex with reduced biological activity (Skarnes et al., supra; Ulevitch et al., supra; Munford et al., supra; Flegel et al., supra). Therefore the role of HDL particles in the neutralization of LPS was evaluated. All HDL particles contain apoA-I, but these particles also contain substoichiometric amounts of at least 17 other proteins (Marcel et al., 1990, J. Clin. Invest. 85:10; Jordan-Starck et al., 1992, Curr. Op. Lipidology 3:75; Novotny et al., 1989, J. Biol. Chem. 264(31):18832; Stafforini et al., 1987, J. Biol. Chem. 262 (9):4215; Cheung et al., 1986, J. Lipid Res. 27(11):1135; Kunitake et al., 1992; Proc. Natl. Acad. Sci. USA 89:6993). To obtain a homogeneous preparation, HDL particles were reconstituted from purified apolipoprotein A-I (apoA-I), phosphatidylcholine and cholesterol.

Figure 3:
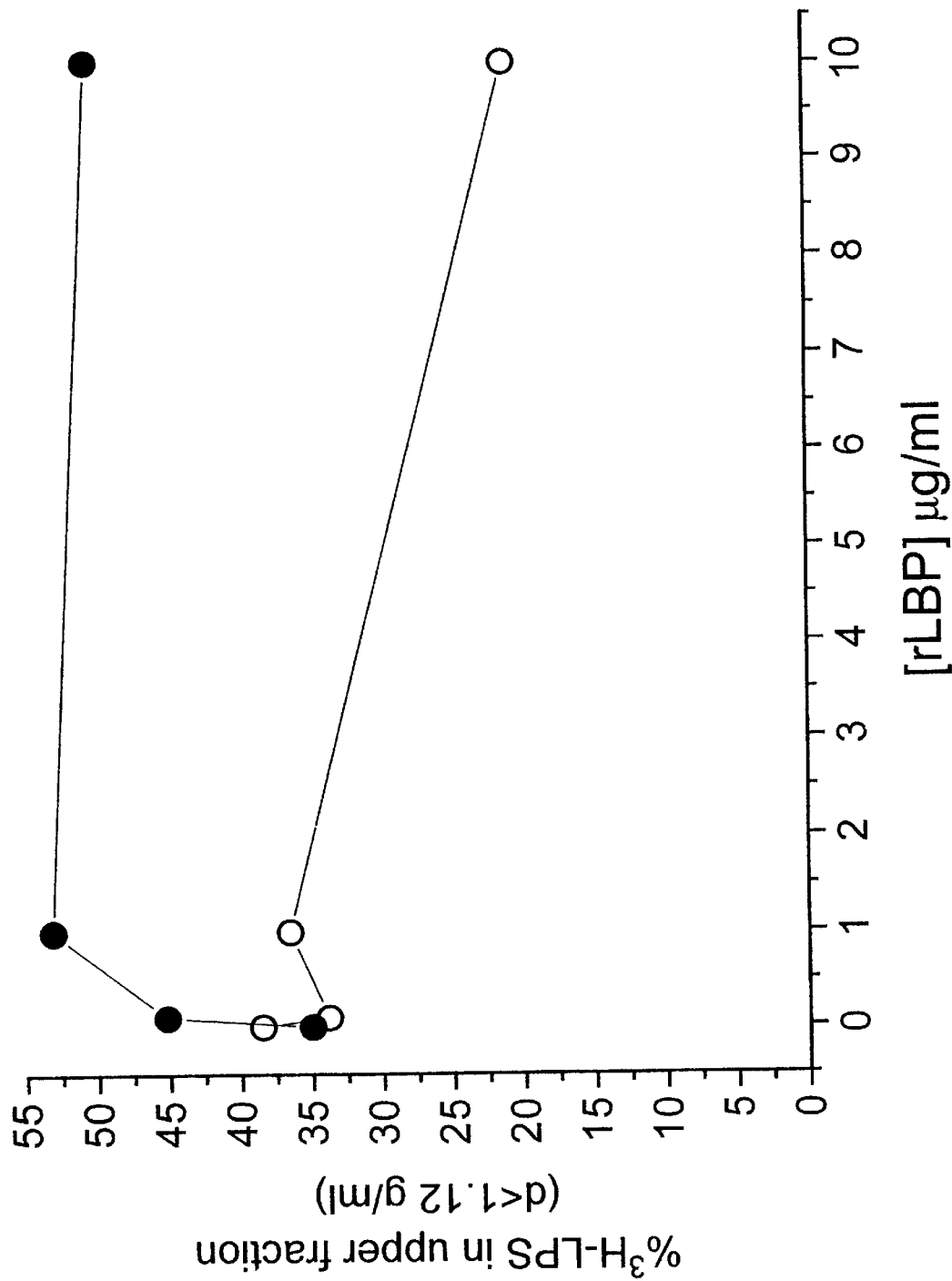
FIG. 3. Binding of LPS to R-HDL depends on the concentration of rLBP. $^3$H-LPS (100 ng/ml) was incubated with increasing concentrations of rLBP in the presence (●) or absence (○) of R-HDL (100 μg/ml) for 1 hour at 37° C. After ultracentrifugation at d=1.12 g/ml, the top and bottom half of each tube were separated and the amount of $^3$H-LPS assessed by scintillation counting. The data is presented as the CPM measured in the top half of each tube (d<1.12 g/ml) as a percentage of the total recovered in each tube. Results are representative of 2 identical studies and 3 similar studies using a fixed dose of LBP.
Figure 4:
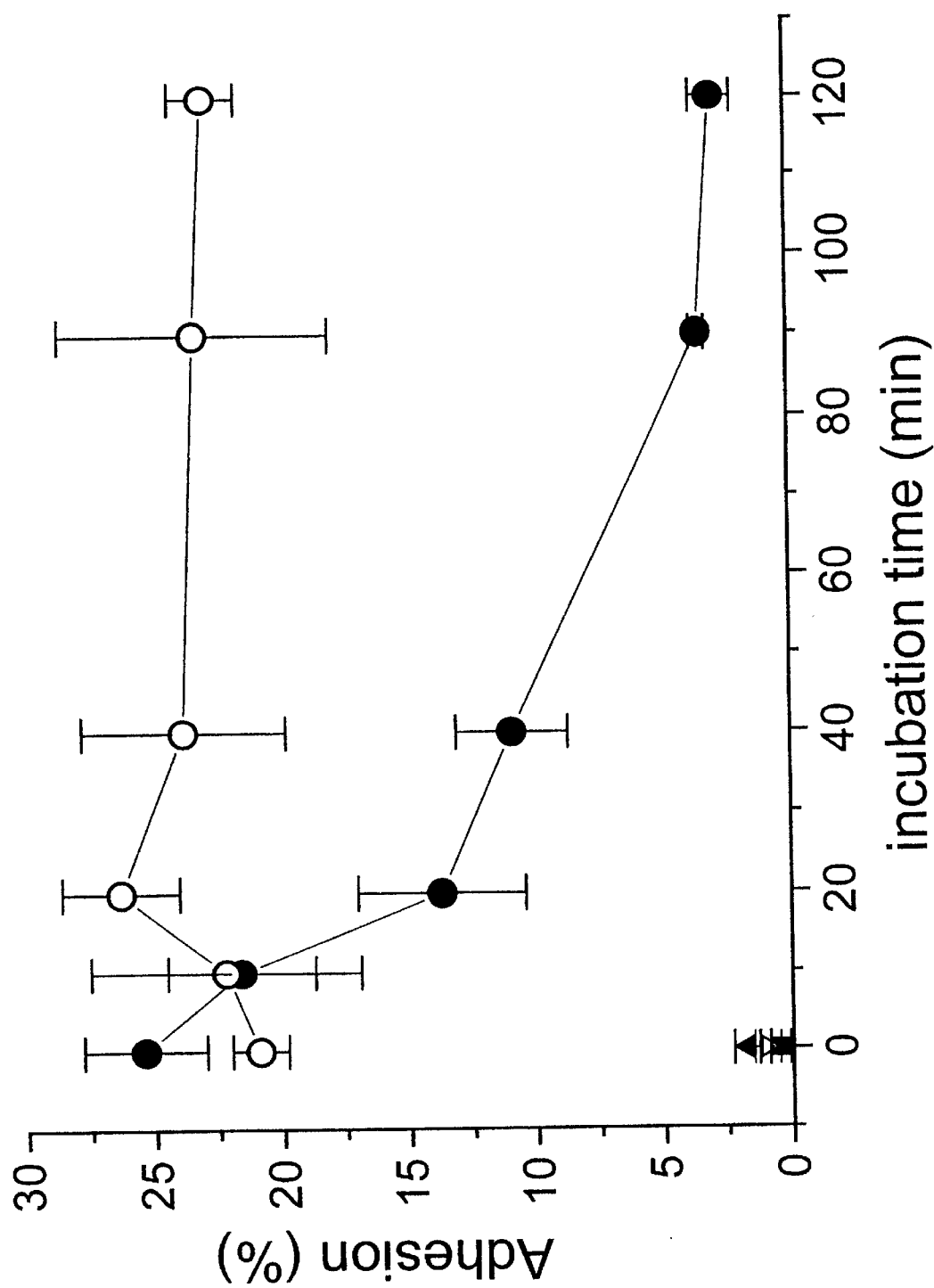
FIG. 4. Time dependence of the neutralization of LPS by R-HDL and rLBP. *E. coli* K12 LPS (1 ng/ml) was incubated with R-HDL (100 μg/ml apoA-I) for the stated times in the presence (●) or absence (○) of rLBP (0.5 mg/ml). The amount of biologically active LPS remaining was assessed by adjusting the LBP concentration of all samples to 0.5 μg/ml and adhesion of PMN to fibrinogen was measured. No stimulation of adhesion was seen with buffer alone (▽), LPS alone (▲), or LPS with R-HDL (■). Each point represents the mean of 3 wells +/− s.d of a representative experiment repeated 3 times.

Binding of LPS to lipoprotein was measured by incubating $^3$H-LPS with R-HDL for 1 hour at 37° C., followed by ultracentrifugation at a density of 1.12 g/ml to separate R-HDL (d<1.12 g/ml) from the relatively higher density $^3$H-LPS (FIG. 3). Addition of R-HDL caused no increase in the amount of $^3$H-LPS found at d<1.12 g/ml, indicating that no binding to R-HDL had occurred. In similar studies, LPS (1 ng/ml) was incubated with an amount of R-HDL approximating that found in 10% NHP (100 µg/ml), for times up to 2 hours, but no neutralization of biological activity was observed (FIG. 4). Thus, R-HDL by itself cannot bind or neutralize LPS.

rLBP enables R-HDL to rapidly bind and neutralize LPS. Previous studies have shown that LBP acts as an LPS transfer protein, catalyzing the binding of LPS to CD14 (Hailman et al., supra), which facilitates LPS activation of cellular responses. This study investigated the unlikely possibility that LBP may be able to transfer LPS into R-HDL and cause neutralization of the LPS. Indeed, we observed that LBP enabled a dose-dependent increase in the amount of $^3$H-LPS fractionating with R-HDL (FIG. 3). Association of $^3$H-LPS with R-HDL appeared maximal at an LBP concentration of 1 µg/ml. Under these conditions, approximately 30% of the $^3$H-LPS was shifted to the upper, HDL-containing fraction by the addition of LBP.

Figure 5:
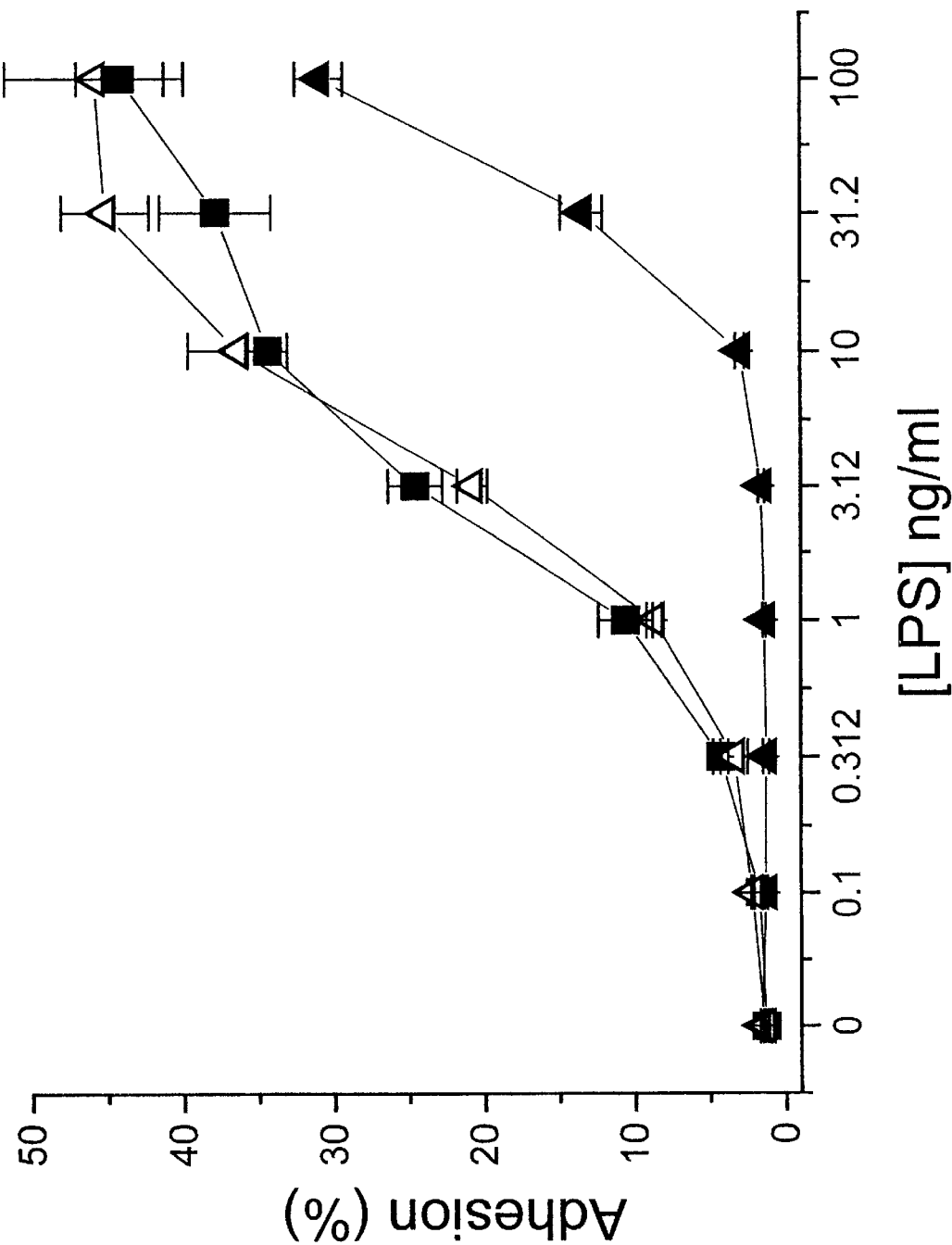
FIG. 5. LBP enables neutralization of high concentrations of LPS by R-HDL. Increasing concentrations of *E. coli* K12 LPS were incubated with buffer (■) or R-HDL (100 μg/ml apoA-I) (▲,△) in the presence (■, ▲) or absence (△) of rLBP (1 μg/ml) for 2 hours at 37° C. The amount of biologically active LPS remaining was assessed by adjusting the final rLBP concentration in all samples to 1 μg/ml, adding PMN and measuring binding to fibrinogen. Each point represents the mean of three wells +/− s.d. of a representative experiment repeated three times.

Parallel studies showed that LBP also enabled R-HDL to neutralize the biologic activity of LPS (FIG. 4). Neutralization of LPS by R-HDL and LBP was rapid and complete, with greater than 50% neutralization occurring in 40 minutes and >88% by 120 minutes. We confirmed the requirement for LBP in the neutralization of LPS by R-HDL using several concentrations of LPS (FIG. 5). Addition of 1 mg/ml rLBP enabled R-HDL to strongly neutralize >30 ng/ml LPS, but R-HDL in the absence of LBP caused no neutralization of LPS at any dose.

When the dose of LPS was adjusted to 100 ng/ml, LBP caused neutralization of approximately 30% of the biologic activity (FIG. 5). This fraction corresponds well to the 30% of $^3$H-LPS transferred to R-HDL under similar conditions (FIG. 3).

Figure 6:
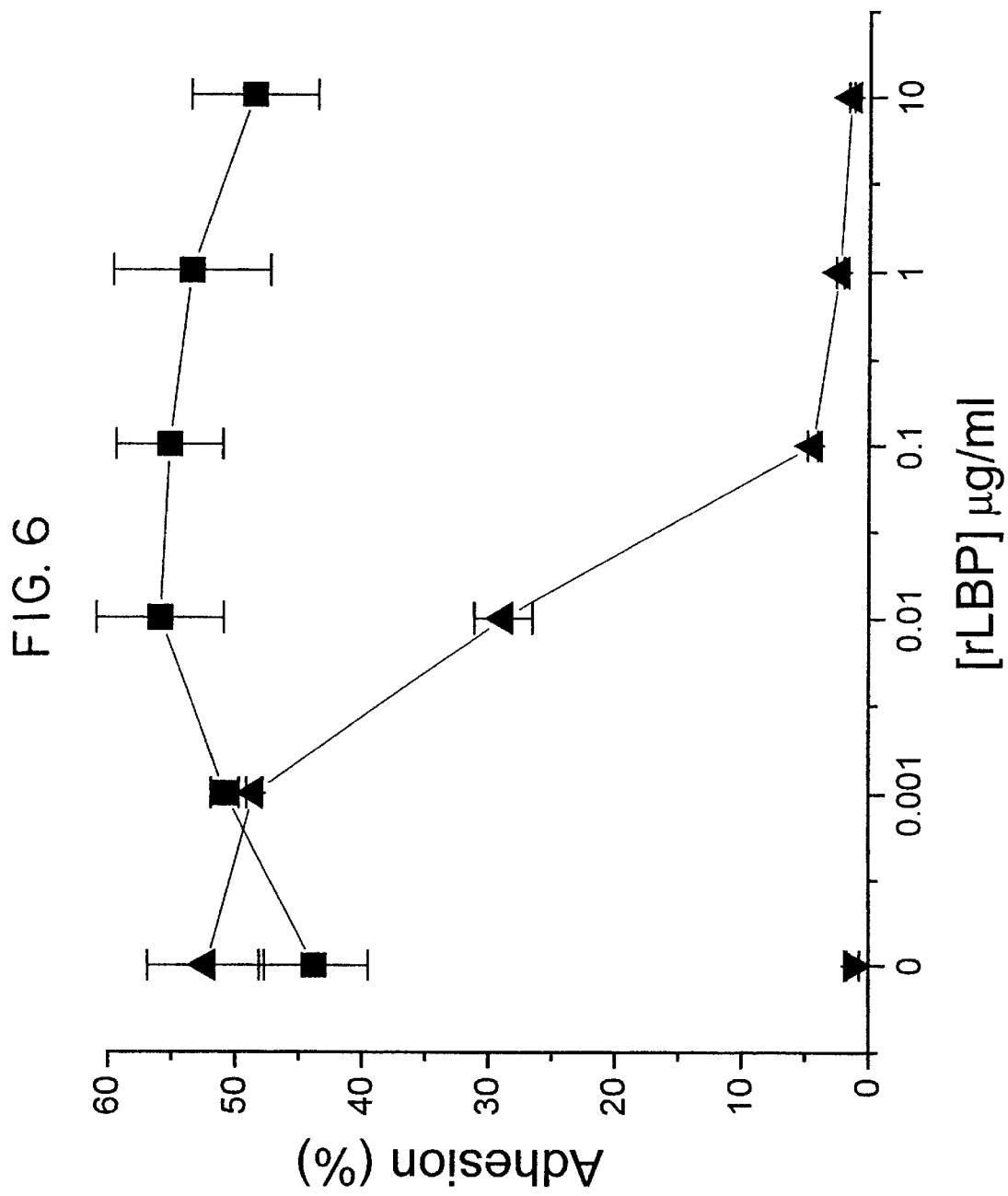
FIG. 6. Neutralization of LPS by R-HDL depends on the concentration of rLBP. Increasing concentrations of rLBP were incubated with K12 LPS (10 ng/ml) for 2 hours at 37° C. with apoA-I (■), or R-HDL (▲), both at a concentration of 100 μg/ml apoA-I. The biologically active LPS remaining was assessed by raising the rLBP concentration by 1 mg/ml in all tubes, adding PMN and measuring adhesion to fibrinogen. No stimulation of adhesion was seen with LPS alone (▼). Each point represents the mean of three wells +/− s.d. of a representative experiment repeated three times.

Substoichiometric amounts of rLBP were sufficient to enable neutralization of LPS by R-HDL. Half-maximal neutralization of 10 ng/ml of LPS by R-HDL was seen with 0.01 µg/ml of rLBP (FIG. 6). Under these conditions, each molecule of LBP (Mr 60,000) (Shumann et al., 1990, Science 249:1429) neutralized at least 7 molecules of LPS (Mr 4,000) (Kitchens et al., 1992, J. Exp. Med. 176:485) in the presence of R-HDL. This result further confirms that LBP enables neutralization of LPS by R-HDL and suggests that LBP functions catalytically in this role. In contrast to R-HDL, apoA-I alone did not neutralize LPS, and addition of even high concentrations of LBP did not enable neutralization. This result shows that neither LBP nor apoA-I has any LPS neutralizing activity and suggests an obligate role for lipids in LPS neutralization by R-HDL.

Figure 7:
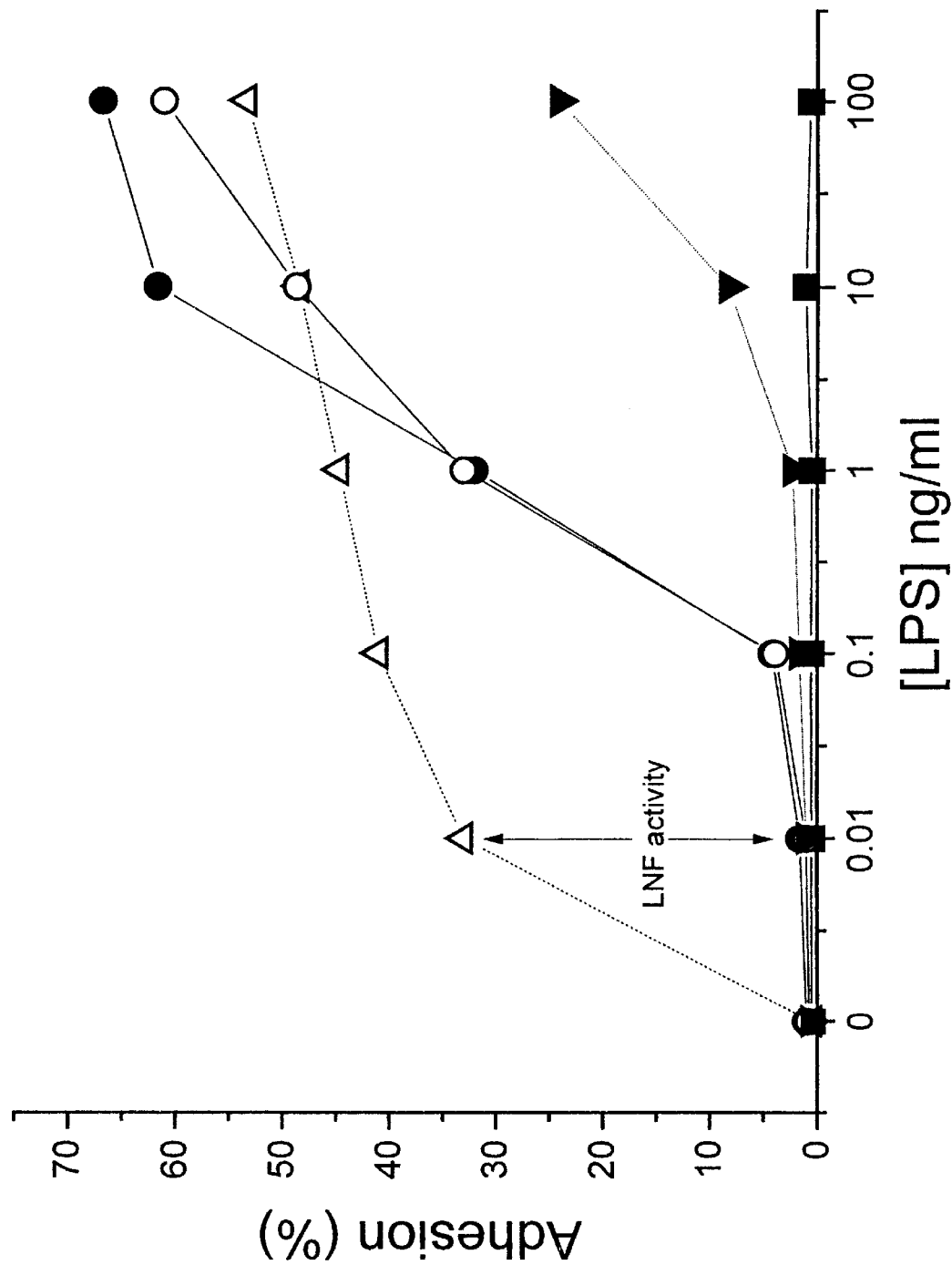
FIG. 7. Lp(A-I) particles exhibit LNF activity. Increasing concentrations of R595 LPS were incubated for 2 hours at 37° C. with buffer (AHPBS) alone (■, △), 10% NHP (●), 10% apoA-I depleted plasma (○), or 10% purified Lp(A-I) particles (▼) (dilutions normalized to the starting volume of NHP). At the end of this incubation, buffer (■) or rLBP (△, ●, ○, ▼) was added to 0.5 μg/ml, PMN were added and adhesion to fibrinogen coated surfaces was evaluated. LPS alone caused no stimulation of PMN (■). LNF activity is represented here by the difference between LBP-stimulated adhesion (△) and the loss of that stimulatory capacity (arrow). Each point represents the mean of 3 wells of an experiment selected from a set of three.

ApoA-I containing lipoprotein (Lp(A-I)) particles represent only part of the LNF activity in plasma. To assess the contribution of apoA-I containing lipoprotein (Lp(A-I)) particles to LNF activity in plasma, affinity immunosorption (SAIS) was used to remove Lp(A-I) particles from whole plasma and to recover purified Lp(A-I) particles. Chromatography on anti-apoA-I removed greater than 95% of the apoA-I from plasma, but removed only small amounts of the LNF activity (FIG. 7). The amount of LNF activity removed varied from preparation to preparation, but removal of apoA-I from NHP never resulted in more than a 66% reduction in the amount of LPS neutralized. This observation suggests that Lp(A-I) particles are not the only lipoprotein particles involved in neutralization of LPS. This finding is consistent with studies demonstrating a role for VLDL in the neutralization of LPS (Harris et al., 1990, J. Clin. Invest. 86:696).

The purified Lp(A-I) particles were also tested for LNF activity. Lp(A-I) particles demonstrated very strong LNF activity, almost completely neutralizing 10 ng/ml of R595 LPS (FIG. 7). No LNF activity was eluted from the control pre-immune column (data not shown). The efficient neutralization of LPS by Lp(A-I) particles demonstrates that like R-HDL, native HDL particles are also able to neutralize LPS. However, the neutralization of LPS by purified Lp(A-I) particles showed no dependence on exogenously added LBP. This finding suggested that native Lp(A-I) particles possess a lipid transfer protein with the same function as LBP; possibly the lipid transferase LBP itself was present in these particles.

LBP/Septin activity copurifies with Lp(A-I) particles. Lp(A-I) particles were assayed for LBP/Septin by measuring their ability to enable responses of PMN to LPS after a 10 minute incubation. Strong LBP/Septin activity was observed in Lp(A-I) particles as shown by the large increase in PMN adhesion over LPS alone (FIG. 8A). In contrast, plasma depleted of apoA-I showed a marked reduction in LBP/Septin activity such that approximately one thousand times more LPS was required to observe the level of adhesion seen in the presence of Lp(A-I). The copurification of LBP/Septin activity with Lp(A-I) was confirmed by measuring the ability of fractions to enable binding of ELPS to macrophages (FIG. 8B). NHP demonstrated strong LBP/Septin activity in this assay, enabling avid binding of ELPS to macrophages. In contrast, plasma depleted of Lp(A-I) by passage over the anti-apoA-I column was devoid of this activity, promoting no binding of ELPS. Greater than 62% of the LBP/Septin activity observed in this assay, was recovered in the eluate from the anti-apoA-I column (purified Lp(A-I) particles). A non-specific loss of activity from NHP of approximately 35% was seen after passage over a pre-immune IgG column, but no activity was recovered in the eluate from this column, confirming that LBP/Septin activity specifically copurifies with Lp(A-I) particles. These results indicate that Lp(A-I) particles bear not only LNF activity but also bear LBP/Septin activity, and that nearly all the LBP/Septin activity in plasma resides on Lp(A-I) particles.

Figure 9:
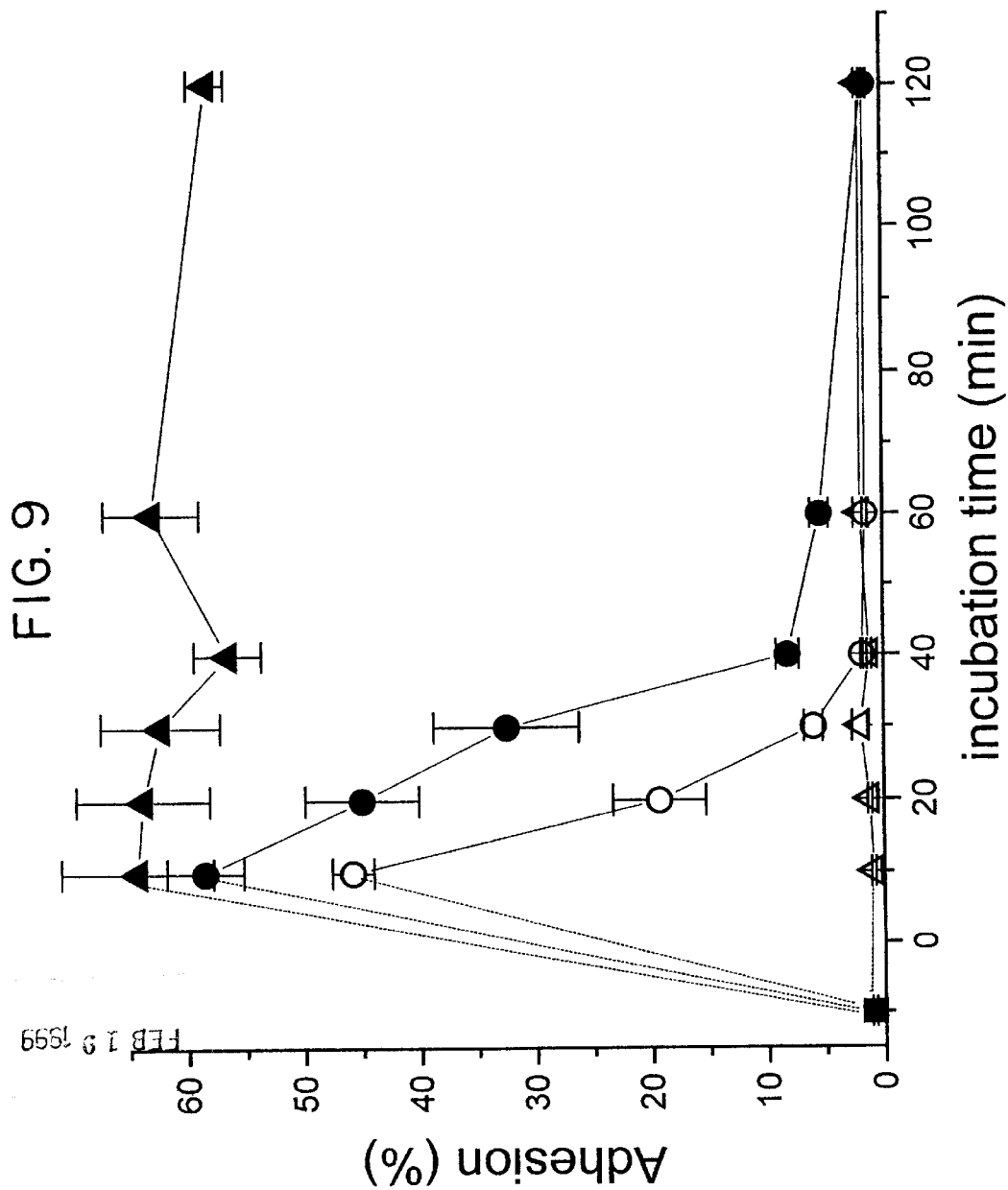
FIG. 9. Lp(A-I) particles contain both LBP/Septin and LNF activities. R595 LPS (10 ng/ml) was incubated for the stated times at 37° C. in the presence of 10% eluate from a pre-immune IgG column (△, ▲) or 10% purified Lp(A-I) particles (○, ●). At the end of this incubation, buffer (APBS) (△, ▲) or rLBP (0.5 μg/ml) (▲, ●) was added, and the mixture was incubated an additional 10 minutes, PMN were then added and binding of PMN to fibrinogen coated wells was measured. LPS alone (■) did not stimulate cells. Each point represents the mean of 3 wells +/− s.d. of a representative experiment repeated three times.

The association of both LNF and LBP/Septin activity with apoA-I containing particles was confirmed by following the kinetics of PMN stimulation by LPS and purified Lp(A-I) particles. LPS was incubated for various times with either purified Lp(A-I) particles or with the eluate from a control, pre-immune column (FIG. 9). The capacity of LPS to stimulate PMN was rapidly enabled by Lp(A-I) particles, thus demonstrating LBP/Septin activity. Upon further incubation, the mixture lost the ability to stimulate PMN. This loss of activity was due to neutralization of the LPS since addition of rLBP at the end of the incubation was not able to restore activity. The eluate from the control pre-immune column showed no LBP/Septin or LNF activity, demonstrating that these activities are specifically associated with Lp(A-I) particles. These studies also show that the sequential enabling and neutralization of LPS-mediated responses observed in whole plasma (FIG. 1) may be recapitulated with purified Lp(A-I) particles.

LBP is physically associated with Lp(A-I) particles. Because the above functional data suggested that LBP may be present in the Lp(A-I) particles, LBP associated with these particles was measured by ELISA (Table 1). NHP was found to contain 2.8 $\mu$g/ml of LBP. Depletion of Lp(A-I) particles reduced LBP to undetectable levels (>99% depletion). Lp(A-I) particles eluted from the column contained 0.88 $\mu$g/ml of LBP while LBP was undetectable in the eluate from the control pre-immune column. Thus, LBP detected by ELISA is specifically retained by the anti-apoA-I column suggesting that LBP is physically associated with Lp(A-I) particles.

TABLE 1

LBP Content ($\mu$g/ml) in Immunoaffinity Column Fractions

| EXPT. # | NHP | flow through anti-apoA-I column | eluate anti-apoA-I column | flow through pre-immune column | eluate pre-immune column |
|---|---|---|---|---|---|
| 1 | 3.75 | <0.025 | 1.00 | 1.50 | <0.025 |
| 2 | 1.50 | <0.025 | 1.03 | 1.13 | <0.025 |
| 3 | 3.25 | <0.025 | 0.63 | 2.50 | <0.025 |
| average | 2.80 | <0.025 | 0.88 | 1.71 | <0.025 |

NHP from 3 separate individuals was subjected to immunoaffinity adsorption on a column coupled with goat anti-human apoA-I IgG or goat pre-immune IgG. Fractions were equalized to the starting volume of plasma, and the concentration of LBP levels was determined by ELISA as described in Materials and Methods. Values given are the LBP concentration in $\mu$g/ml. Each value is the mean of triplicate wells. The limit of detection of the ELISA is 0.025 $\mu$g/ml LBP.

Figure 10A:
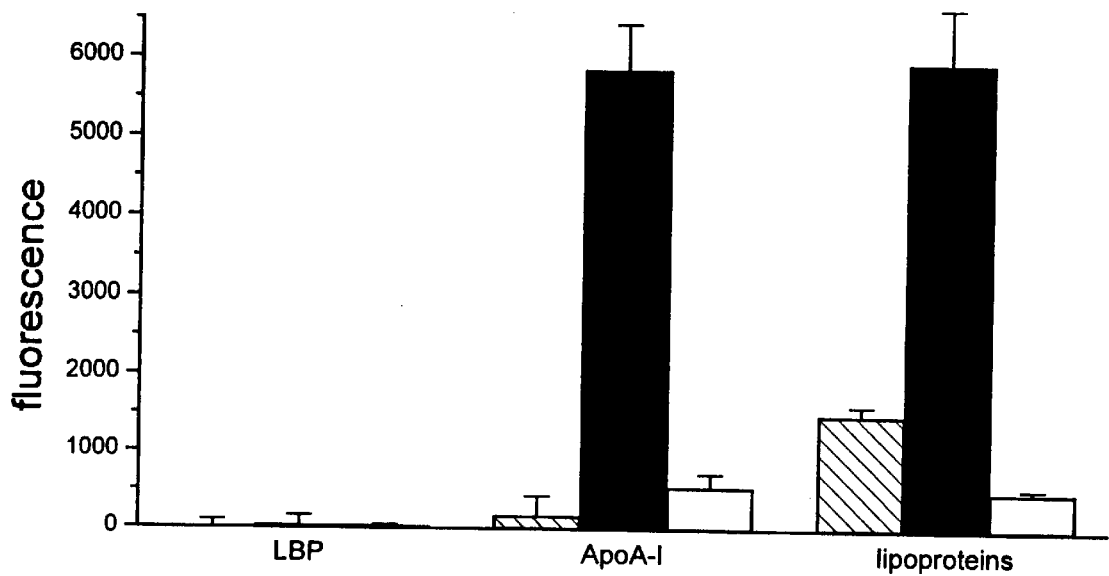
FIG. 10. Anti-LBP captures apoA-I. Terasaki plates were coated with mAbs against LBP (hatched bars), apoA-I (solid bars) or CD14 (open bars) followed by addition of rLBP (0.1 μg/ml), apoA-I (0.1 μg/ml) or partially purified lipoproteins (5 μg/ml) for 30 minutes. Captured apoA-I was detected with rabbit anti-apoA-I (panel A) and captured LBP was detected with rabbit anti-rLBP (panel B). Background signal (no LBP or lipoprotein added) was determined for each combination of immobilized antibody and secondary antibody and was subtracted from the data shown. Each bar represents the mean +/− s.d. of a representative experiment repeated 3 times.
Figure 10B:
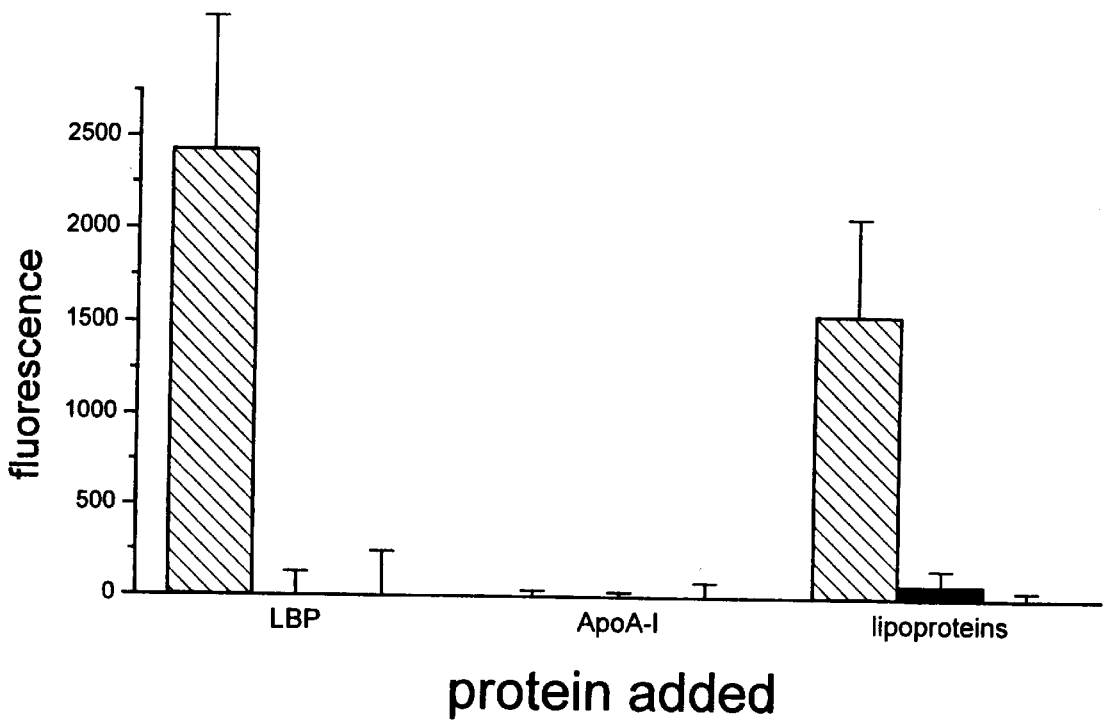

The reciprocal experiment (capture of apoA-I with anti-LBP) was performed using a modified ELISA (FIG. 10). Solutions of lipoprotein particles were incubated in plates coated with anti-IBP mAb 17G4. This step results in capture of both LBP and any associated apolipoproteins. ApoA-I associated with the captured LBP was then detected using polyclonal anti-apoA-I. Since NHP contains a high concentration of apoA-I (≠1 mg/ml), nonspecific binding of this protein from plasma precluded detection of a signal above background. To avoid this complication, the analysis was performed using partially purified lipoprotein particles isolated by chromatography on a column of HiPak™ Aldehyde. This procedure results in quantitative recovery of LBP/septin activity from plasma, but a 100-fold reduction in protein concentration. Anti-LBP mAb 17G4 captured not only LBP but also apoA-I from this solution (FIG. 10A). This observation confirms physical association of LBP with apoA-I containing lipoproteins. Under identical conditions, surface-bound monoclonal anti-apoA-I captured a small amount of LBP (FIG. 10B). This may be due to the fact that the immobilized anti-apoA-I mAb is saturated and capture of the apoA-I is thus incomplete. Experiments with lower concentrations of partially purified lipoproteins showed capture of up to 79% of the LBP with anti-apoA-I (data not shown).

Parallel studies confirmed the efficacy and specificity of the antibodies used above. Surface-bound anti-LBP mAb 17G4 captured purified rLBP as detected with a rabbit anti-LBP antibody (FIG. 10). No rLBP was captured if the 17G4 was replaced with an irrelevant monoclonal, confirming the specificity of this mAb, and the rabbit anti-LBP did not detect apoA-I captured by another monoclonal antibody, confirming the specificity of this polyclonal antibody. In a similar fashion, surface-bound anti-apoA-I captured purified apoA-I as detected with the goat anti-apoA-I second antibody. No apoA-I was captured if the monoclonal antiapoA-I was replaced with an irrelevant monoclonal. Importantly, the polyclonal anti-apoA-I did not detect LBP captured by 17G4 indicating that it does not recognize LBP (FIG. 10A). Since this polyclonal anti-apoA-I antibody was used in the affinity isolation of Lp(A-I) particles described above, the coisolation of LBP with apoA-I observed above is unlikely to be an artifact caused by crossreactivity of the goat anti-apoA-I with LBP.

Discussion

Having developed an assay for the biologic activity of LPS that requires only a 10 min exposure of LPS-containing samples to cells, the kinetics of LPS neutralization in NHP were studied. This assay contrasts with other assays used in the study of in vitro neutralization of LPS (e.g., production of cytokines by monocytes), which require at least 4 hours incubation of cells with samples and are therefore blind to the rapid changes in the availability of LPS described here. Using this assay, it was found that plasma first enabled LPS to stimulate cells, with activity reaching a peak within 10 minutes. Subsequently, the ability of LPS to stimulate cells slowly decreased over the next 2 hours. This decline was not due to a loss of LBP/Septin activity in the plasma but to sequestration of the LPS in a form which was no longer available for LBP-mediated transfer to cell-surface CD14. Thus, plasma contains factors which sequentially enable then neutralize the biological effects of LPS.

Despite the well-documented ability of HDL to bind and neutralize LPS in plasma (Skarnes et al., supra; Ulevitch et al., supra; Munford et al., supra; Flegel et al., supra) and studies showing that intravenous R-HDL protects against death in animal models of endotoxic shock (Hubsch et al., 1993, Circ. Shock 40:14); Levine et al., 1993, Proc. Natl. Acad. Sci. USA 90:12040), the present results indicate that R-HDL particles alone, reconstituted from highly purified components (apoA-I, PC, and cholesterol), are unable to bind or neutralize purified LPS. The inability of LPS to spontaneously interact with R-HDL is consistent with the biophysical properties of LPS and phospholipids. These membrane-forming amphiphiles diffuse very slowly between bilayers, and appreciable movement of phosphoplipids is only observed in the presence of proteins such as phospholipid exchange proteins (Wirtz, 1991, Annu. Rev. Biochem. 60:73) which catalyze interbilayer movement. Addition of rLBP to R-HDL enabled rapid, potent, dose-dependent binding and neutralization of LPS by R-HDL. By analogy with other lipid exchange proteins (i.e., lipid transfer proteins), it appears that LBP enables neutralization of LPS by facilitating its diffusion from LPS vesicles or micelles into HDL.

rLBP enabled effective neutralization of LPS at doses substoichiometric to the dose of LPS neutralized. Each molecule of LBP caused neutralization of at least 7 molecules of LPS under the conditions shown in FIG. 6. This result implies that LBP acts catalytically to transfer LPS to R-HDL. Thus, LBP appears to catalytically transfer LPS to at least two destinations, CD14 as has been recently described (Hailman et al., supra) and now HDL.

The results disclosed herein indicate that LBP circulates in plasma in association with apoA-I. Over 99% of LBP detected by ELISA and virtually all of the LBP/Septin activity was removed from plasma by passage over an anti-apoA-I column, and both LBP/Septin activity and LBP protein was recovered in the eluate from the anti-apoA-I column. Reciprocal studies showed that an immobilized monoclonal antibody against LBP captured not only LBP but also apoA-I (FIG. 10). LBP thus joins a group of over 17 apolipoproteins that associate with apoA-I-containing lipoproteins (Marcel et al., 1990, J. Clin. Invest. 85:10; Jordan-Starck et al., 1992, Curr. Op. Lipidology 3:75; Novotny et al., 1989, J. Biol. Chem. 264(31):18832; Stafforini et al., 1987, J. Biol. Chem. 262(9):4215; Cheung et al., 1986, J. Lipid Res. 27(11):1135; Kunitake et al., 1992; Proc. Natl. Acad. Sci. USA 89:6993). Because of the relative abundance of LBP ($\neq$5 mg/ml) (Calvano et al., 1994, Arch. Surg. 129:220) and apoA-I ($\neq$1 mg/ml) in plasma, it is likely that fewer than one in 100 HDL particles bear an LBP. ApoA-I-containing lipoproteins are tremendously heterogeneous in composition, thus these studies do not identify other constituents in Lp(A-I) particles associated with LBP.

These studies show further that neutralization of LPS requires both lipoprotein and an enzyme to catalyze movement of LPS into the lipoprotein. ApoA-I-containing lipoproteins bear both of these components and consequently are strong neutralizers of LPS (FIG. 7). Removal of apoA-I from plasma, however, caused only partial loss of LPS neutralizing activity (FIG. 7). Since apoA-I-depleted plasma contains abundant lipoproteins (LDL, VLDL), only a transfer enzyme is needed for neutralization to be observed. FIG. 6 shows that as little as 0.01 mg/ml of LBP can catalyze significant neutralization of LPS in the presence of excess lipoprotein. It is possible, therefore, that the small amount of LBP remaining in the apoA-I-depleted plasma is sufficient to enable neutralization of LPS. It is also possible that an additional lipid transfer or exchange activity exists in plasma.

The finding that lipoproteins in plasma carry all the necessary cofactors for neutralization of LPS differs from previous work. Studies with ultracentrifugally isolated lipoproteins demonstrated that neutralization of LPS required factors found in the non-lipoprotein fraction (Ulevitch et al., supra; Munford et al., supra).

This difference probably results from the methods used to prepare lipoproteins. The selected affinity immunosorption (SAIS) procedure used here is a far gentler procedure than ultracentrifugation and is known to preserve the association of proteins with HDL. For example, the association of transferrin (Kunitake et al., supra) with HDL is disturbed by ultracentrifugal isolation but preserved by SAIS. Therefore, it appears that lipoproteins isolated by SAIS do not require exogenous cofactors such as LBP to neutralize LPS because LBP remains bound to Lp(A-I) particles.

LBP shows strong sequence homology with cholesterol ester transfer protein (CETP) (Shumann et al., supra) and phospholipid transfer protein (PLTP) (Day et al., 1994, J. Biol. Chem. 269:9388) (23% and 24% identity respectively). CETP is associated with HDL and transfers cholesterol esters and triglycerides between lipoproteins (Hesler et al., 1988, J. Biol. Chem. 263:5020). PLTP is also associated with HDL and transfers phospholipids into HDL (Tollefson et al., 1988, J. Lipid Res. 29:1593). LBP thus appears to be part of an emerging family of proteins characterized by sequence homology, association with HDL, and the capacity to transfer lipid species between lipoproteins. An additional homologous protein, bactericidal permeability increasing factor (BPI) (Shumann et al., supra), resides not on lipoproteins but on the membranes of the primary granules of PMN (Weersink et al., 1993, J. Immunol. 150(1):253). Lipid transfer activity has not yet been demonstrated for BPI.

A dominant role for LBP in the neutralization of LPS might be inferred from the observation that LBP is an acute phase reactant, rising from <5 μg/ml to >60 μg/ml after challenge (Calvano et al., supra) and plasma from patients in the acute phase exhibits a reduced ability to enable cytokine production by monocytes in response to LPS (Tollefson et al., supra).

ApoA-I-containing lipoproteins have all the necessary components for both enabling and neutralizing the bioactivity of LPS. In fact, these purified particles recapitulated the sequential enabling and neutralizing of LPS-mediated responses (FIG. 9) observed with whole plasma (FIG. 1). Thus, HDL sits at a crossroads in LPS trafficking. Transfer of LPS to CD14 results in a biologically active complex, while retention by lipoproteins neutralizes LPS. Accordingly, administration of LBP and other functionally similar lipid exchange/transfer proteins in association with lipoproteins, particularly HDLs, is expected to significantly benefit individuals suffering from endotoxemia and sepsis.

EXAMPLE 2

LBP Catalyzes Transfer of LPS From sCD14 To R-HDL

Figure 11:
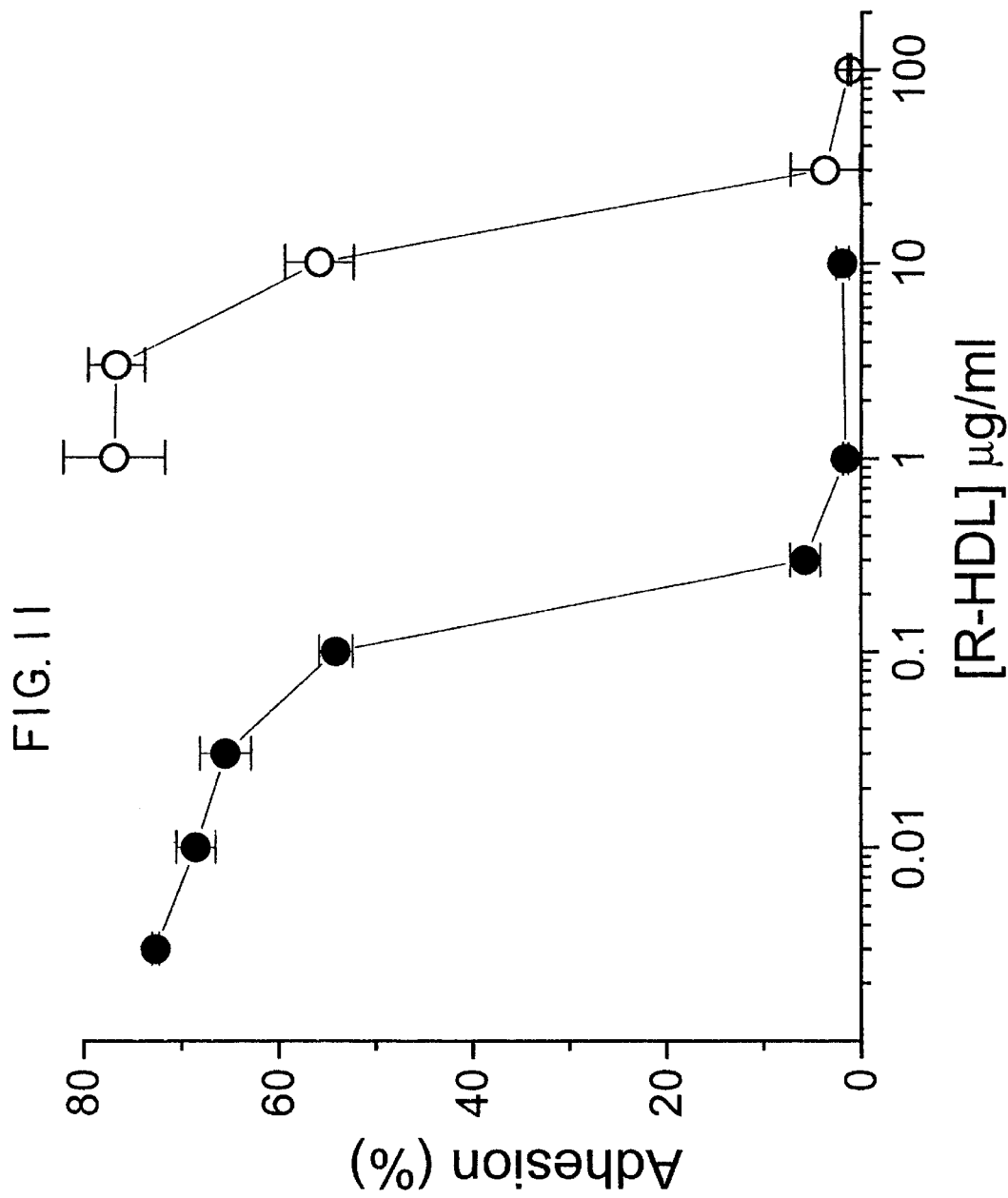
FIG. 11. LBP enables R-HDL to neutralize sCD14-LPS complexes. sCD14-LPS complexes were formed by incubating 500 μg/ml rsCD14 with 10 μg/ml LPS (rough LPS from *S. minnesota* R60) for 5 hours at 37° C. CD14-LPS complexes diluted 1000-fold (500 ng/ml sCD14 and 10 ng/ml LPS) were preincubated with the indicated concentrations of R-HDL (○) or with R-HDL and rLBP (1 μg/ml) (●) for 1 hour at 37° C. Their ability to induce adhesion of PMN to fibrinogen-coated surfaces was then assayed (Hailman et al., 1994, J. Exp. Med. 179:269).

Previous work showed that LBP catalyzes transfer of LPS from micelles to CD14 (Scheme 1, reaction 1) and transfer of LPS from micelles to HDL (reaction 2, Example 1, supra). This Example tests whether LBP also catalyzes movement of LPS from CD14 to HDL (reaction 3). Complexes of LPS with sCD14 were produced by incubating LPS with a stoichiometric excess of sCD14 for 5 hours at 37° C. Nearly all LPS is bound to sCD14 under these conditions, and the resulting complexes strongly stimulated integrin-mediated adhesion of PMN (FIG. 11). Incubation of LPS-sCD14 complexes for 5 hours with very high concentrations of R-HDL decreased their ability to stimulate PMN, suggesting that LPS partitions slowly from sCD14 to R-HDL. However, addition of LBP enabled 100-fold lower amounts of R-HDL to completely neutralize the LPS-CD14 complexes in this time (FIG. 11). This observation suggests that LBP can catalyze the movement of LPS from sCD14 to R-HDL. Thus, LBP catalyzes the three separate reactions shown in Scheme 1.

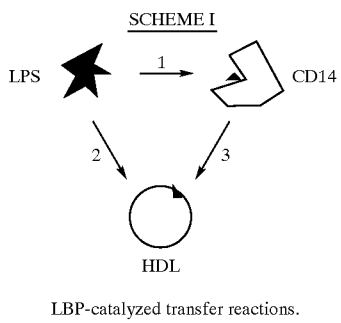

SCHEME I

LBP-catalyzed transfer reactions.

EXAMPLE 3 sCD14 Accelerates Neutralization of LPS by LBP and R-HDL

Figure 12:
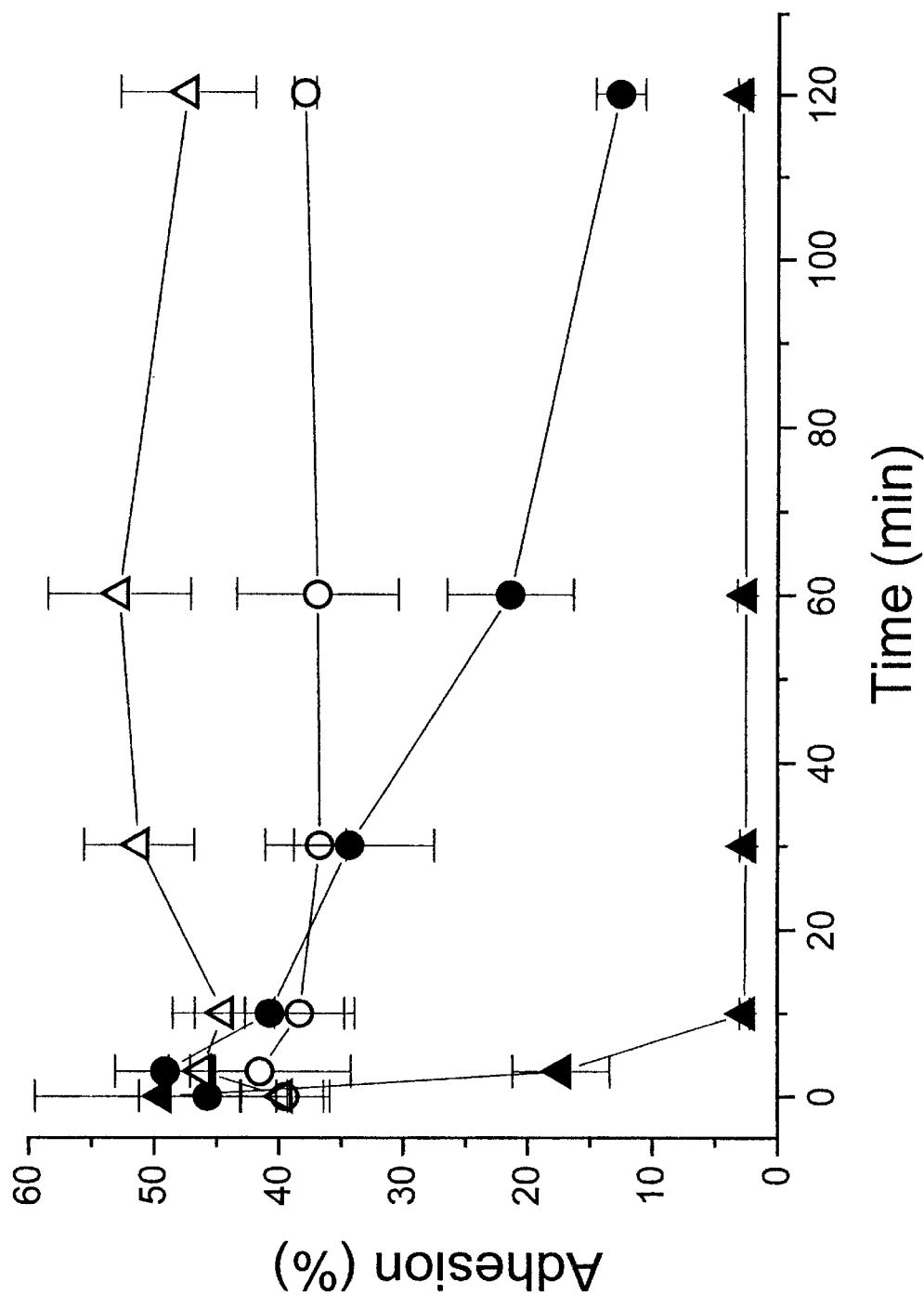
FIG. 12. sCD14 accelerates the neutralization of LPS by R-HDL and LBP. LPS (*E. coli* K12, 1 ng/ml) and LBP (0.5 μg/ml) were diluted in APBS (PSB containing CA++, MG++ and 1% HSA) and incubated for the stated interval at 37° C. with (●, ▲) or without (○, △) R-HDL (100 μg/ml apo A-I), with (△, ▲) or without (○, ●) rsCD14 (0.5 μg/ml). Biologically active LPS remaining after the 2-hour incubation was detected by adding PMN and evaluating the binding of cells to fibrinogen-coated surfaces as described (Hailman et al., supra). Each point represents the mean of 3 wells +/− s.d.

LP catalyzes a time dependent neutralization of LPS by R-HDL (Scheme 1, reaction 1, and FIG. 12), a result that appears to be due to binding of LPS to R-HDL. Addition of 0.5 μg/ml sCD14 caused a marked acceleration of this process (filled triangles, FIG. 12). Thus, LBP may transfer LPS first to CD14 and then to R-HDL at a rate faster than for the direct transfer of LPS from LPS micelles to R-HDL, i.e., reactions 1 and 3 of Scheme I proceed faster than reaction 2. This finding suggests that LBP is unlikely to shuttle LPS as a soluble LPS-LBP complex in all three reactions: CD14 could not raise the concentration of soluble LPS-LBP complexes if it receives LPS from soluble LPS-LBP complexes. Soluble CD14 is found at high levels in normal serum, and these levels increase with infection. Thus, exogenous CD14 need not be added to most individuals.

EXAMPLE 4

Figure 13:
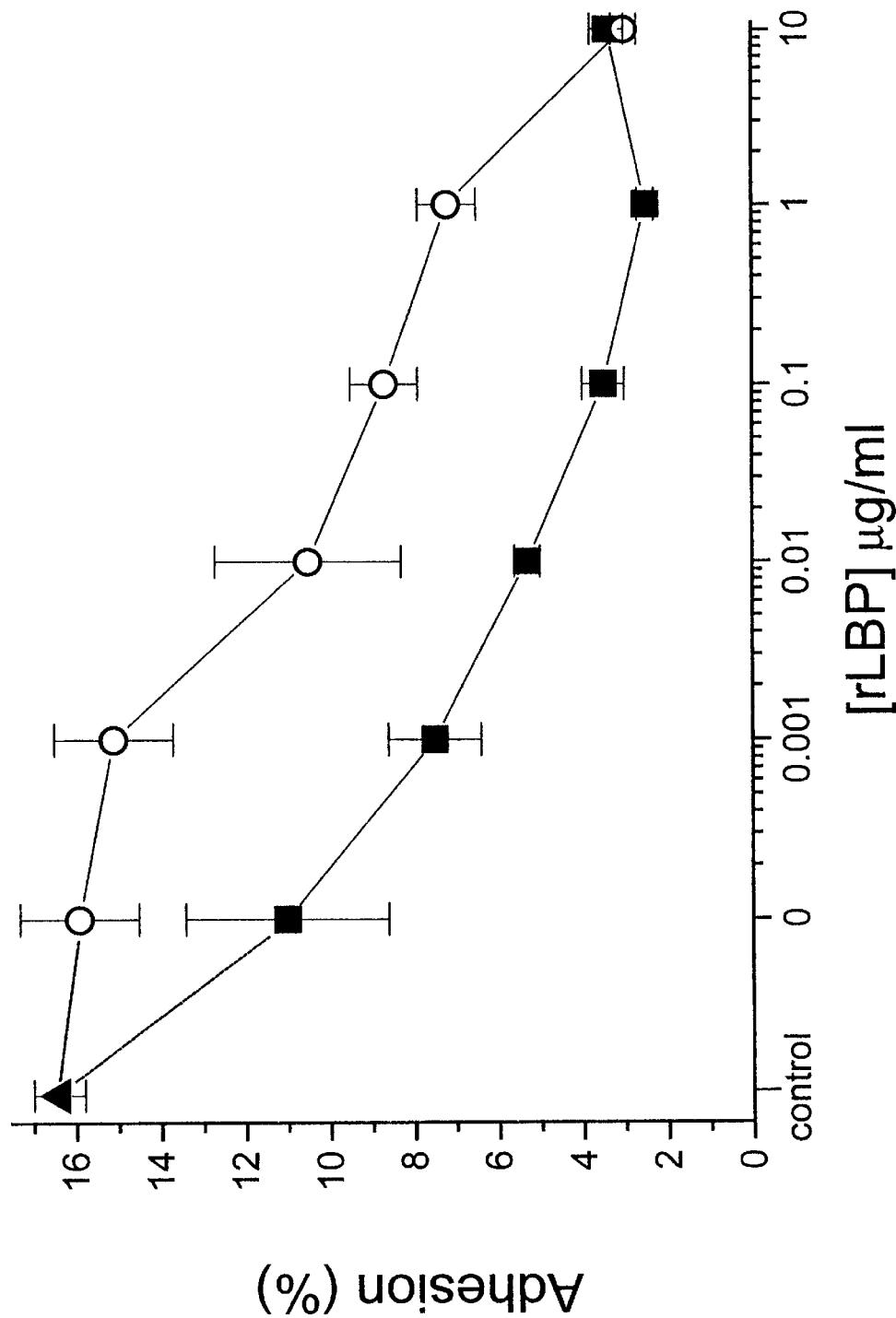
FIG. 13. Phosphatidylcholine/cholesterol vesicles neutralize LPS in a LBP-dependent fashion. LPS (*E. coli* K12, 1 ng/ml) was incubated with increasing doses of rLBP for 2 hours at 37° C. in the presence of R-HDL (■) (100 μg/ml apoA-I), or phosphatidylcholine (PC)/cholesterol vesicles (○) (concentration of lipid equivalent to that present in R-HDL), prepared as described for R-HDL with the omissions of apoA-I. To assess the amount of biologically active LPS remaining after the 2-hour incubation, the LBP concentration was raised to 1 μg/ml in each tube, PMN were added, and binding of the cells to fibrinogen-coated surfaces evaluated as described (Hailman et al., supra). LPS incubated with rLBP (10 μg/ml) in the absence of R-HDL or liposomes for 2 hours (▪), demonstrated strong cell stimulation. Points are the mean of 3 wells +/- s.d.

Phospholipid, not Apolipoprotein, is Required for LBP-Dependent Binding and Neutralization of LPS The results in Example 1 showed that mixtures of LBP and R-HDL neutralized LPS, but that purified Apo A-I and LBP failed to neutralize. To determine if phospholipid alone could neutralize LPS, mixtures of phosphatidyl choline (PC) and cholesterol were suspended as liposomes rather than incorporated into R-HDL (FIG. 13). Addition of these liposomes caused complete neutralization of LPS in an LBP-dependent fashion. PC-cholesterol liposomes were less efficient at neutralizing LPS than a comparable amount of phospholipid in R-HDL (FIG. 13). This may result from the fact that much of the PC in liposomes is not available for neutralizing LPS: it may be present on the inner leaflet of a liposome or in inner membranes of a multilamellar liposome. In contrast, all PC in an HDL particle is exposed to the medium.

Figure 14:
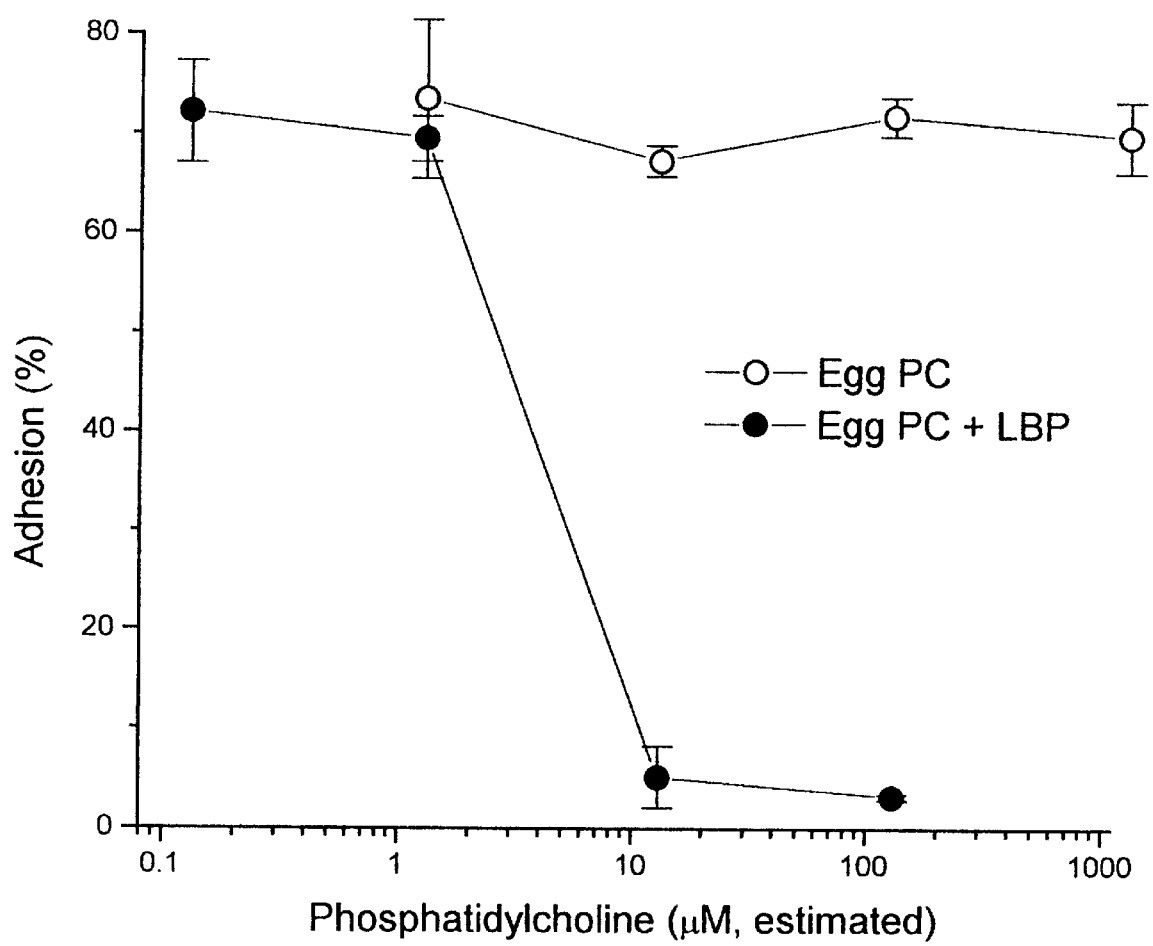
FIG. 14. LBP mediates neutralization of sCD14-LPS complexes by PC liposomes. sCD14-LPS complexes prepared as in FIG. 11 were diluted 1:1000 and preincubated with the indicated concentrations of egg PC liposomes in the presence or absence of rLBP (1 μg/ml), for 2 hours at 37° C. The samples were then added to PMN and adhesion to fibrinogen-coated surfaces was assayed (Hailman et al., supra). The concentrations of components during the preincubation step were 25% higher than indicated above and in the figure.

Liposomes also caused neutralization of LPS in LPS-sCD14 complexes, again in an LBP-dependent fashion (FIG. 14). These results suggest that LBP may transfer LPS from micelles or from sCD14 to liposomes. This hypothesis was confirmed as follows. Native PAGE of $^3$H-LPS-sCD14 complexes showed nearly all radioactivity associated with sCD14 (FIG. 15a, lane 1). Addition of unlabeled PC liposomes caused little loss of $^3$H-LPS from CD14 in a 10 hour incubation (FIG. 5a, lane 6). However, addition of LBP enabled nearly complete transfer of $^3$H-LPS from sCD14 to liposomes in one hour (FIG. 15b, lane 13). This observation confirms that LBP may catalyze movement of LPS from CD14 to liposomes.

FIG. 15 also shows that LBP catalyzes the equilibration of LPS bound to CD14 with unlabeled LPS micelles (FIG. 15B, lanes 11 and 12). Thus, the binding of LPS to CD14 is readily reversible. Note that free LPS migrates well into the acrylamide gel to a position shared by proteins of ≠400 KDa. Thus, the LPS exists in relatively small aggregates or micelles, not as vesicles. In contrast, PC liposomes do not enter the gel (not shown), and the movement of $^3$H-LPS into these liposomes is therefore accompanied by loss of radioactivity from the gel (FIG. 15B, lanes 13 and 14).

Phospholipids other than PC also neutralize LPS-CD14 complexes. For example, LBP readily transfers $^3$H-LPS from LPS-CD14 complexes to PI liposomes. Moreover, neutralization of LPS-CD14 complexes requires nearly 100-fold less PI than PC (data not shown), suggesting that PI is a good substrate for LBP.

EXAMPLE 5 sCD14 Binds Phospholipids

CD14 may bind not only LPS, but also other phospholipids. sCD14 was incubated for 2 hours with $^3$H-PI, then applied to a native gel (FIG. 16). Most PI failed to enter the gel, reflecting the large size of PI liposomes. However, some $^3$H-PI ran into the gel, suggesting the presence of PI micelles (FIG. 16, lane 5). Addition of an equimolar amount of sCD14 caused most of the PI to run coincident with the sCD14 (lane 3). Raising the amount of PI increased the amount of radiolabel associated with sCD14 (lane 4), suggesting that association of PI has a stoichiometry grater than one. Two additional observations confirm that PI, and other phospholipids, bind CD14. First, binding of $^3$H-LPS to sCD14 was measured in the presence of increasing doses of liposomes. PI, PC, phosphatidyl serine (PS) and unlabeled LPS each blocked binding of $^3$H-LPS to sCD14 (not shown), suggesting that lipids may compete with LPS for binding to CD14. Specificity for the inhibition is suggested by the finding that sphingomyelin (SM) failed to displace LPS from CD14. Second, it was previously shown that binding of LPS to sCD14 causes a distinct shift in the electrophoretic mobility of the receptor (FIG. 16). Addition of liposomes prevented LPS from causing this shift in mobility, again suggesting that they may compete with LPS for binding CD14. Importantly, phospholipids caused slight but reproducible shifts in the electrophoretic mobility of sCD14 that varied with the type of phospholipid (not shown). These data indicate that sCD14 binds not only LPS but also other phospholipids, and the binding is stable in native PAGE.

Transfer of $^3$H-PI into CD14 has been observed after short incubation times (30 minutes), and it was found that LBP caused a dramatic acceleration of PI binding (not shown). This result further confirms the binding of PI to sCD14.

While PI and other phospholipids bind sCD14, the resulting complexes do not appear to stimulate cells. No alterations in the adhesivity of PMN exposed to sCD14 and any of a wide variety of phospholipids has been observed (not shown). This finding indicates that the ability of a phospholipid to compete with LPS for binding to CD14 can be assayed by measuring its ability to block stimulation of PMN by LPS-CD14 complexes.

EXAMPLE 6

Neutralization of LPS by Phospholipids Depends on Acyl Chain Composition

Liposomes were made using PC with defined acyl chain composition, and LBP-catalyzed neutralization of LPS/sCD14 complexes was measured (FIG. 17). PC with saturated C16, C18 or C20 chains had little neutralizing activity, but a decrease in chain length to C14, C10, C8, or introduction of an unsaturation in PC with longer chain lengths, resulted in far better neutralizing activity. Control experiments showed that none of these phospholipids had toxic effects and none decreased adhesion of PMN stimulated by TNF. These results suggest that the phospholipid composition of HDL may have an important impact on its ability to neutralize LPS. These results also indicate that homogeneous phospholipid particles containing phospholipids that are good substrates for the exchange reaction can be much more effective at neutralizing LPS than naturally occurring lipoprotein particles. Accordingly, such homogenous particles have significant therapeutic potential.

EXAMPLE 7

Acute Phase Plasma Exhibits Enhanced Neutralization of LPS

The acute phase response is accompanied by changes in both LBP concentration and HDL makeup. To determine the effects of these changes, neutralization of LPS was measured using either pooled plasma from healthy donors or the plasma of a patient in gram negative septic shock. Neutralization was faster and more complete with the septic shock plasma (FIG. 18). A similar though less dramatic enhancement of neutralization was observed in comparisons of plasma drawn from volunteers before or after a 6-hour injection with LPS. These data suggest that an increase in LPS-neutralizing ability represents a response to infection that counteracts the stimulatory effects of LPS.

The mechanism underlying enhanced neutralization is believed to involve transfer of LPS into lipoprotein particles. Thus, measurement of neutralization potential of plasma from a subject can indirectly indicate the level of LPS exchange protein activity. Furthermore, this measurement can provide an indication of the presence or stage of endotoxemia, sepsis, or septic shock in a subject.

EXAMPLE 8

Neutralization of LPS by Different Lipids

The ability of various lipids, which differ in chain length and head group composition, to facilitate LBP-mediated neutralization of LPS was assayed (FIG. 19). The results indicate that while egg phosphatidyl choline (PC), C6 PC (PC having 6 carbon atoms in the acyl chain), C14 PC, and C16 PC are less effective for neutralizing LPS, C10 PC, phosphatidyl inositol (PI), C8 ceramide and cardiolysin are more effective for this purpose.

EXAMPLE 9

Phospholipid Transfer Protein Mediates Transfer of LPS to Reconstituted High-Density Lipoprotein Particles PLTP is a plasma protein known to transfer phospholipid between lipoprotein particles. The present Example relates to the observation that PLTP also transfers LPS to HDL particles.

PLTP was expressed in CHO cells following transient transfection, and serum-free culture supernatant was collected (Day et al., 1994, J. Biol. Chem. 269:9388). Culture supernatants from mock-transfected cells served as controls. FIG. 20 shows that addition of PLTP strongly enhanced the rate of LPS neutralization by reconstituted HDL particles (R-HDL). Neutralization is greater than that observed with LBP.

Additional studies showed that neutralization of LPS is caused by PLTP-mediated transfer of LPS to the R-HDL particle. Radiolabelled LPS migrates on nondenaturing gels as a broad band while R-HDL migrates as a distinct ladder of species reflecting particles bearing 2, 3, or 4 molecules of ApoA-I. Addition of medium without PLTP does not affect the migration of radiolabelled LPS in mixtures of LPS and R-HDL (FIG. 21, compare lanes 2 and 8). However, addition of PLTP-containing medium causes the LPS to migrate precisely with the bands of R-HDL (FIG. 21, compare lanes 8 and 6). These observations indicate that PLTP transfers LPS to HDL particles.

A crucial observation is that PLTP does not transfer LPS into CD14. Addition of PLTP at a range of doses did not enable responses of CD14-bearing cells to LPS (not shown), suggesting that LPS is not moved into cell surface CD14 by PLTP. Further, sCD14 exhibits fast mobility on nondenaturing gels, and addition of LBP caused prompt movement of radiolabelled LPS into sCD14 (FIG. 21, lane 9), in keeping with our earlier observations. In contrast, addition of PLTP caused no movement of LPS to sCD14 above that observed in control incubations (compare FIG. 21, lanes 11 and 13). These observations indicate that unlike LBP, transfer of LPS to HDL particles by PLTP is direct, and does not employ sCD14 as an intermediate.

Since undesirable stimulation of cells by LPS (leading to septic shock) requires CD14-LPS complexes as an intermediate, the above results indicate that PLTP will not promote cellular responses to LPS, a result that has been demonstrated. Rather, by causing movement of the LPS to lipoproteins, PLTP will neutralize the LPS and lessen cellular responses to the LPS.

The observations reported in this Example confirm that sepsis may be alleviated by treatment of animals or humans with doses of PLTP that raise the serum concentration of PLTP, or with compositions of reconstituted lipoprotein particles containing PLTP, which can function as LPS sponges.

Materials and Methods

Reagents. LPS from *Salmonella minnesota* strain R60 (Ra) and $^3$H-labeled LPS ($^3$H-LPS) from *E. coli* LCD25 (K12) (Munford et al., 1992, J. Immunol. Methods 148:115) was purchased from List Biological Laboratories (Campbell, Calif.). Human serum albumin was purchased from Armour Pharmaceutical Company (Kankakee, Ill.). Recombinant human LBP and recombinant human sCD14, expressed and purified as described (Hailman et al., 1994, J. Exp. Med. 179:269–277).

Production of rPLTP. Human recombinant PLTP was prepared using standard methods. Briefly, human PLTP cDNA was cloned from a cDNA library constructed from human umbilical vein endothelial (HUVE) cells by ligation of the cDNA to mammalian expression vector pZem228cc (Day et al., 1995, J. Biol. Chem 269:9388–9391). Clones containing the complete PLTP cDNA were transfected into baby hamster kidney (BHK-570) cells using calcium phosphate mediated transfection (Waechter et al., 1982, Proc. Natl. Acad. Sci. USA 79:1106–1110). The selectable marker Neo(G418) was used to select for stable colonies by plating the initial transfection at low concentrations of cells and the use of cloning cylinders.

Purification of plasma-derived PLTP. PLTP was purified to homogeneity from human plasma using dextran sulfate/CaC12 precipitation and a combination of phenyl-Sepharose, CM-cellulose, DEAE-cellulose, heparin-Sepharose, and hydroxylapaptite chromatography as described (Tu and Nishida, 1993, J. Biol. Chem 268:23098–23105).

Preparation of anti-PLTP and control immunoglobulins. Polyclonal antibody was raised in rabbits by injecting approximately 275 mg of rPLTP with an equal volume of Freund's adjuvant. Animals were immunized once after three weeks and bled at 3–4 week intervals by heart puncture. Anti-rPLTP IgG and control IgG were prepared following the procedure of McKiney and Parkinson (1987, Immunological Meth. 96:271–78).

Preparation of reconstituted HDL particles. R-HDL was prepared by the sodium cholate dialysis method as previously described (Matz and Jonas, 1982, J. Biol. Chem 257:4535). Briefly, purified apolipoprotein A-I (apoA-I), was mixed with egg phosphatidylcholine (PC), cholesterol and cholate at a molar ratio of 80:4:1:80 (PC:cholesterol:apoA-I:cholate) and cholate was removed with extensive dialysis against PDEDTA (Dulbecco's PBS lacking $Ca^{2+}$ and $Mg^{2+}$ with 1 mM EDTA) containing 0.01% sodium azide. Final preparations were stored in PDEDTA with 0.01% azide at 4° C. All concentration values for R-HDL particles are expressed as the equivalent concentration of apoA-I in (mg/ml).

Formation of LPS-sCD14 complexes. LPS and sCD14, at concentrations 500-fold higher than those stated in each figure, were incubated together for 5–18 h at 37° C. in PBS with 0.5% HSA. These high concentrations used were designed to maximize binding of LPS to sCD14 as previously described (Hailman et al., 1994, J. Exp. Med. 179:269–277).

Stimulation of PMN by LPS. To assess the biologic activity of LPS the adhesion of human PMN to fibrinogen-coated surfaces was measured as described (Hailman et al., 1994, J. Exp. Med. 179:269–277; Wurfel et al., 1994, J. Exp. Med. 180:1025–1035). In this assay, stimulation of PMN adhesion by LPS is dependent on the presence of LBP or plasma. Adhesion of the stimulated PMN to fibrinogen is mediated by the leukocyte integrin CD11b/CD18 (CR3, Mac1) (van Kessel et al., 1994, J. Immunol. Methods 172:25–31). Briefly, mixtures containing LPS were diluted in APBS (Dulbecco's PBS with $Ca^{2+}$ and $Mg^{2+}$, 0.5% human serum albumin) to the concentrations indicated, yielding a final volume of 50 ml. Ten $\mu$L of freshly isolated PMN ($2 \times 10^7$ cells/ml in HAP (Dulbecco's PBS with 0.5 U/ml aprotinin, 0.05% human serum albumin, 3 mM D-glucose) fluorescently labelled with 5-(and 6-) carboxyfluorescein diacetate, succinimidyl ester as described (van Kessel et al., 1994, J. Immunol. Methods 172:25–31) were added and incubated for 10 minutes at 37° C. to stimulate the cells. PMN were then washed into HAP and added to a 72 well Terasaki plate pre-coated with fibrinogen. After 15 minutes at 37° C., adherence of PMN to the plate was quantitated. The fluorescence in each well was measured using a Cytofluor 2300 (Millipore Corp.) as a way of quantitating the total number of cells per well. The plate was then washed and fluorescence was measured again. Binding is expressed as the percentage of cells remaining in the well after the washing step (Adhesion (%)). Donor to donor variation in maximal responses (25–75% adhesion) prohibited averaging results of separate experiments, but the pattern of responses was highly reproducible.

Stimulation of interleukin-6 (IL-6) production in whole blood—Heparinized blood was obtained by venipuncture from healthy human volunteers. LPS was preincubated with R-HDL and other reagents (see below), then added in a volume of 1 (1 to 99 (1 blood in a microcentrifuge tube. Samples were incubated for 4h at 37° C. in a 5% $CO_2$ environment, then centrifuged for 3 min. at 1500×g. Plasma was collected and stored at −20° C. until assayed for IL-6 by ELISA.

IL-6 ELISA. IL-6 levels were measured using a modification of a commercially available human IL-6 ELISA kit (BioSource International, Camarillo, Calif.).

Anti-IL-6 monoclonal antibody was diluted to 40 $\mu$g/ml in PBS; 5 $\mu$l/well were added to Terasaki plates (Robbins Scientific, Sunnyvale, Calif.), and the plates were left at 4° C. overnight. The plate was washed by flooding with wash buffer (BioSource), blocked with gelatin (0.1% in PBS, 10 $\mu$l/well) for 1 h at room temperature, and washed again. Five $\mu$l of biotin conjugate (biotin-labeled second anti-IL-6 antibody) were added to each well, followed by 5 $\mu$l of plasma samples diluted 10× in dilution buffer (BioSource). After a 2 h incubation at 37° C., wells were washed 2× with wash buffer, and 10 $\mu$l of streptavidin-alkaline phosphatase solution (Bio-Rad, Hercules, Calif.) was added. After a 1 h incubation at room temperature, the fluorescent alkaline substrate Attophos (JBL scientific, San Luis Obispo, Calif.) was added, and fluorescence was measured using a Cytofluor 2300 fluorescence plate reader (Millipore).

Neutralization of LPS and LPS-sCD14 complexes. Neutralization of LPS was measured as the loss of its ability to stimulate adhesion of PMN to fibrinogen or to stimulate IL-6 production in whole blood. Neutralization of ability to stimulate PMN adhesion was assayed as previously described (Wurfel et al., 1994, J. Exp. Med. 180:1025–1035). Briefly, LPS, R-HDL and variable amounts of LBP were diluted in APBS to a final volume of 50 µl. After incubation for the stated time at 37° C., the amount of available LPS remaining in the tube was assessed by adding PMN resuspended in 50% human plasma, and measuring adhesion as described above.

Neutralization of ability to stimulate IL-6 production was performed in a similar manner. LPS was incubated with R-HDL and LBP or culture medium from PLTP-transfected or control cells in 10 µl APBS for increasing times at 37° C. The biologically active LPS remaining was measured by adding 1 µl of the mixture to 99 µl blood and assaying for IL-6 production as described above. The same methods were used to measure neutralization of LPS-sCD14 complexes, which were formed by preincubation of LPS with sCD14 as described above. The amount of IL-6 produced in whole blood in response to LPS-sCD14 complexes was very similar to the amount produced with the same dose of LPS without added sCD14.

Electrophoresis. $^3$H-LPS was sonicated for 1 min and incubated at 37° C. for various times with R-HDL and other proteins as indicated in the figure legends. Just before electrophoresis, ½ volume of a loading buffer containing 0.005% bromophenol blue and 20% glycerol in PBS was added to each sample. The samples were run in continuous buffer (pH 8.6), non-denaturing tris-glycine 8–16% polyacrylamide step-gradient gels (Novex, San Diego, Calif.) at 100–150 V for 2–3 h in a running buffer containing 192 mM glycine, 24 mM Tris, pH 8.3. After electrophoresis, the gels were soaked in ENHANCE (Dupont, Boston, Mass.) for 45 min., washed 3x for 15 min in ddH$_2$O, dried, and exposed to Fuji RX film for 4 d.

Results

PLTP Mediates the Transfer of $^3$H-LPS to R-HDL. Non-denaturing polyacrylamide gel electrophoresis (native PAGE) showed the association of $^3$H-LPS with soluble CD14 (sCD14) and with R-HDL particles (Hailman et al., 1994, J. Exp. Med. 179:269–277). This technique was utilized to ask whether PLTP could mediate the transfer of $^3$H-LPS to R-HDL. $^3$H-LPS was incubated with R-HDL in the presence of culture medium from cells transfected with the cDNA for human PLTP (rPLTP medium) or medium from non-transfected cells (control medium), then subjected to native PAGE. As shown previously (Wurfel et al., 1995, J. Exp. Med. 181:1743–54), $^3$H-LPS did not spontaneously associate with R-HDL under these conditions (FIG. 22, lane 1). However, when $^3$H-LPS was incubated with rPLTP medium and R-HDL before electrophoresis, the pattern of migration of $^3$H-LPS was similar to the pattern of R-HDL seen with silver staining (FIG. 22, lanes 6 and 9), indicating the association of $^3$H-LPS with R-HDL particles. Incubation of $^3$H-LPS with R-HDL, LBP and sCD14 also resulted in transfer of LPS to R-HDL, as we have shown previously (FIG. 22, lanes 8). $^3$H-LPS did not show this distinctive pattern after incubation with control medium and R-HDL or with rPLTP or control medium alone (FIG. 22, lanes 4, 5, 3 respectively). These results suggest that rPLTP can transfer $^3$H-LPS to R-HDL.

rPLTP Mediates the Neutralization of LPS by R-HDL. Many studies have shown that the incorporation of LPS into lipoproteins or phospholipid vesicles results in the neutralization of the biological potency of LPS (Dijkstra et al., 1987, J. Immunol. 138:2663–2670; Flegel et al., 1993, Infect. Immun. 61:5140). In addition, LBP can accelerate the movement of LPS into R-HDL particles, thereby facilitating the neutralization of LPS (Wurfel et al., 1994, J. Exp. Med. 180:1025–1035). The ability of rPLTP to transfer $^3$H-LPS into R-HDL particles suggests that rPLTP medium should also facilitate the neutralization of LPS by R-HDL. To demonstrate this activity, LPS was incubated with R-HDL for increasing times in the presence of rPLTP medium or control medium, then neutralization of LPS measured as the time-dependent loss of its ability to stimulate adhesive of neutrophils to fibrinogen-coated surfaces. Preincubation of LPS with R-HDL alone or with R-HDL and control medium did not cause a significant loss of stimulatory capacity for adhesive responses of neutrophils (FIG. 23). However, preincubation of LPS with RPLTP medium and R-HDL, but not with rPLTP medium alone, caused a time-dependent loss of stimulation, with almost complete loss of activity after 1 h of incubation. Thus, rPLTP is able to facilitate the transfer of LPS to R-HDL particles, resulting in the neutralization of LPS.

It was confirmed that rPLTP mediates neutralization of LPS by R-HDL by measuring cytokine production in whole blood in response to LPS. Monoctyic cells produce a variety of cytokines in response to LPS, including tumor necrosis factor, interleukin (IL)-1, IL-6, and IL-8, and these cytokines are thought to mediate many of the pathophysiological effects of LPS in vivo (Beutler et al., 1985, Science 229:869–871; Dinarello et al., 1991, J. Inf. Dis. 163:1177–1184; Fletcher et al., 1990 J. Immunol. 145:4185; Huber et al., 1991, Science 254:99).

IL-6 production in whole blood was measured, and it was determined that LPS caused a dose-dependent stimulation of IL-6 production (not shown). Preincubation of LPS with R-HDL alone or rPLTP medium alone before addition to blood resulted in very little change in IL-6 production (FIG. 24). However, preincubation of LPS with R-HDL and rPLTP medium caused a time-dependent loss in stimulation of IL-6 production (FIG. 24). Comparison of this result with the dose-response curve for IL-6 production in response to LPS (not shown) suggested that about 90% of the LPS was neutralized within 1 h under these conditions, and at least 97% of the activity was neutralized after 2 h. Incubation of LPS with control medium and R-HDL failed to cause neutralization of LPS (not shown). These results confirm that rPLTP mediates neutralization of LPS by R-HDL.

PLTP Must Interact with LPS to Mediate Neutralization of LPS by R-HDL. It was recently shown that PLTP can cause HDL conversion (Tu and Nishida, 1993, J. Biol. Chem 268:23098–23105; Jauhiainen et al., 1993, J. Biol. Chem 268:4032–4036), or the change in size distribution of HDL particles. This ability of PLTP to modify HDL particles raised the possibility that PLTP might accelerate the transfer of LPS to R-HDL by modifying the lipoprotein particles, rather than by interacting with LPS directly. To explore this possibility, rPLTP medium was preincubated with R-HDL before adding LPS, and then the rate of neutralization of LPS was examined. If PLTP acts by modifying R-HDL, then faster neutralization of LPS would be expected under these conditions compared with the previous experiment when LPS, rPLTP medium and R-HDL were added simultaneously. Preincubation of rPLTP medium with R-HDL did not result in significantly faster neutralization than when all three reagents were added simultaneously (FIG. 25). This result suggests that rPLTP mediates the neutralization of LPS by R-HDL in a way that does not result in modifying R-HDL, but rather by interacting with LPS directly and transferring it to R-HDL.

To confirm this result, a polyclonal antibody raised against PLTP (anti-PLTP IgG) was employed. This antibody blocks the transfer of phospholipids by whole plasma and by rPLTP (not shown), confirming that it recognizes PLTP and blocks its function. It was determined that anti-PLTP IgG, but not a control IgG, inhibited the neutralization of LPS by rPLTP medium and R-HDL (see below), confirming that rPLTP mediates the neutralization of LPS by R-HDL in these experiments. Anti-PLTP IgG was then used to confirm that PLTP must interact with LPS in order to mediate its neutralization. R-HDL was incubated with rPLTP medium for 1 h, then anti-PLTP IgG and LPS were added, and the subsequent neutralization of LPS was measured. If PLTP mediated neutralization of LPS by acting on R-HDL, then anti-PLTP IgG would not be expected to inhibit the neutralization of LPS by RPLTP medium and R-HDL, when added after rPLTP had been incubated with R-HDL. It was found, however, that anti-PLTP was able to inhibit the neutralization of LPS under these conditions (FIG. 25), strongly suggesting that PLTP interacts directly with LPS and transfers it to R-HDL.

Anti-PLTP IgG Does Not Inhibit Neutralization of LPS by Plasma. To determine whether PLTP was responsible for the neutralization of LPS in plasma, anti-PLTP IgG was tested for its ability to inhibit the neutralization of LPS by plasma with R-HDL, or by plasma alone. As mentioned above, anti-PLTP IgG inhibits most of the phospholipid transfer activity of whole plasma. To show that it also inhibits PLTP-mediated neutralization of LPS by R-HDL, LPS was incubated with R-HDL and rPLTP medium for 2 h in the presence of increasing concentrations of anti-PLTP IgG or control IgG (FIG. 26). In the absence of IgG, LPS is completely neutralized under these conditions (FIG. 24). Anti-PLTP IgG caused a dose-dependent, complete inhibition of this neutralization (corresponding to an increase of IL-6 production with increasing antibody concentration), whereas control IgG had no effect on neutralization (FIG. 26).

Anti-PLTP IgG was next examined for its affect on neutralization of LPS by R-HDL and plasma. Incubation of LPS with 3% plasma or R-HDL alone did not cause neutralization of LPS, but incubation with 3% plasma and R-HDL together caused time-dependent neutralization of LPS, with loss of at least 90% of the LPS activity after 2 h (FIG. 27A). Thus, plasma serves as a source of lipid transfer activity which allows neutralization of LPS by R-HDL. Addition of anti-PLTP or control IgG had no effect on the neutralization of LPS during a 2 h incubation of LPS with plasma and R-HDL (FIG. 27B). At the same concentration relative to the amount of plasma used, anti-PLTP was able to almost completely inhibit the phospholipid transfer activity of plasma. Taken together, these results suggest that PLTP in plasma does not contribute significantly to the ability of plasma to mediate neutralization of LPS by R-HDL. In addition, the effect of anti-PLTP IgG to inhibit the neutralization of LPS by plasma alone (using higher concentrations of plasma and lower concentrations of LPS) was examined. Again, it was not possible to show an effect of anti-PLTP IgG (not shown), suggesting that PLTP does not play a significant role in the neutralization of LPS by endogenous lipoproteins.

PLTP Does Not Mediate the Transfer of LPS to CD14. CD14 is a 55-kDa glycoprotein found as a glycosylphosphatidyl inositol (GPI)-linked protein on the surfaces of monocytes, macrophages and neutrophils, and as a soluble protein in blood, lacking the GPI anchor. Both of these forms of CD14 can bind LPS and mediate responses of cells to LPS (Wright et al., 1990, Science 249:1431; Wright et al., 1991, J. Exp. Med. 173:1281; Lee et al., 1992, J. Exp. Med. 175:1697; Frey et al., 1992, J. Exp. Med. 176:1665), and mice lacking CD14 are hyporesponsive to LPS (Haziot et al., 1974, Endotoxin Res. Abstracts 1:73), demonstrating the importance of CD14 in responses of animals to LPS. LBP mediates responses of CD14-bearing cells to LPS (Schumann et al., 1990, Science 249:1430), and we have shown recently that LBP can act catalytically to accelerate the binding of LPS to soluble CD14 (sCD14) (Hailman et al., 1994, J. Exp. Med. 179:269–277). Since LBP can transfer LPS either to lipoproteins or to CD14, experiments were performed to test whether PLTP could also transfer LPS to CD14.

Native PAGE was used to examine the ability of PLTP to transfer $^3$H-LPS to sCD14. Incubation of $^3$H-LPS with sCD14 alone yielded a faint band at the migratory position of CD14, indicating the formation of a small amount of $^3$H-LPS-sCD14 complex (not shown). When this incubation was done in the presence of LBP, most of the LPS comigrated with sCD14, suggesting complete transfer of $^3$H-LPS to sCD14 by LBP (not shown). When the incubation of $^3$H-LPS with sCD14 was done in the presence of increasing concentrations of rPLTP medium, there was no increase in the amount of $^3$H-LPS-sCD14 complex formed. The same concentrations of rPLTP medium were able to transfer $^3$H-LPS to R-HDL, suggesting that PLTP is unable to transfer LPS to CD14.

The adhesive responses of neutrophils to LPS was measured to confirm the inability of PLTP to transfer LPS to CD14. It was shown previously that neutrophils do not adhere to fibrinogen-coated plates in response to LPS alone, but do adhere in response to LPS with LBP (Hailman et al., 1994, J. Exp. Med. 179:269–277; Wurfel et al., 1994, J. Exp. Med. 180:1025–1035). This response depends on cell-surface CD14, since it can be inhibited with monoclonal antibodies to CD14 (Hailman et al., 1994, J. Exp. Med. 179:269–277). The ability of PLTP to transfer LPS to cell-surface CD14 was ascertained by incubating neutrophils with a fixed dose of IPS and increasing amounts of LBP or rPLTP medium (FIG. 28). Addition of low concentrations (10 ng/ml) of LBP allowed adhesion of neutrophils, whereas addition of rPLTP medium or control medium did not enhance the adhesive response. Similar concentrations of rPLTP medium were able to mediate neutralization of LPS by R-HDL (FIGS. 23 and 24). This result, and the previous experiment's results, show that PLTP is unable to transfer LPS to CD14.

PLTP Does Not Mediate Neutralization of LPS-sCD14 complexes by R-HDL. In addition to transferring "free" (micellar) LPS to R-HDL, LBP is also able to transfer LPS from LPS-sCD14 complexes to R-HDL (Wurfel et al., 1995, J. Exp.

Med. 181:1743–54). The failure of PLTP to transfer LPS to CD14 suggests that it lacks the ability to interact with CD14, and would not be expected to mediate the neutralization of LPS-sCD14 complexes by R-HDL. To test this possibility, LPS-sCD14 complexes were incubated with R-HDL for increasing times, in the presence of LBP or rPLTP medium. As little as 100 ng/ml of LBP enabled efficient neutralization of LPS-sCD14 complexes by R-HDL, whereas addition of rPLTP medium had no such effect (FIG. 29). The same concentration of rPLTP medium enabled neutralization of LPS by R-HDL (FIG. 24), suggesting that LPS bound to sCD14 is protected from interaction with rPLTP. The above results strongly suggest that PLTP is unable to interact with CD14, and that the ability to transfer LPS to or from CD14 is unique to LBP.

PLTP Purified from Plasma Transfers $^3$HLPS to R-HDL, but Not to sCD14. Since purification of PLTP results in rapid loss of its activity, the experiments shown above were all performed with RPLTP medium, because the LPS transfer activity was very stable over time. To confirm the above results, PLTP purified from human plasma was used, and its ability to transfer $^3$H-LPS to R-HDL and sCD14 was examined. Consistent with the above results, purified PLTP enabled the transfer of $^3$H-LPS to R-HDL, but not to sCD14 (FIG. 30).

Discussion

In previous studies, it was shown that LBP can catalyze the movement of LPS to CD14 (Hailman et al., 1994, J. Exp. Med. 179:269–277), enabling responses to LPS, or to lipoproteins (Wurfel et al., 1994, J. Exp. Med. 180:1025–1035; Wurfel et al., 1995, J. Exp. Med. 181:1743–54), neutralizing the biological activity of LPS. Here it is shown that PLTP can transfer LPS to R-HDL, but not to CD14. Thus, PLTP can interact with LPS and facilitate its neutralization, but does not enhance responses of cells to LPS. The ability to interact with LPS was shown previously for LBP and for bactericidal/permeability-increasing protein (BPI), a neutrophil granule protein with bactericidal activity and the ability to neutralize LPS (Elsbach and Weiss, 1992, *Inflammation: basic principles and clinical correlates.* Gallin et al., eds, pp. 603–636, Raven Press, New York). PLTP has sequence similarity to human LBP (24% identity) and BPI (26% identity) (Day et al., 1994, J. Biol. Chem 269:9388–9391), and all three proteins have been mapped to human chromosome 20 (Day et al., 1994, J. Biol. Chem 269:9388–939; Gray et al., 1993, Genomics 15:188–190). PLTP also has sequence similarity to CETP (Day et al., 1994, J. Biol. Chem 269:9388–9391; Drayna et al., 1987, Nature 327:632–634), but human CETP maps to chromosome 16 (Lusis et al., 1987, Genomics 1:232–235). Whether CETP can also act as a transfer protein for LPS has not been studied, but it has been shown to transfer phospholipids between lipoprotein particles, so it may, like PLTP, also transfer LPS to lipoproteins.

The results with PLTP presented in the present Example have implication for the mechanism of action of LBP. The ability of LBP to transfer LPS to either CD14 or lipoproteins suggested that LBP might act only to disaggregate LPS, releasing monomeric LPS which would then bind to any available binding sites. That PLTP can transfer LPS only to lipoprotein particles implies that LBP specifically interacts with CD14 during the transfer of LPS. Another suggestion that LBP does not merely disaggregate LPS is its ability to transfer LPS from LPS-sCD14 complexes to R-HDL (Wurfel et al., 1995, J. Exp. Med. 181:1743–54). Since each CD14 molecule binds only one or two molecules of LPS, the action of LBP in this reaction is not merely to release monomers of LPS from micelles or other aggregates of LPS. The inability of PLTP to transfer LPS from LPS-sCD14 complexes to R-HDL (FIG. 29) further supports the idea that LBP interacts specifically with CD14 during transfer reactions, and that PLTP lacks the ability to interact with CD14. The ability of a lipid transfer protein to transfer a lipid molecule to another protein, rather than to a lipoprotein or membrane appears to be unique to LBP, but it is possible that other lipid-binding proteins also can use lipid transfer proteins.

That LBP may possess unique amino acid sequences necessary for its specific interaction with CD14 is supported by the finding that an amino-terminal fragment of LBP binds LPS but appears to be unable to transfer LPS to CD14 (Theofan et al., 1994, J. Immunol. 152:3623–3629; Han et al., 1994, J. Biol. Chem 269:8172–8175). It has not been shown whether the amino-terminal fragment of LBP is able to transfer LPS to R-HDL, however. This fragment may be lacking sequences needed for the transfer of LPS to either CD14 or R-HDL; that is, the binding of LPS may not be sufficient for the transfer of LPS. On the other hand, if the amino-terminal fragment of LBP were able to transfer LPS to R-HDL, it would strengthen the argument that there is a specific sequence in the carboxy-terminal portion of LBP needed for interactions with CD14.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various references are cited throughout this specification, each of which is incorporated herein by reference in its entirety.

What is claimed is:

1. A method for monitoring or prognoisis of a subject suffering from gram-negative or endotoxin-mediated sepsis comprising:

a) measuring a first level of lipoprotein particles that contain a lipid exchange protein that is characterized by being capable of facilitating an exchange of lipopolysaccharide into the high density lipoprotein particles in a biological fluid of the subject, wherein the high density lipoprotein particles comprise lipoprotein A-I, and the lipid exchange protein is lipopolysaccharide binding protein;

b) measuring a second level of lipoprotein particles that contain a lipid exchange protein that is characterized by being capable of faciliating an exchange of lipopolysaccharide into the high density lipoprotein particles in the biological fluid of the subject, wherein the high density lipoprotein particles comprise lipoprotein A-I, and the lipid exchange protein is lipopolysaccharide binding protein; and c) comparing the second level measured in step (h) with the first level measured in step (a), wherein an increase in the level indicates greater probability of a favorable outcome of the sepsis.

2. The method according to claim 1, wherein the lipid exchange proteins lipopolysaccharide binding protein.

3. The method according to claim 1, wherein the measuring comprises detecting a portion of lipoprotein particles containing apolipoprotein A-I that also contain lipopolysaccharide binding protein.

4. The method according to claim 1, wherein the measuring comprises detecting the capacity of plasma or serum from the subject to neutralize lipopolysaccharide activity.

5. The method according to claim 1, wherein the lipid exchange protein is phospholipid transfer protein.

6. The method of claim 1, wherein the biological fluid of the subject comprises plasma or serum.

7. The method of claim 3, wherein the detecting comprises measuring adherence of PMN to fibrinogen of the biological fluid, measuring induction of expression of cytokines in the biological fluid, or assaying the biological fluid by immunoassay.

8. The method of claim 7, wherein the immunoassay comprises antibodies reactive with a component of the high density lipoprotein containing lipoprotein A-I, or the lipopolysaccharide binding protein, or both.

9. The method of claim 7, wherein the cytokines comprise TNF or IL-1.

10. The method of claim 4, wherein the detecting comprises measuring the adherence of PMN to fibrinogen of the biological fluid, measuring the induction of expression of cytokines in the biological fluid, or assaying the biological fluid with an immunoassay.

11. The method of claim 10, wherein the immunoassay comprises antibodies reactive with a component of the lipoprotein or the lipopolysaccharide exchange protein, or both.

12. The method of claim 9, wherein the cytokines comprise TNF or IL-1.

* * * * *